United States Patent
Morell et al.

(10) Patent No.: US 7,667,114 B2
(45) Date of Patent: Feb. 23, 2010

(54) STARCH BRANCHING ENZYME

(75) Inventors: Matthew Morell, Australian Capital Territory (AU); Sadequr Rahman, Melba, Australian Capital Territory (AU); Ahmed Regina, Australian Capital Territory (AU)

(73) Assignees: Commonwealth Scientific and Industrial Research Organisation, Campbell (AU); Biogemma SAS, Paris (FR)

( * ) Notice: Subject to any disclaimer, the term of this patent is extended or adjusted under 35 U.S.C. 154(b) by 1271 days.

(21) Appl. No.: 10/204,347

(22) PCT Filed: Feb. 21, 2001

(86) PCT No.: PCT/AU01/00175

§ 371 (c)(1),
(2), (4) Date: Dec. 20, 2002

(87) PCT Pub. No.: WO01/62934

PCT Pub. Date: Aug. 30, 2001

(65) Prior Publication Data

US 2005/0164178 A1    Jul. 28, 2005

(30) Foreign Application Priority Data

Feb. 21, 2000 (AU) .................... PQ57442

(51) Int. Cl.
*A01H 5/00* (2006.01)
*C07H 21/04* (2006.01)
*C12N 15/00* (2006.01)

(52) U.S. Cl. .................... 800/320.3; 800/284; 800/295; 536/23.2; 536/23.6

(58) Field of Classification Search .................... None
See application file for complete search history.

(56) References Cited

U.S. PATENT DOCUMENTS 5,866,793 A  2/1999  Båga et al.
6,730,825 B1 *  5/2004  Goldsbrough et al. ....... 800/284
6,916,976 B1 *  7/2005  Li et al. .................... 800/320.3

FOREIGN PATENT DOCUMENTS

WO    WO 97/22703    6/1997
WO    WO 00/15810    3/2000

OTHER PUBLICATIONS

Baga et al 1999 Starch 51:11-116, provided by Applicant in IDS.*
Supplemental European Search Report of EP 01 90 7236.2.
Matoko Takaoka et al., "Structural Characterization of High Molecular Weight Starch Granule-Bound Proteins in Wheat (*Triticum aestivum* L.)", J. Agric. Food Chem., 1997, 45, pp. 2929-2934.
Matthew K. Morrell et al., "Differential Expression and Properties of Starch Branching Enzyme Isoforms in Developing Wheat Endosperm[1]", Plant Physiol. (1997), 113: 201-208.
Sadequr Rahman et al. "The Major Proteins of Wheat Endosperm Starch Granules", Aust. J. Plant Physiol., 1995, 22: 793-803.
Sadequr Rahman et al., "Comparison of Starch-Branching Enzyme Genes Reveals Evolutionary Relationships Among Isoforms. Characterization of a Gene for Starch-Branching Enzyme IIa from the Wheat D Gemome Donor *Aegilops tauschii*[1]", Plant Physiology, Mar. 2001, vol. 125, pp. 1314-1324.
Monica Båga et al., "Wheat Starch Modification Through Biotechnology", Starch/Stärke 51 (1999) Nr. 4 S. 111-116.

* cited by examiner

*Primary Examiner*—Anne Marie Grunberg
*Assistant Examiner*—Brent Page
(74) *Attorney, Agent, or Firm*—Stephen A. Bent; Foley & Lardner LLP

(57) ABSTRACT

This invention relates to a new starch branching enzyme, and to the gene encoding the enzyme. In particular, the invention provides a new starch branching enzyme type II from wheat, the nucleic acid encoding the enzyme, and constructs comprising the nucleic acid. The invention also relates to a novel method for identification of branching enzyme type II proteins, which is useful for screening wheat germplasm for null or altered alleles of wheat branching enzyme IIb. The novel gene, protein and methods of the invention are useful in production of plants which produce grain with novel properties for food and industrial applications, for example wheat grain containing high amylose or low amylopectin starch.

9 Claims, 34 Drawing Sheets

Sequence of the wheat SBE9 (BEIIa) cDNA

```
   1 ACGTTGCTCC CCCTTCTCAT CGCTTCTCAA TTAATATCTC CATCACTCGG
  51 TTCCGCGCTG CATTTCGGCC GGCGGGTTGA GTGAGATCTG GGCCACTGAC
 101 CGACTCACTC GCTCGCTGCG GGGATGGCGA CGTTCGCGGT GTCCGGCGCG
 151 ACCCTCGGTG TGGCGCGGCC GCCGGCGGCG GCGCAACCTG AAGAATTACA
 201 GATACCTGAA GACATCGAGG AGCAAACGGC TGAAGTAAAC ATGACAGGGG
 251 GGACTGCAGA AAAACTTGAA TCTTCAGAAC CGACTCAAGG CATTGTGGAA
 301 ACAATCACTG ATGGTGTAAC CAAAGGAGTT AAGGAACTAG TCGTGGGGGA
 351 GAAACCGCGA GTTGTCCCAA AACCAGGAGA TGGGCAGAAA ATATACGAGA
 401 TTGACCCAAC GCTGAAAGAT TTTCGGAGCC ATCTTGACTA CCGATACAGC
 451 GAATACAGGA GAATTCGTGC TGCTATTGAC CAACATGAAG GTGGATTGGA
 501 AGCATTTTCT CGTGGTTATG AAAAGCTTGG ATTTACCCGC AGTGCTGAAG
 551 GTATCACTTA CCGAGAATGG GCTCCTGGAG CGCATTCTGC AGCATTAGTA
 601 GGTGACTTCA ACAATTGGAA TCCGAATGCA GATACTATGA CCAGAGATGA
 651 TTATGGTGTT TGGGAGATTT CCTCCCTAA CAATGCTGAT GGATCCCCAG
 701 CTATTCCTCA TGGCTCACGT GTAAAGATAC GGATGGATAC TCCATCTGGT
 751 GTGAAGGATT CAATTTCTGC TTGGATCAAG TTCTCTGTGC AGGCTCCAGG
 801 TGAAATACCA TTCAATGGCA TATATTATGA TCCACCTGAA GAGGAGAAGT
 851 ATGTCTTCCA ACATCCTCAA CCTAAACGAC CAGAGTCACT GAGGATTTAT
 901 GAATCACACA TTGGAATGAG CAGCCCAGAA CCGAAGATAA ATTCATATGC
 951 TAATTTTAGG GATGAGGTGC TGCCAAGAAT TAAAAGGCTT GGATACAATG
1001 CAGTGCAGAT AATGGCAATC CAGGAGCATT CATACTATGC GAGCTTTGGG
1051 TACCATGTTA CTAATTTTTT TGCACCAAGT AGCCGTTTTG GAACTCCAGA
1101 GGACTTAAAA TCCCTGATCG ATAGAGCACA TGAGCTTGGT TTGCTTGTTC
1151 TTATGGATAT TGTTCATAGT CATTCATCAA ATAATACCCT TGACGGCTTG
1201 AATGGTTTCG ATGGCACTGA TACACATTAC TTCCACGGTG GTCCACGTGG
1251 CCATCATTGG ATGTGGGATT CTCGTCTATT CAACTATGGG AGTTGGGAAG
1301 TATTGAGATT CTTACTGTCA AACGCGAGAT GGTGGCTTGA AGAATATAAG
1351 TTTGATGGAT TTCGATTTGA TGGGGTGACC TCCATGATGT ATACTCACCA
1401 TGGATTACAA ATGACATTTA CTGGGAACTA TGGCGAGTAT TTTGGATTTG
1451 CTACTGATGT TGATGCGGTA GTTTACTTGA TGCTGGTCAA CGATCTAATT
1501 CATGGACTTC ATCCTGATGC TGTATCCATT GGTGAAGATG TCAGTGGAAT
1551 GCCCACATTT TGCATCCCTG TTCCAGATGG TGGTGTTGGT TTTGACTATC
1601 GCTTGCATAT GGCTGTAGCA GATAAATGGA TTGAACTCCT CAAGCAAAGT
1651 GACGAATCTT GGAAAATGGG TGATATTGTG CACACCCTAA CAAATAGAAG
1701 GTGGCTTGAG AAGTGTGTAA CTTATGCAGA AAGTCATGAT CAAGCACTAG
1751 TTGGTGACAA GACTATTGCA TTCTGGTTGA TGGATAAGGA TATGTATGAT
1801 TTCATGGCTC TGGATAGGCC TTCAACTCCT CGCATTGATC GTGGCATAGC
1851 ATTACATAAA ATGATCAGGC TTGTCACCAT GGGTTTAGGT GGTGAAGGCT
1901 ATCTTAACTT CATGGGAAAT GAGTTTGGGC ATCCTGAATG GATAGATTTT
1951 CCAAGAGGTC CGCAAACTCT TCCAACCGGC AAAGTTCTCC CTGGAAATAA
2001 CAATAGTTAT GATAAATGCC GCCGTAGATT TGATCTTGGA GATGCAGATT
2051 TTCTTAGATA TCATGGTATG CAAGAGTTCG ATCAGGCAAT GCAGCATCTT
2101 GAGGAAAAAT ATGGGTTTAT GACATCTGAG CACCAGTATG TTTCACGGAA
2151 ACATGAGGAA GATAAGGTGA TCATCTTCGA AAGAGGAGAT TTGGTATTTC
2201 TTTTCAACTT CCACTGGAGC AATAGCTTTT TTGACTACCG TGTTGGGTGT
2251 TCCAGGCCTG GGAAGTACAA GGTGGCCTTA GACTCCGACG ATGCACTCTT
2301 TGGTGGATTC AGCAGGCTTG ATCATGATGT CGACTACTTC ACAACCGAAC
2351 ATCCGCATGA CAACAGGCCG CGCTCTTTCT CGGTGTACAC TCCGAGCAGA
2401 ACTGCGGTCG TGTATGCCCT TACAGAGTAA GAACCAGCAG CTGCTTGTTA
2451 CAAGGCAAAG AGAGAACTCC AGAGAGCTCG TGGATCGTGA GCGAAGCGAC
2501 GGGCAACGGC GCGAGGCTGC TCTAAGCGCC ATGACTGGGA GGGGATCGTG
2551 CCTCTTCCCC AGATGCCAGG AGGAGCAGAT GGATAGGTAG CTTGTTGGTG
2601 AGCGCTCGAA AGAAAATGGA CGGGCCTGGG TGTTTGTCGT GCTGCACTAC
2651 CCTCCTCCTA TCTTGCACAT TCCCGGTTGT TTTTGTACAT ATAACTAATA
2701 ATTGCCCGTG CGCTCAACGT GAACAA
```

*Figure 1*

Sequence of the Starch Branching Enzyme II gene (wSBE II-D1)
from *A. tauschii*

```
   1 AGAAACACCT CCATTTTAGA TTTTTTTTTT GTTCTTTTCG GACGGTGGGT
  51 CGTGGAGAGA TTAGCGTCTA GTTTTCTTAA AAGAACAGGC CATTTAGGCC
 101 CTGCTTTACA AAAGGCTCAA CCAGTCCAAA ACGTCTGCTA GGATCACCAG
 151 CTGCAAAGTT AAGCGCGAGA CCACCAAAAC AGGCGCATTC GAACTGGACA
 201 GACGCTCACG CAGGAGCCCA GCACCACAGG CTTGAGCCTG ACAGCGGACG
 251 TGAGTGCGTG ACACATGGGG TCATCTATGG GCGTCGGAGC AAGGAAGAGA
 301 GACGCACATG AACACCATGA TGATGCTATC AGGCCTGATG GAGGGAGCAA
 351 CCATGCACCT TTTCCCCTCT GGAAATTCAT AGCTCACACT TTTTTTTAAT
 401 GGAAGCAAGA GTTGGCAAAC ACATGCATTT TCAAACAAGG AAAATTAATT
 451 CTCAAACCAC CATGACATGC AATTCTCAAA CCATGCACCG ACGAGTCCAT
 501 GCGAGGTGGA AACGAAGAAC TGAAAATCAA CATCCCAGTT GTCGAGTCGA
 551 GAAGAGGATG ACACTGAAAG TATGCGTATT ACGATTTCAT TTACATACAT
 601 GTACAAATAC ATAATGTACC CTACAATTTG TTTTTGGAG CAGAGTGGTG
 651 TGGTCTTTTT TTTTTACACG AAAATGCCAT AGCTGGCCCG CATGCGTGCA
 701 GATCGGATGA TCGGTCGGAG ACGACGGACA ATCAGACACT CACCAACTGC
 751 TTTTGTCTGG GACACAATAA ATGTTTTTGT AAACAAAATA AATACTTATA
 801 AACGAGGGTA CTAGAGGCCG CTAACGGCAT GGCCAGGTAA ACGCGCTCCC
 851 AGCCGTTGGT TTGCGATCTC GTCCTCCCGC ACGCAGCGTC GCCTCCACCG
 901 TCCGTCCGTC GCTGCCACCT CTGCTGTGCG CGCGCACGAA GGGAGGAAGA
 951 ACGAACGCCG CACACACACT CACACACGGC ACACTCCCCG TGGGTCCCCT
1001 TTCCGGCTTG GCGTCTATCT CCTCTCCCCC GCCCATCCCC ATGCACTGCA
1051 CCGTACCCGC CAGCTTCCAC CCCCGCCGCA CACGTTGCTC CCCCTTCTCA
1101 TCGCTTCTCA ATTAATATCT CCATCACTCG GGTTCCGCGC TGCATTTCGG
1151 CCGGCGGGTT GAGTGAGATC TGGGCGACTG GCTGACTCAA TCACTACGCG
1201 GGGATGGCGA CGTTCGCGGT GTCCGGCGCG ACTCTCGGTG TGGCGCGGGC
1251 CGGCGTCGGA GTGGCGCGGG CCGGCTCGGA GCGGAGGGGC GGGGCGGACT
1301 TGCCGTCGCT GCTCCTCAGG AAGAAGGACT CCTCTCGTAC GCCTCGCTCT
1351 CTCGAATCTC CCCCGTCTGG CTTTGGCTCC CCTTCTCTCT CCTCTGCGCG
1401 CGCATGGCCT GTTCGATGCT GTTCCCCAAT TGATCTCCAT GAGTGAGAGA
1451 GATAGCTGGA TTAGCGATC GCGCTTCCTG AACCTGTATT TTTTCCCCCG
1501 CGGGGAAATG CGTTAGTGTC ACCCAGGCCC TGGTGTTACC ACGGCTTTGA
1551 TCATTCCTCG TTTCATTCTG ATATATATTT TCTCATTCTT TTTCTTCCTG
1601 TTCTTGCTGT AACTGCAAGT TGTGGCGTTT TTTCACTATT GTAGTCATCC
1651 TTGCATTTTG CAGGCGCCGT CCTGAGCCGC GCGGCCTCTC CAGGGAAGGT
1701 CCTGGTGCCT GACGGCGAGA GnGACGACTT GGCAAGTCCG GCGCAACCTG
1751 AAGAATTACA GGTACACACA CTCGTGCCGG TAAATCTTCA TACAATCGTT
1801 ATTCACTTAC CAAATGCCGG ATGAAACCAA CCACGGATGC GTCAGGTTTC
1851 GAGCTTCTTC TATCAGCATT GTGCAGTACT GCACTGCCTT GTTCATTTTG
1901 TTAGCCTTGG CCCCGTGCTG GCTCTTGGGC CACTGAAAAA ATCAGATGGA
1951 TGTGCATTCT AGCAAGAACT TCACAACATA ATGCACCGTT TGGGGTTTCG
2001 TCAGTCTGCT CTACAATTGC TATTTTTCGT GCTGTAGATA CCTGAAGATA
2051 TCGAGGAGCA AACGGCGGAA GTGAACATGA CAGGGGGCAC TGCAGAGAAA
2101 CTTCAATCTT CAGAACCGAC TCAGGGCATT GTGGAAACAA TCACTGATGG
2151 TGTAACCAAA GGAGTTAAGG AACTAGTCGT GGGGGAGAAA CCGCGAGTTG
2201 TCCCAAAACC AGGAGATGGG CAGAAAATAT ACGAGATTGA CCCAACACTG
2251 AAAGATTTTC GGAGCCATCT TGACTACCGG TAATGCCTAC CCGCTGCTTT
2301 CGCTCATTTT GAATTAAGGT CCTTTCATCA TGCAAATTTG GGGAACATCA
2351 AAGAGACAAA GACTAGGGAC CACCATTTCA TACAGATCCC TTCGTGGTCT
2401 GAGAATATGC TGGGAAGTAA ATGTATAATT GATGGCTACA ATTTGCTCAA
2451 AATTGCAATA CGAATAACTG TCTCCGATCA TTACAATTAA AGAGTGGCAA
2501 ACTGATGAAA ATGTGGTGGA TGGGTTATAG ATTTTACTTT GCTAATTCCT
2551 CTACCAAATT CCTAGGGGG AAATCTACCA GTTGGGAAAC TTAGTTTCTT
2601 ATCTTTGTGG CCTTTTTGTT TTGGGAAAAA CACATTGCTA AATTCGAATG
2651 ATTTTGGGTA TACCTCGGTG GATTCAACAG ATACAGCGAA TACAAGAGAA
2701 TTCGTGCTGC TATTGACCAA CATGAAGGTG GATTGGAAGC ATTTTCTCGT
2751 GGTTATGAAA AGCTTGGATT TACCCGCAGG TAAATTTAAA GCTTTATTAT
2801 TATGAAACGC CTCCACTAGT CTAATTGCAT ATCTTATAAG AAAATTTATA
2851 ATTCCTGTTT TCCCCTCTCT TTTTTCCAGT GCTGAAGGTA TCGTCTAATT
2901 GCATATCTTA TAAGAAAATT TATATTCCTG TTTTCCCCTA TTTTCCAGTG
2951 CTGAAGGTAT CACTTACCGA GAATGGGCTC CCTGGAGCGC ATGTTATGTT
3001 CTTTTAAGTT CCTTAACGAG ACACCTTCCA ATTTATTGTT AATGGTCACT
3051 ATTCACCAAC TAGCTTACTG GACTTACAAA TTAGCTTACT GAATACTGAC
3101 CAGTTACTAT AAATTTATGA TCTGGCTTTT GCACCCTGTT ACAGTCTGCA
3151 GCATTAGTAG GTGACTTCAA CAATTGGAAT CCAAATGCAG ATACTATGAC
3201 CAGAGTATGT CTACAGCTTG GCAATTTTCC ACCTTTGCTT CATAACTACT
3251 GATACATCTA TTTGTATTTA TTTAGCTGTT TGCACATTCC TTAAAGTTGA
```

*Figure 2*

```
3301  GCCTCAACTA CATCATATCA AAATGGTATA ATTTGTCAGT GTCTTAAGCT
3351  TCAGCCCAAA GATTCTACTG AATTTAGTCC ATCTTTTTGA GATTGAAAAT
3401  GAGTATATTA AGGATGAATG AATACGTGCA ACACTCCCAT CTGCATTATG
3451  TGTGCTTTTC CATCTACAAT GAGCATATTT CCATGCTATC AGTGAAGGTT
3501  TGCTCCTATT GATGCAGATA TTTGATATGG TCTTTTCAGG ATGATTATGG
3551  TGTTTGGGAG ATTTTCCTCC CTAACAACGC TGATGGATCC TCAGCTATTC
3601  CTCATGGCTC ACGTGTAAAG GTAAGCTGGC CAATTATTTA GTCGAGGATG
3651  TAGCATTTTC GAACTCTGCC TACTAAGGGT CCCTTTTCCT CTCTGTTTTT
3701  TAGATACGGA TGGATACTCC ATCCGGTGTG AAGGATTCAA TTTCTGCTTG
3751  GATCAAGTTC TCTGTGCAGG CTCCAGGTGA AATACCTTTC AATGGCATAT
3801  ATTATGATCC ACCTGAAGAG GTAAGTATCG ATCTACATTA CATTATTAAA
3851  TGAAATTTCC AGTGTTACAG TTTTTTAATA CCCACTTCTT ACTGACATGT
3901  GAGTCAAGAC AATACTTTTG AATTTGGAAG TGACATATGC ATTAATTCAC
3951  CTTCTAAGGG CTAAGGGCA ACCAACCTTG GTGATGTGTG TATGCTTGTG
4001  TGTGACATAA GATCTTATAG CTCTTTTATG TGTTCTCTGT TGGTTAGGAT
4051  ATTCCATTTT GGCCTTTTGT GACCATTTAC TAAGGATATT TACATGCAAA
4101  TGCAGGAGAA GTATGTCTTC CAACATCTCA ACTAAACGAC CAGAGTCACT
4151  AAGGATTTAT GAATCACACA TTGGAATGAG CAGCCCGGTA TGTCAATAAG
4201  TTATTCACC TGTTTCTGGT CTGATGGTTT ATTCTATGGA TTTTCTAGTT
4251  CTGTTATGTA CTGTTAACAT ATTACATGGT GCATTCACTT GACAACCTCG
4301  ATTTTATTTT CTAATGTCTT CATATTGGCA AGTGCAAAAC TTTGCTTCCT
4351  CTTTGTCTGC TTGTTCTTTT GTCTTCTGTA AGATTTCCAT TGCATTTGGA
4401  GGCAGTGGGC ATGTGAAAGT CATATCTATT TTTTTTTTGT CAGAGCATAG
4451  TTATATGAAT TCCATTGTTG TTGCAATAGC TCGGTATAAT GTAACCATGT
4501  TACTAGCTTA AGATTTCCCA CTTAGGATGT AAGAAATATT GCATTGGAGC
4551  GTCTCCAGCA AGCCATTTCC TACCTTATTA ATGAGAGAGA GACAAGGGGG
4601  GGGGGGGGGG GGGGGTTCCC TTCATTATTC TGCGAGCGAT TCAAAAACTT
4651  CCATTGTTCT GAGGTGTACG TACTGCAGGG ATCTCCCATT ATGAAGAGGA
4701  TATAGTTAAT TCTTTGTAAC CTACTTGGAA ACTTGAGTCT TGAGGCATCG
4751  CTAATATATA CTATCATCAC AATACTTAGA GGATGCATCT GAAnATTTTA
4801  GTGTGATCTT GCACAGGAAC CGAAGATAAA TTCATATGCT AATTTTAGGG
4851  ATGAGGTGTT GCCAAGAATT AAAAGGCTTG GATACAATGC AGTGCAGATA
4901  ATGGCAATCC AGGAGCATTC ATACTATGCA AGCTTTGGGT ATTCACACAA
4951  TCCATTTTTT TCTGTATACA CnTCTTCACC CATTTGGAGT TATTACATCC
5001  TAATGCTTCA TGCACATAAA ATATTTGGAT ATAATCCTTT ATTAGATATA
5051  TAGTACAACT ACACTTAGTA TTCTGAnnAA nAAGATCATT TTATTGTTGT
5101  TGGCTTGTTC CAGGTACCAT GTTACTAATT TTTTTGCACC AAGTAGCCGT
5151  TTTGGAACTC CAGAGGACTT AAAATCCTTG ATCGATAGAG CACATGAGCT
5201  TGGTTTGCTT GTTCTTATGG ATATTGTTCA TAGGTAATTA GTCCAATTTA
5251  ATTTTAGCTG TTTTACTGTT TATCTGGTAT TCTAAAGGGA AATTCAGGCA
5301  ATTATGATAC ATTGTCAAAA GCTAAGAGTG GCGAAAGTGA AATGTCAAAA
5351  TCTAGAGTGG CATAAGGAAA ATTGGCAAAA ACTAGAGTGG CAAAAATAAA
5401  ATTTTCCCAT CCTAAATGGC AGGGCCCTAT CGCCGAATAT TTTTCCATTC
5451  TATATAATTG TGCTACGTGA CTTCTTTTTT CTCAGATGTA TTAAACCAGT
5501  TGGACATGAA ATGTATTTGG TACATGTAGT AAACTGACAG TTCCATAGAA
5551  TATCGTTTTG TAATGGCAAC ACAATTTGAT GCCATAGATG TGGATTGAGA
5601  AGTTCAGATG CTATCAATAG AATTAATCAA CTGGCCATGT ACTCGTGGCA
5651  CTACATATAG TTTGCAAGTT GGAAAACTGA CAGCAATACC TCACTGATAA
5701  GTGGCCAGGC CCCACTTGCC AGCTTCATAC TAGATGTTAC TTCCCTGTTG
5751  AATTCATTTG AACATATTAC TTAAAGTTCT TCATTTGTCC TAAGTCAAAC
5801  TTCTTTAAGT TTGACCAAGT CTATTGGAAA ATATATCAAC ATCTACAACA
5851  CCAAATTACT TTGATCAGAT TAACAATTTT TATTTTATTA TATTAGCACA
5901  TCTTTGATGT TGTAGATATC AGCACATTTT TCTATAGACT TGGTCAAATA
5951  TAGAGAAGTT TGACTTAGGA CAAATCTAGA ACTTCAATCA ATTGGATCA
6001  GAGGGAACAT CAAATAATAT AGATAGATGT CAACACTTCA ACAAAAAAAT
6051  CAGACCTTGT CACCATATAT GCATCAGACC ATCTGTTTGC TTTAGCCACT
6101  TGCTTTCATA TTTATGTGTT TGTACCTAAT CTACTTTTCC TTCTACTTGG
6151  TTTGGTTGAT TCTATTTCAG TTGCATTGCT TCATCAATGA TTTTGTGTAC
6201  CCTGCATCA TTCGTCAAAT AATACCCTTG ACGGTTTGAA TGGTTTCGAT
6251  GGCACTGATA CACATTACTT CCACGGTGGT CCACGCGGCC ATCATTGGAT
6301  GTGGGATTCT CGTCTATTCA ACTATGGGAG TTGGGAAGTA TGTAGCTCTG
6351  ACTTCTGTCA CCATATTTGG CTAACTGTTC CTGTTAATCT GTTCTTACAC
6401  ATGTTGATAT TCTATTCTTA TGCAGGTATT GAGATTCTTA CTGTCAAACG
6451  CGAGATGGTG GCTTGAAGAA TATAAGTTTG ATGGATTTCG ATTTGATGGG
6501  GTGACCTCCA TGATGTATAC TCACCATGGA TTACAAGTAA GTCATCAAGT
6551  GGTTTCAGTA ACTTTTTTAG GGCACTGAAA CAATTGCTAT GCATCATAAC
6601  ATGTATCATG ATCAGGACTT GTGCTACGGA GTCTTAGATA GTTCCCTAGT
6651  ATGCTTGTAC AATTTTACCT GATGAGATCA TGGAAGATTG GAAGTGATTA
6701  TTATTTATTT TCTTTCTAAG TTTGTTTCTT GTTCTAGATG ACATTTACTG
```

*Figure 2 (cont'd)*

```
 6751   GGAACTATGG CGAATATTTT GGATTTGCTA CTGATGTTGA TGCGGTAGTT
 6801   TACTTGATGC TGGTCAACGA TCTAATTCAT GGACTTTATC CTGATGCTGT
 6851   ATCCATTGGT GAAGATGTAA GTGCTTACAG TATTTATGAT TTTTAACTAG
 6901   TTAAGTAGTT TTATTTTGGG GATCAGTCTG TTACACTTTT TGTTAGGGGT
 6951   AAAATCTCTC TTTTCATAAC AATGCTAATT TATACCTTGT ATGATAATGC
 7001   ATCACTTAnG TAATTTGAAA AGTGCAAGGG CATTCAAGCT TACGAGCATA
 7051   TTTTTTGATG GCTGTAATTT ATTTGATAGT ATGCTTGTTT GGGTTTTTCA
 7101   ATAAGTGGGA GTGTGTGACT AATGTTGTAT TATTTATTTA ATTGCGGAAG
 7151   AAATGGGCAA CCTTGTCAAT TGCTTCAGAA GGCTAACTTT GATTCCATAA
 7201   ACGCTTTGGA AATGAGAGGC TATTCCCAAG GACATGAATT ATACTTCAGT
 7251   GTGTTCTGTA CATGTATTTG TAATAGTGGT TTAACTTAAA TTCCTGCACT
 7301   GCTATGGAAT CTCACTGTAT GTTGTnAGTG TACACATCCA CAAACAAGTA
 7351   ATCCTGAGCT TTCAACTCAT GAGAAAATAn GAnGTCCGCT TCTGCCAGCA
 7401   TTAACTGTTC ACAGTTCTAA TTTGTGTAAC TGTGAAATTG TTCAGGTCAG
 7451   TGGAATGCCT ACATTTTGCA TCCCTGTTCC AGATGGTGGT GTTGGTTTTG
 7501   ACTACCGCCT GCATATGGCT GTAGCAGATA AATGGATTGA ACTCCTCAAG
 7551   TAAGTGCAGG AATATTGGTG ATTACATGCG CACAATGATC TAGATTACAT
 7601   TTTCTAAATG GTAAAAAGGA AAATATGTAT GTGAATATCT AGACATTTGC
 7651   CTGTTATCAG CTTGAATACG AGAAGTCAAA TACATGATTT AAATAGCAAA
 7701   TCTCGGAAAT GTAATGGCTA GTGTCTTTAT GCTGGGCAGT GTACATTGCG
 7751   CTGTAGCAGG CCAGTCAACA CAGTTAGCAA TATTTTCAGA AACAATATTA
 7801   TTTATATCCG TATATGAnGA AAGTTAGTAT ATAAACTGTG GTCATTAATT
 7851   GTGTTCACCT TTTGTCCTGT TTAAGGATGG GCAGTAGGTA ATAAATTTAG
 7901   CCAGATAAAA TAAATCGTTA TTAGGTTTAC AAAAGGAATA TACAGGGTCA
 7951   TGTAGCATAT CTAGTTGTAA TTAATGAAAA GGCTGACAAA AGGCTCGGTA
 8001   AAAAAACTT TATGATGATC CAGATAGATA TGCAGGAACG CGACTAAAGC
 8051   TCAAATACTT ATTGCTACTA CACAGCTGCC AATCTGTCAT GATCTGTGTT
 8101   CTGCTTTGTG CTATTTAGAT TTAAATACTA ACTCGATACA TTGGCAATAA
 8151   TAAACTTAAC TATTCAACCA ATTTGGTGGA TACCAGAnAT TTCTGCCCTC
 8201   TTGTTAGTAA TGATGTGCTC CCTGCTGCTG TTCTCTGCCG TTACAAAAGC
 8251   TGTTTTCAGT TTTTTGCATC ATTATTTTTG TGTGTGAGTA GTTTAAGCAT
 8301   GTTTTTTGAA GCTGTGAGCT GTTGGTACTT AATACATTCT TGGAAGTGTC
 8351   CAAATATGCT GCAGTGTAAT TTAGCATTTC TTTAACACAG GCAAAGTGAC
 8401   GAATCTTGGA AAATGGGCGA TATTGTGCAC ACCCTAACAA ATAGAAGGTG
 8451   GCTTGAGAAG TGTGTAACTT ATGCAGAAAG TCATGATCAA GCACTAGTTG
 8501   GTGACAAGAC TATTGCATTC TGGTTGATGG ATAAGGTACT AGCTGTTACT
 8551   TTTGGACAAA AGAATTACTC CCTCCCGTTC CTAAATATAA GTCTTTGTAG
 8601   AGATTCCACT ATGGACCACA TAGTATATAG ATGCATTTTA GAGTGTAGAT
 8651   TCACTCATTT TGCTTCGTAT GTAGTCCATA GTGAAATCTC TACAGAGACT
 8701   TATATTTAGG AACGGAGGGA GTACATAATT GATTTGTCTC ATCAGATTGC
 8751   TAGTGTTTTC TTGTGATAAA GATTGGCTGC CTCACCCATC ACCAGCTATT
 8801   TCCCAACTGT TACTTGAGCA GAATTTGCTG AAAACGTACC ATGTGGTACT
 8851   GTGGCGGCTT GTGAACTTTG ACAGTTATGT TGCAATTTTC TGTTCTTATT
 8901   TATTTGATTG CTTATGTTAC CGTTCATTTG CTCATTCCTT TCCGAGACCA
 8951   GCCAAAGTCA CGTGTTAGCT GTGTGATCTG TTATCTGAAT CTTGAGCAAA
 9001   TTTTATTAAT AGGCTAAAAT CCAACGAATT ATTTGCTTGA ATTTAAATAT
 9051   ACAGACGTAT AGTCACCTGG CTCTTTCTTA GATGATTACC ATAGTGCCTG
 9101   AAGGCTGAAA TAGTTTTGGT GTTTCTTGGA TGCCGCCTAA AGGAGTGATT
 9151   TTTATTGGAT AGATTCCTGG CCGAGTCTTC GTTACAACAT AACATTTTGG
 9201   AGATATGCTT AGTAACAGCT CTGGGAAGTT TGGTCACAAG TCTGCATCTA
 9251   CACGCTCCTT GAGGTTTTAT TATGGCGCCA TCTTTGTAAC TAGTGGCACC
 9301   TGTAAGGAAA CACATTCAAA AGGAAACGGT CACATCATTC TAATCAGGAC
 9351   CACCATACTA AGAGCAAGAT TCTGTTCCAA TTTTATGAGT TTTTGGGACT
 9401   CCAAAGGGAA CAAAAGTGTC TCATATTGTG CTTATAACTA CAGTTGTTTT
 9451   TATACCAGTG TAGTTTTATT CCAGGACAGT TGATACTTGG TACTGTGCTG
 9501   TAAATTATTT ATCCGACATA GAACAGCATA AACATATCAA GCTCTCTTTG
 9551   TGCAGGATAT GTATGATTTC ATGGCTCTGG ATAGGCTTCA ACTCTTCGCA
 9601   TTGATCGTGG CATAGCATTA CATAAAATGA TCAGGCTTGT CACCATGGGT
 9651   TTAGGTGGTG AAGGCTATCT TAACTTCATG GGAAATGAGT TTGGGCATCC
 9701   TGGTCAGTCT TTACAACATT ATTGCATTCT GCATGATTGT GATTTACTGT
 9751   AATTTGAACC ATGCTTTTCT TTCACATTGT ATGTATTATG TAATCTGTTG
 9801   CTTCCAAGGA GGAAGTTAAC TTCTATTTAC TTGGCAGAAT GGATAGATTT
 9851   TCCAAGAGGC CCACAAACTC TTCCAACCGG CAAAGTTCTc CCCTGGAAAT
 9901   AACAATAGTT ATGATAAATG CCGCCGTAGA TTTGATCTTG TAAGTTTTAG
 9951   CTGTGCTATT ACATTCCCTC ACTAGATCTT TATTGGCCAT TTATTTCTTG
10001   ATGAAATCAT AATGTTGTT  AGGAAGATC  AACATTGCTT TTGTAGTTTT
10051   GTAGACGTTA ACATAAGTAT GTGTTGAGAG TTGTTGATCA TTAAAAATAT
10101   CATGATTTTT TGCAGGGAGA TGCAGATTTT CTTAGATATC GTGGTATGCA
10151   AGAGTTCGAT CAGGCAATGC AGCATCTTGA GGAAAAATAT GGGGTATGTC
10201   ACTGGTTTGT CTTTGTTGCA TAACAAGTCA CAGTTTAACG TCAGTCTCTT
```

*Figure 2 (cont'd)*

```
10251  CAAGTGGTAA AAAAAGTGTA GAATTAATTC CTGTAATGAG ATGAAAACTG
10301  TGCAAAGGCG GAGCTGGAAT TGCTTTTCAC CAAAACTATT TTCTTAAGTG
10351  CTTGTGTATT GATACATATA CCAGCACTGA CAATGTAACT GCAGTTTATG
10401  ACATCTGAGC ACCAGTATGT TTCACGGAAA CATGAGGAAG ATAAGGTGAT
10451  CATCCTCnAA AAGAGGAGAT TTGGTATTTG TTTTCAACTT CCACTGGAGC
10501  AATAGCTTTT TTGACTACCG TGTTGGGTGT TCCAAGCCTG GGAAGTACAA
10551  GGTATGCTTG CCTTTTCATT GTCCACCCTT CACCAGTAGG GTTAGTGGGG
10601  GCTTCTACAA CTTTTAATTC CACATGGATA GAGTTTGTTG GTCGTGCAGC
10651  TATCAATATA AAGAATAGGG TAATTTGTAA AGAAAAGAAT TTGCTCGAGC
10701  TGTTGTAGCC ATAGGAAGGT TGTTCTTAAC AGCCCCGAAG CACATACCAT
10751  TCATTCATAT tATCTACTTA AGTGTTTGTT TCAATCTTTA TGCTCAGTTG
10801  GACTCGGTCT AATACTAGAA CTATTTTCCG AATCTACCCT AACCATCCTA
10851  GCAGTTTTAG AGCAGCCCCA TTTGGACAAT TGGCTGGGTT TTTGTTAGTT
10901  GTGACAGTTT CTGCTATTTC TTAATCAGGT GGCCTTGGAC TCTGACGATG
10951  CACTCTTTGG TGGATTCAGC AGGCTTGATC ATGATGTCGA CTACTTCACA
11001  ACCGTAAGTC TGGGCTCAAG CGTCACTTGA CTCGTCTTGA CTCAACTGCT
11051  TACAAATCTG AATCAACTTC CCAATTGCTG ATGCCCTTGC AGGAACATCC
11101  GCATGACAAC AGGCCGCGCT CTTTCTCGGT GTACACTCCG AGCAGAACTG
11151  CGGTCGTGTA TGCCCTTACA GAGTAAGAAC CAGCAGCGGC TTGTTACAAG
11201  GCAAAGAGAG AACTCCAGAG AGCTCGTGGA TCGTGAGCGA AGCGACGGGC
11251  AACGGCGCGA GGCTGCTCCA AGCGCCATGA CTGGGAGGGG ATCGTGCCTC
11301  TTCCCCAGAT GCCAGGAGGA GCAGATGGAT AGGTAGCTTG TTGGTGAGCG
11351  CTCGAAAGAA AATGGACGGG CCTGGGTGTT TGTTGTGCTG CACTGAACCC
11401  TCCTCCTATC TTGCACATTC CCGGTTGTTT TTGTACATAT AACTAATAAT
11451  TGCCCGTGCG CTCAACGTGA AAATCC
```

*Figure 2 (cont'd)*

DNA sequence of INTRON 5 PCR Fragments

```
                1                                                           50
D genome    ATCACTTACC GAGAATGGGC TCCT.GGAGC GCATGTATGT CTTT......
A genome    ATCACTTACC GAGAATGGGC TCCT.GGAGC GCATGTACGT CTTT......
B genome    ATCACTTACC GAGAATGGGC TCCT.GGAGC GCATGTAC.. ..........
262bp           ATCACTTACC GAGAATGGGC TCCTGNGAGC ANATGTATGT TCTTCTGACT 51                                                          100
D genome    ...TAAGTCT TAACAGACAC CTTCCAATTT ATTGTTAATG GT..CACTAT
A genome    ...TAAGTCT TAACAGACAC CTTCCAATTC ATTGTTAATG GTCACACTAT
B genome    ......GTCT TAACAGACAC CTTCTAATTT ATTGTTAATG GT..CACTAT
262bp       GTCTGATCGT TTACCTGACT ATACTAATTC TATCTTTCAA CTGCTTGTGA 101                                                         150
D genome    TCACCAACTA GCTTACTGGA CTTACAAATT AGCTTACTGA ATACTGACCA
A genome    TCACCAACTA GCTTACTGGA CTTACAACTT AGCTTACTGA ATACTGACCA
B genome    TCACCAACTA GCTTACTGGA CTTACAAAAT AGCTTACTGA ATACTGACCA
262bp       ATAATTAGTG CTCATCTGCT ATCCTAAGGT TGGGGATTTT GCACTTCCCA 151                                                         200
D genome    GTTA...... .......... ........CT ATAAATTTAT GATCTGGCTT
A genome    GTTG...... .......... ........CT CTAAATTTAT GATCTGGCTT
B genome    GTTA...... .......... ........CT CTAAATTTAT GATCTGGCTT
262bp       GATGAACAGC ATATTAAGTT GCACAACTAN CTTTATTTAA GAACTAACTC 201                                                         250
D genome    TTGCACCCTG TTACAGTCTG CAGCATTAGT AGGTGACTTC AACAATTGGG
A genome    TTGCACCCTG TTACAGTCTG CAGCATTAGT AGGTGACTTC AACAATTGGA
B genome    TTGGATCCTG TTACAGTCTG CAGCATTAGT AGGTGACTTC AACAATTGGA
262bp       TTGCTTCCAA TTGCAGTCTG CAACATTAGT TGGCGACTTC AACAATTGGA 251        262
D genome    ATCCAAATGC AG
A genome    ATCCAAATGC AG
B genome    ATCCAAATGC AG
262bp       ATCCAAATGC AG
```

*Figure 4*

Comparison of Universal 262 bp Sequence with the Wheat Branching Enzyme IIb Gene

```
FILE NAME       -5         4         14        24        34        44        54
262bp           ......ATCACTTACCGAGAATGGGCTCCTGNGAGCANATGTATGTTCTTCTGACTGTCT
                      ||||||||||||||||||||||||||| |||| ||||| |||||||| ||  |||
WBEIIB          GAAGGTATCACTTACCGAGAATGGGCTCCTGG-AGCAGATGTACGTTCTTCTAACCATCT
                2010      2019      2029      2039      2049      2059      2069

FILE NAME       55        64        74        84        94        104       114
262bp           GATCGTTTACCTGACTATACTAATTCTATCTTTCAACTGCTTGTGAATAATTAGTGCTCA
                ||||||||||||||||||||||||||||||||||||| |||||||||||||| |||||||
WBEIIB          GATCGTTTACCTGACTATACTAATTCTATCTTTCAACTAATTGTGAATAATTACTGCTCA
                2070      2079      2089      2099      2109      2119      2129

FILE NAME       115       124       134       144       154       164       174
262bp           TCTGCTATCCTAAGGTTGGGGATTTTGCACTTCCCAGATGAACAGCATATTAAGTTGCAC
                || |||||||||||||||||||||||||||||| ||||||||||||||||||||| ||||
WBEIIB          TCAGCTATCCTAAGGTTGGGGATTTTGCACCTCCCAGATGAACAGCATATTAAGTCGCAC
                2130      2139      2149      2159      2169      2179      2189

FILE NAME       175       184       194       204       214       224       234
262bp           AACTANCTTTATTTAAGAACTAACTCTTGCTTCCAATTGCAGTCTGCAACATTAGTTGGC
                ||||| | |||||| |||||||||||| ||||||||||||||||||||| |||||||||
WBEIIB          AACTAGCATTATT-AAGAACTAACTCCTGCTTCCAATTGCAGTCTGCAGCATTAGTTGGC
                2190      2199      2209      2219      2229      2239      2249

FILE NAME       235       244       254       264       274
262bp           GACTTCAACAATTGGAATCCAAATGCAG...............
                ||||||| ||||||| ||||||||||||
WBEIIB          GACTTCAACAATTGGGATCCAAATGCAGACCATATGAGCAAAG
                2250      2259      2269      2279      2289
```

*Figure 6*

Comparison of BARLEY BEIIB cDNA, WHEAT BEIIB cDNA, wheat BEIIa cDNA sequences with the wSBE II-DB1 gene

```
                         10         20         30         40         50         60         70         80         90
BARLEY BEIIB CDNA    603 TCGCAGCGCT GAAGGTATCA CTTACCGAGA ATGGGCTCCT GGAGCAGAT- ---------- ---------- ---------- ----------
                     692
WHEAT BEIIB CDNA CDNA 802 G********* ********** ********** ********** *********- ---------- ---------- ---------- ----------
---- 891
SBE9 CDNA            537 C****T**** ********** ********** ********** *****GC**- ---------- ---------- ---------- ----------
626
WHEAT BEIIB GENE    2000 AT******** ********** ********** ********** *********G TACGTTCTTC TAACCATCTG ATCGTTTACC TGACTATACT
2089

100        110        120        130        140        150        160        170        180
BARLEY BEIIB CDNA   693 ---------- ---------- ---------- ---------- ---------- ---------- ---------- ---------- ----------
782
WHEAT BEIIB CDNA    892 ---------- ---------- ---------- ---------- ---------- ---------- ---------- ---------- ----------
981
SBE9 CDNA           627 ---------- ---------- ---------- ---------- ---------- ---------- ---------- ---------- ----------
716
WHEAT BEIIB GENE   2090 AATTCTATCT TTCAACTAAT TGTGAATAAT TACTGCTCAT CAGCTATCCT AAGGTTGGGG ATTTTGCACC TCCAGATGA ACAGCATATT
2179

190        200        210        220        230        240        250        260        270
BARLEY BEIIB CDNA CDNA 783 ---------- ---------- ---------- ---------- ---------- ---------- TCTGCAGCAT TAGTTGCGA CTTCAACAAT
TGGGATCCAA 872
WHEAT BEIIB CDNA    982 ---------- ---------- ---------- ---------- ---------- ---------- ********** ********** **********
1071
SBE9 CDNA           717 ---------- ---------- ---------- ---------- ---------- ---------- **AT AT *A****G*
806
WHEAT BEIIB GENE   2180 AAGTCGCACA ACTAGCATTA TTAAGAACTA ACTCCTGCTT CCAATTGCAG ********** ********** ********** **********
2269

280        290        300        310        320        330        340        350        360
BARLEY BEIIB CDNA   873 CTCCAGACCA TATGAGCAAA ---------- ---------- ---------- ---------- ---------- ---------- ----------
962
WHEAT BEIIB CDNA   1072 A******** ********** ---------- ---------- ---------- ---------- ---------- ---------- ----------
1161
SBE9 CDNA           807 A*****TAC *****C**G* ---------- ---------- ---------- ---------- ---------- ---------- ----------
896
```

*Figure 7*

| | | 370 | 380 | 390 | 400 | 410 | 420 | 430 | 440 | 450 |
|---|---|---|---|---|---|---|---|---|---|---|
| WHEAT BEIIB GENE | 2270 | A********* | ********** | GTATGCATGT | AGTTTCACAA | ATATATCATA | TTTTCTTTGT | AGATTTTTT | TTTAGATCG | GCTTATCTAT |
| BARLEY BEIIB CDNA | 963 | ---------- | ---------- | ---------- | ---------- | ---------- | ---------- | ---------- | ---------- | ---------- |
| WHEAT BEIIB CDNA | 1162 | ---------- | ---------- | ---------- | ---------- | ---------- | ---------- | ---------- | ---------- | ---------- |
| SBE9 CDNA CDNA | 897 | ---------- | ---------- | ---------- | ---------- | ---------- | ---------- | ---------- | ---------- | ---------- |

| | | 460 | 470 | 480 | 490 | 500 | 510 | 520 | 530 | 540 |
|---|---|---|---|---|---|---|---|---|---|---|
| WHEAT BEIIB GENE | 2360 | TTAAATGTGG | TTGAATATAC | ACCTTATATG | TACGTTGAGC | TGTAAATATA | GTTGAAGTG | TTTAGGACTA | TTAAATTCAC | TGGACTCTAT |
| BARLEY BEIIB CDNA | 1053 | ---------- | ---------- | ---------- | ---------- | ---------- | ---------- | ---------- | ---------- | ---------- |
| WHEAT BEIIB CDNA | 1252 | ---------- | ---------- | ---------- | ---------- | ---------- | ---------- | ---------- | ---------- | ---------- |
| SBE9 CDNA | 987 | ---------- | ---------- | ---------- | ---------- | ---------- | ---------- | ---------- | ---------- | ---------- |

| | | 550 | 560 | 570 | 580 | 590 | 600 | 610 | 620 | 630 |
|---|---|---|---|---|---|---|---|---|---|---|
| WHEAT BEIIB GENE | 2450 | TCTTTCACTT | GCCTGTTGCA | CGAGCCCATT | ACTAGATATC | AATGTTGATG | ATGCTTTTGT | TGTATGAGGT | CGAAGTGAAA | CATGCATGT |
| BARLEY BEIIB CDNA | 1143 | ---------- | ---------- | ---------- | ---------- | ---------- | ---------- | ---------- | ---------- | ---------- |
| WHEAT BEIIB CDNA | 1342 | ---------- | ---------- | ---------- | ---------- | ---------- | ---------- | ---------- | ---------- | ---------- |
| SBE9 CDNA | 1077 | ---------- | ---------- | ---------- | ---------- | ---------- | ---------- | ---------- | ---------- | ---------- |

| | | 640 | 650 | 660 | 670 | 680 | 690 | 700 | 710 | 720 |
|---|---|---|---|---|---|---|---|---|---|---|
| WHEAT BEIIB GENE | 2540 | ACCCTTTTAT | ATAAGTAAGG | TTGCACATGT | ATTTTTATG | ATCTAAACAT | TATTACTGA | TTTGTTCTT | GCAAGACACT | AAGCAGTTTT |
| BARLEY BEIIB CDNA | 1233 | ---------- | ---------- | ---------- | ---------- | ---------- | ---------- | ---------- | ---------- | ---------- |
| WHEAT BEIIB CDNA | 1432 | ---------- | ---------- | ---------- | ---------- | ---------- | ---------- | ---------- | ---------- | ---------- |
| SBE9 CDNA | 1167 | ---------- | ---------- | ---------- | ---------- | ---------- | ---------- | ---------- | ---------- | ---------- |

| | | 730 | 740 | 750 | 760 | 770 | 780 | 790 | 800 | 810 |
|---|---|---|---|---|---|---|---|---|---|---|
| WHEAT BEIIB GENE | 2630 | ACATAATAAT | GGCGTTGGAG | CAGGCCGACT | GCACATCTGA | ACTGTAGCTC | CATGTGGTTG | ATATAGATTA | CAAATGCTCA | TATTCAATGT |

```
SBE9 CDNA        1617 --------- ---------- ---------- ---------- ---------- ---------- ---------- ---------- ---------- ----------
1706
WHEAT BEIIB GENE 3080 TCACGAACCT TCCCAATTGC TATTTCAAGC TGTCCTACTT ATTTGCTGCT GGCATCTTAT TTTTCTATTC TCTAACCAGT TATGAAATTC
3169

1180       1190       1200       1210       1220       1230
BARLEY BEIIB CDNA 1773 ---------- -------AG AAGTATGTAT TCAAGCATCC TCAACCTAAA CGACCAAA.. ......
WHEAT BEIIB CDNA  1972 ---------- ---------** ********** A********* ********** *****..... ......
SBE9 CDNA         1707 ---------- ---------** *********C* **C*A***** ********** ******G*GT CACT.
WHEAT BEIIB GENE  3170 CTTACATGCA TATGCAGG** ********** ********** ********** ******AT CATTG
```

*Figure 7 (cont'd)*

Partial Sequence of the A. tauschii Branching Enzyme IIb gene

```
   1 GGATCCGATC CGGCTGCGGC GGCGGCGACG GGATGGCTGC GCCGGCATTC GCAGTTTCCG
  61 CGGCGGGGCT GGCCCGGCCG TCGGCTCCTC GATCCGGCGG GGCAGAGCGG AGGGGGCGCG
 121 GGGTGGAGCT GCAGTCGCCA TCGCTGCTCT TCGGCCGCAA CAAGGGCACC CGTTCACCCC
 181 GTAATTATTT GCGCCACCTT TCTCACTCAC ATTCTCTCGT GTATTCTGTC GTGCTCGCCC
 241 TTCGCCGACG ACGCGTGCCG ATTCCGTATC GGGCTGCGGT GTTCAGCGAT CTTACGTCGG
 301 TTCCCTCCTG GTGTGGTGAT GTCTGTAGGT GCCGTCGGCG TCGGAGGTTC TGGATGGCGC
 361 GTGGTCATGC GCGCGGGGGG GCCGTCCGGG GAGGTGATGA TCCCTGACGG CGGTAGTGGC
 421 GGAACACCGC CTTCCATCGA CGGTCCCGTT CAGTTCGATT CTGATGATCT GAAGGTAGTT
 481 TTTTTTTTGC ATCGATCTGA AGGTACTTGA CATATACTAC TGTATTACCC TGAGTAAATA
 541 CTGCCACCAT ATTTTATGG TTCGCTTGAA ATACCTGTTT ACTTGCTACG GTTTTCACTT
 601 TCATTGAGAC GTCGGACGAA ATTCACTGAA TTCCTATAAT TTGGTAGACA CCGAAATATA
 661 TACTACTCCT TCCGTCCCAT AATATAAGAG CGTTTTGGC ACCTTATATT ATAGGGCGGA
 721 GGGAGTACCT TTTAGGTCAA AATATTGTGG TAGTTTCAAT TGTATACAAG AATTCAAATA
 781 TTTTTTTTAA AAAAAAATCA ACTAATTGGT TGAGTTTCAA GTGAAGCGTT TTGGTCCTTT
 841 GGCTGAGATG TAAACCGAAA TCACTGAAAT TCATAGTAGC CGAAACTTTA ATAGAACTGA
 901 AACTCAAAAT CTGCTATCCG GCGAAATTCT AAAGATTTGC TTATTTCACA CGTAGGTTGC
 961 AGTACACCCT CTTTCTAATT TATTGGGGAA GGGGTATTAT TATCTTGTTA GTACCTGCCT
1021 GCATGACAAT TGAAATCTAA GACAAAACAC CATATGCGAG GCCTACACAC GGTAGGTTGG
1081 TTTACAACTA TGTGTGCCAC AGTTCGTCTG AACTTTTTGT CCTTCACATC GTGTTAGGTT
1141 CCATTCATTG ATGATGAAAC AAGCCTACAG GATGGAGGTG AAGATAGTAT TTGGTCTTCA
1201 GAGACAAATC AGGTTAGTGA AGAAATTGAT GCTGAAGACA CGAGCAGAAT GGACAAAGAA
1261 TCATCTACGA GGGAGAAATT ACGCATTCTG CCACCACCGG GAAATGGACA GCAAATATAC
1321 GAGATTGACC CAACGCTCCG AGACTTTAAG TACCATCTTG AGTATCGGTA TGCTTCGCTT
1381 CTATTGTGTG CACTTTAAAA ACAATTTACA GTCTTTGATA AGATGTGAAT GGCTGCTTGC
1441 TGTGACACGA AACTCTTGAA GTTCGTAGTC ACTCTTGTGT GTTCATGGTT CTGAGGTAAC
1501 ATGGTAACCG AACAAAAATA GGAAAGTGGC AAGCACTGCA ATGTGAGCTA CTGATAACCA
1561 CCCATTGTAA TTGGGTACAC TGATTAATAT ATATGTCTTC ATGGGCTCTA TTTTTTTTCA
1621 ATATCTATGC CAATTGAACA ACAATGCTTT GTGGACGGGT GTTCTTTTAC CCTCTTCTTC
1681 TATCAATAGA TGATATGCAT ACTCATGCGT ATCCTACAAA AAATTGAACA ACAATGCCAC
1741 TTTCCCCCGT GTTGCTTTTG TAAGGATGAA ACACATATGT CCAGATCAAA CTATACTAGC
1801 AGTCTAACTG TGCCTTAATG GATCAAAAAC AGATATAGCC TATACAGGAG AATACGTTCA
1861 GACATTGATG AACACGAAGG AGGCATGGAT GTATTTTCCC GCGGTTACGA GAAGTTTGGA
1921 TTTATGCGCA GGTGAAATTT CTTGACTAAA TAACTATGTA TCTACCTTTT CTTTGTACTC
1981 TATCAACATT CCTCTTCCCA TGCAGCGCTG AAGGTATCAC TTACCGAGAA TGGGCTCCTG
2041 GAGCAGATGT ACGTTCTTCT AACCATCTGA TCGTTTACCT GACTATACTA ATTCTATCTT
2101 TCAACTAATT GTGAATAATT ACTGCTCATC AGCTATCCTA AGGTTGGGGA TTTTGCACCT
2161 CCCAGATGAA CAGCATATTA AGTCGCACAA CTAGCATTAT TAAGAACTAA CTCCTGCTTC
2221 CAATTGCAGT CTGCAGCATT AGTTGGCGAC TTCAACAATT GGGATCCAAA TGCAGACCAT
2281 ATGAGCAAAG TATGCATGTA GTTTCACAAA TATATCATAT TTTCTTTGTA GATTTTTTTT
2341 TTTAGATCGG CTTATCTATT TAAATGTGGT TGAATATACA CCTTATATGT ACGTTGAGCT
2401 GTAAATATAG TTGAAGTGT TTAGGAGTAT TAAATTCACT GGACTCTATT CTTTCACTTG
2461 CCTGTTGCAC GAGCCCATTA CTAGATATCA ATGTTGATGA TGCTTTTGTT GTATGAGGTC
2521 GAAGTGAAAC ATGCAGTGTTA CCCTTTTATA TAAGTAAGGT TGCACATGTA TTTTTTATGA
2581 TCTAAACATT ATTTACTGAT TTTGTTCTTG CAAGACATCA AGCAGTTTTA CATAATAATG
2641 GCGTTGGAGC AGGCCGACTG CACATCTGAA CTGTAGCTCC ATGTGGTTGA TATAGATTAC
2701 AAATGCTCAT ATTCAATGTA ACTGTTTTCA GAATGACCTT GGTGTTTGGG AGATTTTTCT
2761 GCCAAACAAT GCAGATGGTT CGCCACCAAT TCCTCACGGC TCACGGGTGA AGGTTGTTTT
2821 CTTCTCCTTG CCAACGTGT TAGGCTCAGG AACATGTCCT GTATTACTCA GAAGCTCTTT
2881 TGAACATCTA GGTGAGAATG GATACTCCAT CTGGGATAAA GGATTCAATT CCTGCTTGGA
2941 TCAAGTACTC CGTGCAGACT CCAGGAGATA TACCATACAA TGGAATATAT TATGATCCTC
3001 CCGAAGAGGT ATTTTACTTC ATCTTCTGTG CTTTTAGATT TCAGATATTT TTATTAGAAG
3061 AAAATTATGA TTTTTCCCT CACGAACCTT CCCAATTGCT ATTTCAAGCT GTCCTACTTA
3121 TTTGCTCTTG GCATCTTATT TTTCTATTCT CTAACCAGTT ATGAAATTCC TTACATGCAT
3181 ATGCAGGAGA AGTATGTATT CAAGCATCCT CAACCTAAAC GACCAAAATC ATTGCGGATA
3241 TATGAAACAC ATGTTGGCAT GAGTAGCCCG GTATTTCATC TTTACCATGT ATTCCATAAA
3301 TGAAGTTAGC TATATGCAGT TCAAATTTAT TTACAGGTTG TTACAATGGT ATTTTTGTGT
3361 TGGTGCCCTT CTTTCGTTTT ATAAGTAAAA AACTTATCAT AAATTTATTT GTTATGCCGC
3421 TTGGTTAATA CAATCTGAAA AATGTAACTG TGGACAATCT AGAACTAGAT AATACAAATC
3481 TGAAAAAACA TGCTGGAATA GTGTCATTTC AGTCAACTAG GATGTTTGA ATGCTCAAGA
3541 GAAGTACTAG TGTGTAGCAT CAAAAGCTGG TGTCCATTTG TTCAAATGTT TAATTAACAC
3601 TATAGTGAAA ACAAGTAATT GCACAAAGAA ACAAGTAATT GCCCAAGTTC ATATGTTTTT
```

*Figure 8*

```
3661 TCACTATATT ACATGTTTCA TCAACAATTT AATTAACCTC ATTCCTTACA AACATTTGTA
3721 TTTACATTTG TTCCTACATA TATAGTTATT TTATATATCA ACTTTATAAA TCATGACTGT
3781 TATAATTAAA ACCGATGGTA TATCAACGAT TGAGATAATT TGGCATATGT GGATGAATTT
3841 TGTGGCTTGT TATGCTCTTG TTTTAATAAC ATAATAAATA GATTATGCTT GTTGGTAGCC
3901 TTTTTACATT AACACATGGG CAATTACTTG TTTCTTTGTG CAACCAGGAA CCAAAGATCG
3961 AG
```

*Figure 8 (cont'd)*

Sequence of a wheat branching enzyme IIb cDNA

```
   1 ATGGTCGACC TGCAGGCGGC CGCGAATGCA CTAGNGATTT TGACACCAGA
  51 CCAACTGGTA ATGGTAGCGA CCGGCGCTCA GCTGGAATTC GCGGCCGCGT
 101 CGACCGTGGG TTTAAGCAGG AGACGAGGCG GGGTCAGTTG GGCAGTTAGG
 151 TTGGATCCGA TCCGGCTGCG GCGGCGGCGA CGGGATGGCT GCGCCGGCAT
 201 TCGCAGTTTC CGCGGCGGGG CTGGCCCGGC CGTCGGCTCC TCGATCCGGC
 251 GGGGCAGAGC GGAGGGGGCG CGGGGTGGAG CTGCAGTCGC CATCGCTGCT
 301 CTTCGGCCGC AACAAGGGCA CCCGTTCACC CCGTGCCGTC GGCGTCGGAG
 351 GTTCTGGATG GCGCGTGGTC ATGCGCGGG GGGGCCGTC CGGGGAGGTG
 401 ATGATCCCTG ACGGCGGTAG TGGCGGAACA CCGCCTTCCA TCGACGGTCC
 451 CGTTCAGTTC GATTCTGATG ATCTGAAGGT TCCATTCATT GATGATGAAA
 501 CAAGCCTACA GGATGGAGGT GAAGATAGTA TTTGGTCTTC AGAGACAAAT
 551 CAGGTTAGTG AAGAAATTGA TGCTGAAGAC ACGAGCAGAA TGGACAAAGA
 601 ATCATCTACG AGGGAGAAAT TACGCATTCT GCCACCACCG GGAAATGGAC
 651 AGCAAATATA CGAGATTGAC CCAACGCTCC GAGACTTTAA GTACCATCTT
 701 GAGTATCGAT ATAGCCTATA CAGGAGAATA CGTTCAGACA TTGATGAACA
 751 CGAAGGAGGC ATGGATGTAT TTTCCCGCGG TTACGAGAAG TTTGGATTTA
 801 TGCGCAGCGC TGAAGGTATC ACTTACCGAG AATGGGCTCC TGGAGCAGAT
 851 TCTGCAGCAT TAGTTGGCGA CTTCAACAAT TGGGATCCAA ATGCAGACCA
 901 TATGAGCAAA AATGACCTTG GTGTTTGGGA GATTTTTCTG CCAAACAATG
 951 CAGATGGTTC GCCACCAATT CCTCACGGCT CACGGGTGAA GGTGCGAATG
1001 GGTACTCCAT CTGGGACAAA GGATTCAATT CCTGCTTGGA TCAAGTACTC
1051 CGTGCAGACT CCAGGAGATA TACCATACAA TGGAATATAT TATGATCCTC
1101 CCGAAGAGGA GAAGTATGTA TTCAAGCATC CTCAACCTAA ACGACCAAAA
1151 TCATTGCGGA TATATGAAAC ACATGTTGGC ATGAGTAGCC CGGAACCAAA
1201 GATCAACACA TATGCAAACT TCAGGGATGA GGTGCTTCCA AGAATTAAAA
1251 GACTTGGATA CAATGCAGTG CAAATAATGG CAATCCAAGA GCACTCATAC
1301 TATGGAAGCT TTGGGTACCA TGTTACCAAT TTCTTTGCAC CAAGTAGCCG
1351 TTTTGGGTCC CCAGAAGATT TAAAATCTTT GATTGATAGA GCTCACGAGC
1401 TTGGCTTGGT TGTCCTCATG GATGTTGTTC ACAGTCACGC GTCAAATAAT
1451 ACCTTGGACG GGTTGAATGG TTTTGATGGC ACGGATACAC ATTACTTCCA
1501 TGGCGGTTCA CGGGGCCATC ACTGGATGTG GGATTCCCGT GTGTTTAACT
1551 ATGGAATAA GGAAGTTATA AGGTTTCTAC TTTCCAATGC AAGATGGTGG
1601 CTAGAGGAGT ATAAGTTTGA TGGTTTCCGA TTCGATGGCG CGACCTCCAT
1651 GATGTATACC CATCATGGAT ACAAGTAAC CTTTACAGGA AGCTACCATC
1701 AATATTTTGG CTTTGCCACT GATGTAGATG CGGTCGTTTA CTTGATGCTG
1751 ATGAATGATC TAATTCATGG GTTTTATCCT GAAGCCGTAA CTATCGGTGA
1801 AGATGTTAGT GGAATGCCTA CATTTGCCCT TCCTGTTCAA GTTGGTGGGG
1851 TTGGTTTTGA CTATCGCTTA CATATGGCTG TTGCCCGCAA ATGGATTGAA
1901 CTTCTCAAAG GAAACGATGA AGCTTGGGAG ATGGGTAATA TTGTGCACAC
1951 ACTAACAAAC AGAAGGTGGC TGGAAAAGTG TGTTACTTAT GCTGAAAGTC
2001 ACGATCAAGC ACTTGTTGGA GACAAGACTA TTGCATTCTG GTTGATGGAC
2051 AAGGATATGT ATGATTTCAT GGCGCTGAAC GGACCTTCGA CGCCTAATAT
2101 TGATCGTGGA ATAGCACTGC ATAAAATGAT TAGACTTATC ACAATGGGTC
2151 TAGGAGGAGA GGGTTATCTT AACTTTATGG GAAATGAGTT CGGGCATCCT
2201 GAATGGATAG ACTTTCCAAG AGGCCCACAA GTACTTCCAA GTGGTAAGTT
2251 CATCCCAGGA AACAACAACA GTTACGACAA ATGCCGTCGA AGATTTGACC
2301 TGGGTGATGC AGAATTTCTT AGGTATCATG GTATGCAGCA GTTTGATCAG
2351 GCAATGCAGC ATCTTGAGGA AAAATATGGT TTTATGACAT CAGACCACCA
2401 GTACGTATCT CGGAAACATG AGGAAGATAA GGTGATCGTG TTTGAAAAAG
2451 GGGACTTGGT ATTTGTGTTC AACTTCCACT GGAGTAGTAG CTATTTCGAC
2501 TACCGGGTCG GCTGTTTAAA GCCTGGGAAG TACAAGGTGG TCTTAGACTC
2551 GGACGCTGGA CTCTTTGGTG GATTTGGTAG GATCCATCAC ACTGCAGAGC
2601 ACTTCACTTC TGACTGCCAA CATGACAACA GGCCCCATTC ATTCTCAGTG
2651 TACACTCCTA GCAGAACCTG TGTTGTCTAT GCTCCAATGA ACTAACAGCA
2701 AAGTGCAGCA TACGCGTGCG CGCTGTTGTT GCTAGTAGCA AGAAAAATCG
2751 TATGGTCAAT ACAACCAGGT GCAAGGTTTA ATAAGGATTT TTGCTTCAAC
2801 GAGTCCTGGA TAGACAAGAC AACATGATGT TGTGCTGTGT GCTCCCAATC
2851 CCCAGGGCGT TGTGAAGAAA ACATGCTCAT CTGTGTTATT TTATGGATCA
2901 GCGACGAAAC CTCCCCCAAA TACCCCTTTT TTTTTTNAAA GGAGGATAGG
2951 CCCCCGGNCT TTGCNTNN
```

*Figure 9*

Alignment of Cereal Branching Enzyme Sequences

```
              1                                                            50
Y11282        --MATFAVSG ATLGVARPAG AGGGLLPRSG SERRGGVDLP SLLLRKKDS.
sbe9          --MATFAVSG ATLGVARPPA A......... .......... ..........
barley BEIIa  ---------- ---------- ---------- ---------- ----------
maize  BEIIa  ---------- ---------- ---------- -------DLP SVLFRRKDAF
rice   BEIV   --MASFAVSG ARLGVVRAGG GGGG..GGGP AARSGGVDLP SVLFRRKDSF
barley BEIIb  MAAPAFAV.. SAAGIARPSA R...RSSGAE PR........ .SLLFGRNKG
wheat  BEIIb  MAAPAFAV.. SAAGLARPSA P...RSGGAE RRGRGVELQS PSLLFGRNKG
maize  BEIIb  ---------- ---------- ---------- ---------- ----------
rice   BEIII  MAAPASAVPG SAAGLRAGAV RFPVPAGARS WRAAAELPTS RSLLSGR...

51                                                          100
Y11282        SR........ .....AVLSR AASPGKVLVP DGESDDLASP A........Q
sbe9          .......... .......... .......... .......... A........Q
barley BEIIa  ---------- ---------- ---------- ---------- ----------
maize  BEIIa  SR........ .....TVLSC AGAPGKVLVP GGGSDDLLSS AEPVVDT..Q
rice   BEIV   SR........ .....GVVSC AGAPGKVLVP GGGSDDLLSS AEPDVETQEQ
barley BEIIb  TRFPRAVGVG GSGWRVVMRA GGPSGEVMIP DGGSGGSGTP PSIEGSVQFE
wheat  BEIIb  TRSPRAVGVG GSGWRVVMRA GGPSGEVMIP DGGSG..GTP PSIDGPVQFD
maize  BEIIb  ---------- ---------- ----KAVMVP EGENDGL... ASRADSAQFQ
rice   BEIII  RFPGAVRVG  GSGGRVAVRA AGASGEVMIP EGESDGM... PVSAG.....

101                                                         150
Y11282        PEELQIPEDI EEQ....... .......... ......TAEV NMTGGTAEKL
sbe9          PEELQIPEDI EEQ....... .......... ......TAEV NMTGGTAEKL
barley BEIIa  ---------- -GE....... .......... ......MAEV NMTGGAAEKL
maize  BEIIa  PEELQIP... .......EAE LTVEKTSSSP TQTTSAVAEA SSGVEAEERP
rice   BEIV   PEESQIPDDN KVKPFEEEEE I......... ....PAVAEA SIKVVAEDKL
barley BEIIb  SDDLEVPFID D......... .......... ........EP SLHDGGEDTI
wheat  BEIIb  SDDLKVPFID D......... .......... ........ET SLQDGGEDSI
maize  BEIIb  SDELEVPDIS E......... .......... ........E. .TTCGA....
rice   BEIII  SDDLQLPALD D......... .......... ........EL STEVGAEVEI 151                                                         200
Y11282        ESSEPTQGIV ETITDGV... .........T KGVKELVVGE KPRVVPKPGD
sbe9          ESSEPTQGIV ETITDGV... .........T KGVKELVVGE KPRVVPKPGD
barley BEIIa  ESSEPTQGIA ETITDGV... .........T KGVKELVVGE KPQVVPKPGD
maize  BEIIa  ELSEVI.... .....GVGGT GGTKIDGAGI K.AKAPLVEE KPRVIPPPGD
rice   BEIV   ESSEVIQDIE ENVTEGV... .........I KDADEPTVED KPRVIPPPGD
barley BEIIb  RSSETYQVTE EIDAEGVSRM D......... ...KESSTVK KIRIVPQPGN
wheat  BEIIb  WSSETNQVSE EIDAEDTSRM D......... ...KESSTRE KLRILPPPGN
maize  BEIIb  ...GVA.... ..DAQALNRV .......... .......... ..RVVPPPSD
rice   BEIII  ESSGAS.... ..DVEGVKRV V......... ...EELAAEQ KPRVVPPTGD 201                                                         250
Y11282        GQKIYEIDPT LKDFRSHLDY RYSEYRRIRA AIDQHEGGLE AFSRGYEKLG
sbe9          GQKIYEIDPT LKDFRSHLDY RYSEYRRIRA AIDQHEGGLE AFSRGYEKLG
barley BEIIa  GQKIYEIDPT LKDFRSHLDY RYSEYKRIRA AIDQHEGGLE VFSRGYEKLG
maize  BEIIa  GQRIYEIDPM LEGFRGHLDY RYSEYKRLRA AIDQHEGGLD AFSRGYEKLG
rice   BEIV   GQKIYQIDPM LEGFRNHLDY RYSEYKRMRA AIDQHEGGLD AFSRGYEKLG
barley BEIIb  GQQIYDIDPM LRDFKYHLEY RYSLYRRIRS DIDEYDGGMD VFSRGYEKFG
wheat  BEIIb  GQQIYEIDPT LRDFKYHLEY RYSLYRRIRS DIDEHEGGMD VFSRGYEKFG
maize  BEIIb  GQKIFQIDPM LQGYKYHLEY RYSLYRRIRS DIDEHEGGLE AFSRSYEKFG
rice   BEIII  GQRIFQMDSM LNGYKYHLEY RYSLYRRLRS DIDQYEGGLE TFSRGYEKFG 251                                                         300
Y11282        FTRSAEGITY REWAPGAHSA ALVGDFNNWN PNADTMTRDD YGVWEIFLPN
sbe9          FTRSAEGITY REWAPGAHSA ALVGDFNNWN PNADTMTRDD YGVWEIFLPN
barley BEIIa  FTRSAKGITY REWAPGAHSA ALVGDFNNWN PNADTMTRDD YGVWEIFLPN
maize  BEIIa  FTRSAEGITY REWAPGAYSA ALVGDFNNWN PNADAMARNE YGVWEIFLPN
rice   BEIV   FTRSAEGITY REWAPGAQSA ALVGDFNNWN PNADTMTRNE YGVWEISLPN
barley BEIIb  FVRSAEGITY REWAPGADSA ALVGDFNNWD PTADHMSKND LGIWEIFLPN
wheat  BEIIb  FMRSAEGITY REWAPGADSA ALVGDFNNWD PNADHMSKND LGVWEIFLPN
maize  BEIIb  FNASAEGITY REWAPGAFSA ALVGDVNNWD PNADRMSKNE FGVWEIFLPN
rice   BEIII  FNHSAEGVTY REWAPGAHSA ALVGDFNNWN PNADRMSKNE FGVWEIFLPN
```

*Figure 10*

```
                 301                                                         350
     Y11282      NADGSPAIPH  GSRVKIRMDT  PSGVKDSISA  WIKFSVQAPG  EIPFNGIYYD
       sbe9      NADGSPAIPH  GSRVKIRMDT  PSGVKDSISA  WIKFSVQAPG  EIPFNGIYYD
 barley BEIIa    NADGSPAIPH  GSRVKIRMDT  PSGVKDSISA  WIKFSVQAPG  EIPFNGIYYD
  maize BEIIa    NADGSPAIPH  GSRVKIRMDT  PSGVKDSIPA  WIKFSVQAPG  EIPYNGIYYD
    rice BEIV    NADGSPAIPH  GSRVKIRMDT  PSGVKDSIPA  WIKFAVQAPG  EIPYNGIYYD
 barley BEIIb    NADGSPPIPH  GSRVKVRMDT  PSGTKDSIPA  WIKYSVQTPG  DIPYNGIYYD
  wheat BEIIb    NADGSPPIPH  GSRVKVRMGT  PSGTKDSIPA  WIKYSVQTPG  DIPYNGIYYD
  maize BEIIb    NADGTSPIPH  GSRVKVRMDT  PSGIKDSIPA  WIKYSVQAPG  EIPYDGIYYD
   rice BEIII    NADGSSPIPH  GSRVKVRMET  PSGIKDSIPA  WIKYSVQAAG  EIPYNGIYYD 351                                                         400
     Y11282      PPEEEKYVFQ  HPQPKRPESL  RIYESHIGMS  SPEPKINSYA  NFRDEVLPRI
       sbe9      PPEEEKYVFQ  HPQPKRPESL  RIYESHIGMS  SPEPKINSYA  NFRDEVLPRI
 barley BEIIa    PPEEEKYVFQ  HPQPKRPESL  RIYESHIGMS  SPEPKINSYA  NFRDEVLPRI
  maize BEIIa    PPEEEKYVFK  HPQPKRPKSL  RIYESHVGMS  SPEPKINTYA  NFRDEVLPRI
    rice BEIV    PPEEEKYVFQ  HPQPKRPNSL  RIYESHIGMS  SPEPKINTYA  NFRDEVLPRI
 barley BEIIb    PPEEEKYVFK  HPQPKRPKSL  RIYETHVGMS  SPEPKINTYA  NFRDEVLPRI
  wheat BEIIb    PPEEEKYVFK  HPQPKRPKSL  RIYETHVGMS  SPEPKINTYA  NFRDEVLPRI
  maize BEIIb    PPEEVKYVFR  HAQPKRPKSL  RIYETHVGMS  SPEPKINTYV  NFRDEVLPRI
   rice BEIII    PPEEEKYIFK  HPQPKRPKSL  RIYETHVGMS  STEPKINTYA  NFRDEVLPRI 401                                                         450
     Y11282      KRLGYNAVQI  MAIQEHSYYA  SFGYHVTNFF  APSSRFGTPE  DLKSLIDRAH
       sbe9      KRLGYNAVQI  MAIQEHSYYA  SFGYHVTNFF  APSSRFGTPE  DLKSLIDRAH
 barley BEIIa    KRLGYNAVQI  MAIQEHSYYA  SFGYHVTNFF  APSSRFGTPE  DLKSLIDRAH
  maize BEIIa    KKLGYNAVQI  MAIQEHSYYA  SFGYHVTNFF  APSSRFGTPE  DLKSLIDKAH
    rice BEIV    KKLGYNAVQI  MAIQEHSYYA  SFGYHVTNFF  APSSRFGTPE  DLKSLIDKAH
 barley BEIIb    KRLGYNAVQI  MAIQEHSYYG  SFGYHVTNFF  APSSRFGSPE  DLKSLIDRAH
  wheat BEIIb    KRLGYNAVQI  MAIQEHSYYG  SFGYHVTNFF  APSSRFGSPE  DLKSLIDRAH
  maize BEIIb    KKLGYNAVQI  MAIQEHSYYG  SFGYHVTNFF  APSSRFGTPE  DLKSLIDRAH
   rice BEIII    KKLGYNAVQI  MAIQEHAYYG  SFGYHVTNFF  APSSRFGTPE  DLKSLIDKAH 451                                                         500
     Y11282      ELGLLVLMDI  VHSHSSNNTL  DGLNGFDGTD  THYFHGGPRG  HHWMWDSRLF
       sbe9      ELGLLVLMDI  VHSHSSNNTL  DGLNGFDGTD  THYFHGGPRG  HHWMWDSRLF
 barley BEIIa    ELGLLVLMDI  VHSHSSNNTL  DGLNGFDGTD  THYFHGGPRG  HHWMWDSRLF
  maize BEIIa    ELGLLVLMDI  VHSHSSNNTL  DGLNGFDGTD  THYFHGGPRG  HHWMWDSRLF
    rice BEIV    ELGLLVLMDI  VHSHASNNTL  DGLNGFDGTD  THYFHGGPRG  HHWMWDSRLF
 barley BEIIb    ELGLLVLMDV  VHSHASSNTL  DGLNGFDGTD  THYFHGGSRG  HHWMWDSRVF
  wheat BEIIb    ELGLVVLMDV  VHSHASNNTL  DGLNGFDGTD  THYFHGGSRG  HHWMWDSRVF
  maize BEIIb    ELGLLVLMDV  VHSHASSNTL  DGLNGFDGTD  THYFHSGPRG  HHWMWDSRLF
   rice BEIII    ELGLVVLMDV  VHSHASNNTL  DGLNGFDGTD  THYFHSGSRG  HHWMWDSRLF 501                                                         550
     Y11282      NYGSWEVLRF  LLSNARWWLE  EYKFDGFRFD  GVTSMMYTHH  GLQMTFTGNY
       sbe9      NYGSWEVLRF  LLSNARWWLE  EYKFDGFRFD  GVTSMMYTHH  GLQMTFTGNY
 barley BEIIa    NYGSWEVLRF  LLSNARWWLE  EYKFDGFRFD  GVTSMMYTHH  GLQMTFTGNY
  maize BEIIa    NYGSWEVLRF  LLSNARWWLE  EYKFDGFRFD  GVTSMMYTHH  GLQVTFTGNY
    rice BEIV    NYGSWEVLRY  LLSNARWWLE  EYKFDGFRFD  GVTSMMYTHH  GLQVAFTGNY
 barley BEIIb    NYGNKEVIRF  LLSNARWWLE  EYKFDGFRFD  GATSMMYTHH  GLQVTFTGSY
  wheat BEIIb    NYGNKEVIRF  LLSNARWWLE  EYKFDGFRFD  GATSMMYTHH  GLQVTFTGSY
  maize BEIIb    NYGNWEVLRF  LLSNARWWLE  EYKFDGFRFD  GVTSMMYTHH  GLQVTFTGNF
   rice BEIII    NYGNWEVLRF  LLSNARWWLE  EYKFDGFRFD  GVTSMMYTHH  GLQVAFTGNY 551                                                         600
     Y11282      GEYFGFATDV  DAVVYLMLVN  DLIHGLHPDA  VSIGEDVSGM  PTFCIPVPDG
       sbe9      GEYFGFATDV  DAVVYLMLVN  DLIHGLHPDA  VSIGEDVSGM  PTFCIPVPDG
 barley BEIIa    GEYFGFATDV  DAVVYLMLVN  DLIHGLYPDA  VSIGEDVSGM  PTFCIPVPDG
  maize BEIIa    GEYFGFATDV  DAVVYLMLVN  DLIRGLYPEA  VSIGEDVSGM  PTFCIPVQDG
    rice BEIV    GEYFGFATDV  DAVVYLMLVN  DLIHGLYPEA  VAIGEDVSGM  PTFCIPVQDG
 barley BEIIb    HEYFGFATDV  DAVVYLMLVN  DLIHALYPEA  VTIGEDVSGM  PTFALPVQVG
  wheat BEIIb    HEYFGFATDV  DAVVYLMLMN  DLIHGFYPEA  VTIGEDVSGM  PTFALPVQVG
  maize BEIIb    NEYFGFATDV  DAVVYLMLVN  DLIHGLYPEA  VTIGEDVSGM  PTFALPVHDG
   rice BEIII    SEYFGFATDA  DAVVYLMLVN  DLIHGLYPEA  ITIGEDVSGM  PTFALPVQDG
```

*Figure 10 (cont'd)*

```
                  601                                                         650
     Y11282       GVGLDYRLHM AVADKWIELL KQSDESWKMG DIVHTLTNRR WLEKCVTYAE
       sbe9       GVGFDYRLHM AVADKWIELL KQSDESWKMG DIVHTLTNRR WLEKCVTYAE
barley BEIIa      GVGFDYRLHM AVADKWIELL KQSDESWKMG DIVHTLTNRR WLEKCVTYAE
 maize BEIIa      GVGFDYRLHM AVPDKWIELL KQSDEYWEMG DIVHTLTNRR WLEKCVTYCE
   rice BEIV      GVGFDYRLHM AVPDKWIELL KQSDEYWKMG DIVHTLTNRR WSEKCVTYAE
barley BEIIb      GVGFDYRLHM AVADKWIELL KGSDEGWEMG NIVHTLTNRR WLEKCVTYAE
 wheat BEIIb      GVGFDYRLHM AVARKWIELL KGNDEAWEMG NIVHTLTNRR WLEKCVTYAE
 maize BEIIb      GVGFDYRMHM AVADKWIDLL KQSDETWKMG DIVHTLTNRR WLEKCVTYAE
  rice BEIII      GVGFDYRLHM AVPDKWIELL KQSDESWKMG DIVHTLTNRR WSEKCVTYAE 651                                                         700
     Y11282       SHDQALVGDK TIAFWLMDKD MYDFMALDRP STPRIDRGIA LHKMIRLVTM
       sbe9       SHDQALVGDK TIAFWLMDKD MYDFMALDRP STPRIDRGIA LHKMIRLVTM
barley BEIIa      SHDQALVGDK TIAFWLMDKD MYDFMALDRP STPRIDRGIA LHKMIRLVTM
 maize BEIIa      SHDQALVGDK TIAFWLMDKD MYDFMALDRP STPRIDRGIA LHKMIRLVTM
   rice BEIV      SHDQALVGDK TIAFWLMDKD MYDFMALDRP STPRIDRGIA LHKMIRLVTM
barley BEIIb      SHDQALVGDK TIAFWLMDKD MYDFMALNGP STPNIDRGIA LHKMIRLITM
 wheat BEIIb      SHDQALVGDK TIAFWLMDKD MYDFMALNGP STPNIDRGIA LHKMIRLITM
 maize BEIIb      SHDQALVGDK TIAFWLMDKD MYDFMALDRP STPTIDRGIA LHKMIRLITM
  rice BEIII      SHDQALVGDK TIAFWLMDKD MYDFMALDRP ATPSIDRGIA LHKMIRLITM 701                                                         750
     Y11282       GLGGEGYLNF MGNEFGHPEW IDFPRGPQTL PTGKVLPGNN NSYDKCRRRF
       sbe9       GLGGEGYLNF MGNEFGHPEW IDFPRGPQTL PTGKVLPGNN NSYDKCRRRF
barley BEIIa      GLGGEGYLNF MGNEFGHPEW IDFPRGPQTL PTGKVLPGNN NSYDKCRRRF
 maize BEIIa      GLGGEGYLNF MGNEFGHPEW IDFPRGPQSL PNGSVIPGNN NSFDKCRRRF
   rice BEIV      GLGGEGYLNF MGNEFGHPEW IDFPRGPQSL PNGSVLPGNN YSFDKCRRRF
barley BEIIb      ALGGEGYLNF MGNEFGHPEW IDFPRGPQVL PTGKFIPGNN NSYDKCRRRF
 wheat BEIIb      GLGGEGYLNF MGNEFGHPEW IDFPRGPQVL PSGKFIPGNN NSYDKCRRRF
 maize BEIIb      GLGGEGYLNF MGNEFGHPEW IDFPRGPQRL PSGKFIPGNN NSYDKCRRRF
  rice BEIII      GLGGEGYLNF MGNEFGHPEW IDFPRAPQVL PNGKFIPGNN NSYDKCRRRF 751                                                         800
     Y11282       DLGDADFLRY HGMQEFDQAM QHLEEKYGFM TSEHQYVSRK HEEDKVIIFE
       sbe9       DLGDADFLRY HGMQEFDQAM QHLEEKYGFM TSEHQYVSRK HEEDKVIIFE
barley BEIIa      DLGDADFLRY RGMQEFDQAM QHLEEKYGFM TSEHQYVSRK HEEDKVIIFE
 maize BEIIa      DLGDADYLRY RGMQEFDQAM QHLEGKYEFM TSDHSYVSRK HEEDKVIIFE
   rice BEIV      DLGDADYLRY HGMQEFDQAM QHLEEKYGFM TSEHQYISRK HEEDKVIIFE
barley BEIIb      DLGDAEFLRY HGMQQFDQAM QHLEEKYGFM TSDHQYVSRK HEEDKVIVFE
 wheat BEIIb      DLGDAEFLRY HGMQQFDQAM QHLEEKYGFM TSDHQYVSRK HEEDKVIVFE
 maize BEIIb      DLGDADYLRY HGMQEFDQAM QHLEQKYEFM TSDHQYISRK HEEDKVIVFE
  rice BEIII      DLGDADYLRY RGMLEFDRAM QSLEEKYGFM TSDHQYISRK HEEDKMIIFE 801                                                         850
     Y11282       RGDLVFVFNF HWSNSFFDYR VGCSRPGKYK VALDSDDALF GGFSRLDHDV
       sbe9       RGDLVFVFNF HWSNSFFDYR VGCSRPGKYK VALDSDDALF GGFSRLDHDV
barley BEIIa      RGDLVFVFNF HWSNSKKDYR VGCSKPGKYK VALDSDDALF GGFSRLDHDV
 maize BEIIa      RGDLVFVFNF HWSNSYFDYR VGCFKPGKYK IVLDSDDGLF GGFSRLDHDA
   rice BEIV      RGDLVFVFNF HWSNSYFDYR VGCLKPGKYK IVLDSDDGLF GGFSRLDHDA
barley BEIIb      KGDLVFVFNF HWSNSYFDYR VGCLKPGKYK VVLDSDAGLF GGFGRIHHTG
 wheat BEIIb      KGDLVFVFNF HWSSSYFDYR VGCLKPGKYK VVLDSDAGLF GGFGRIHHTA
 maize BEIIb      KGDLVFVFNF HCNNSYFDYR IGCRKPGVYK VVLDSDAGLF GGFSRIHHAA
  rice BEIII      KGDLVFVFNF HWSNSYFDYR VGCLKPGKYK VVLDSDAGLF GGFGRIHHTA 851                       887
     Y11282       DYFTTEHPHD NRPRSFSVYT PSRTAVVYAL TE*-----
       sbe9       DYFTTEHPHD NRPRSFSVYT PSRTAVVYAL TE*-----
barley BEIIa      DYFTTEHPHD NRPRSFSVYT PSRTAVVYAL TE*-----
 maize BEIIa      EYFTADWPHD NRPCSFSVYA PSRTAVVYAP AGAEDE*
   rice BEIV      EYFTADWPHD NRPCSFSVYT PSRTAVVYAL ..TED*--
barley BEIIb      EHFTNGCQHD NRPHSFSVYT PSRTCVVYAP MN*-----
 wheat BEIIb      EHFTSDCQHD NRPHSFSVYT PSRTCVVYAP MN*-----
 maize BEIIb      EHFTADCSHD NRPYSFSVYT PSRTCVVYAP VE*-----
  rice BEIII      EHFTADCSHD NRPYSFSVYS PSRTCVVYAP AE*-----
```

*Figure 10 (cont'd)*

(A)
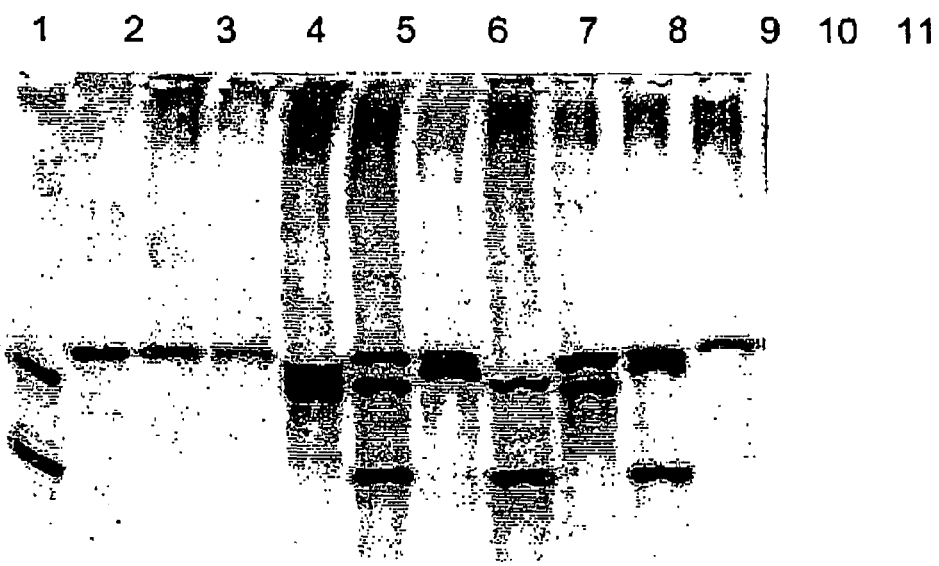
(B)
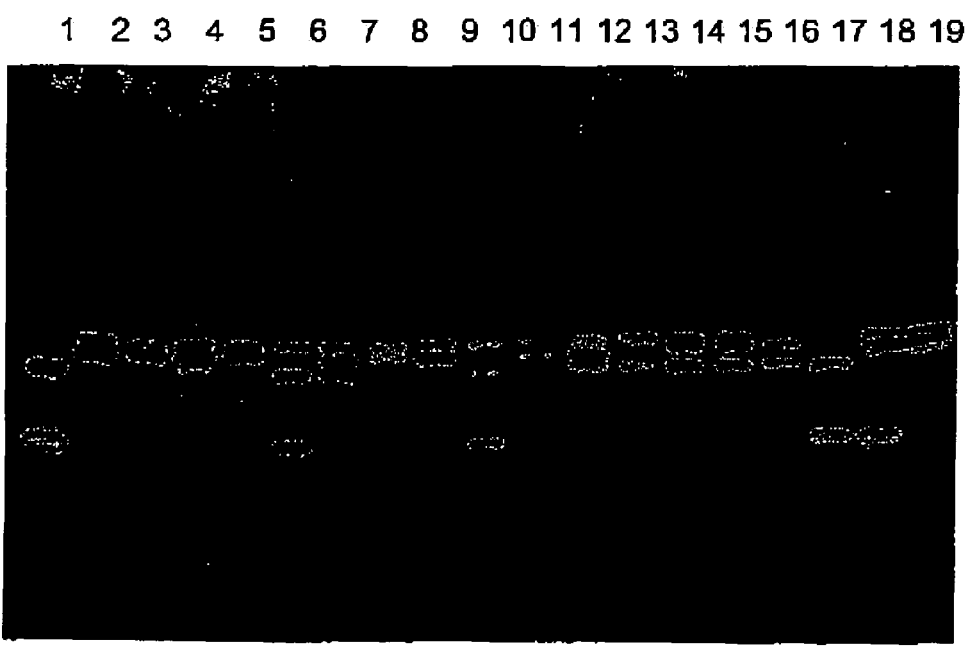
Figure 16

(A)
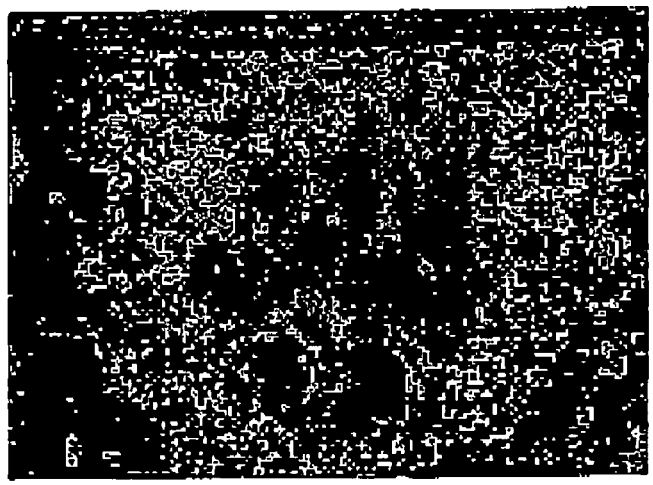
← 88 kD (U)
← 88 kD (L)
(B)
← 88 kD (U)
← 88 kD (L)
3KLH  R6
*Figure 17*

```
                            10        20        30        40        50        60
                             .         .         .         .         .         .
exon 1/2 A/B*   TGGCGGCGGCGACGGGATGGCTGCGCCGGCATTCGCAGTTTCCGCGGCGGGGCTGGCCC
exon 1/2 A/B    T----GCGGCGACGGGATGGCTGCGCCGGCATTCGCAGTTTCCGCGGCGGGGCTGGCCC
exon 1/2 1 D    CGGCGGCGGCGACGGGATGGCTGCGCCGGCATTCGCAGTTTCCGCGGCGGGGCTGGCCC exon 1/2 A/B    GGCCGTCGGCTCCTCGATCCGGCGGGGCAGAGCGGAGGGGGCGCGGGGTGGAGCTGCAGT
exon 1/2 A/B    GGCCGTCGGCTCCTCGATCCGGCGGGGCAGAGCGGAGGGGGCGCGGGGTGGAGCTGCAGT
exon 1/2 D      GGCCGTCGGCTCCTCGATCCGGCGGGGCAGAGCGGAGGGGGCGCGGGGTGGAGCTGCAGT exon 1/2 A/B    CGCCATCGCTGCTCTTCGGCCGCAACAAGGGCACCCGTTCACCCC---------------
exon 1/2 A/B    CGCCATCGCTGCTCTTCGGCCGCAACAAGGGCACCCGTTCACCCC---------------
exon 1/2 D      CGCCATCGCTGCTCTTCGGCCGCAACAAGGGCACCCGTTCACCCCGTAATTATTTGCGCC exon 1/2 A/B    ------------------------------------------------------------
exon 1/2 A/B    ------------------------------------------------------------
exon 1/2 D      ACCTTTCTCACTCACATTCTCTCGTGTATTCTGTCGTGCTCGCCCTTCGCCGACGACGC exon 1/2 A/B    ------------------------------------------------------------
exon 1/2 A/B    ------------------------------------------------------------
exon 1/2 D      GTGCCGATTCCGTATCGGGCTGCGGTGTTCAGCGATCTTACGTCGGTTCCCTCCTGGTGT exon 1/2 A/B    --------------GTGCCGTCGGCGTCGGAGGTTCTGGATGGCGCGTGGTCATGCGCGC
exon 1/2 A/B    --------------GTGCCGTCGGCGTCGGAGGTTCTGGATGGCGCGTGGTCATGCGCGC
exon 1/2 D      GGTGATGTCTGTAGGTGCCGTCGGCGTCGGAGGTTCTGGATGGCGCGTGGTCATGCGCGC exon 1/2 A/B    GGGGGGGCCGTCCGGGGAGGTGATGATCCCTGACGGCG
exon 1/2 A/B    GGGGGGGCCGTCCGGGGAGGTGATGATCCCTGACGGCG
exon 1/2 D      GGGGGGGCCGTCCGGGGAGGTGATGATCCCTGACGGCG
```

*Figure 21*

| | 10 | 20 | 30 | 40 | 50 | 60 | 70 | 80 | 90 | |
|---|---|---|---|---|---|---|---|---|---|---|
| SBE2_AL.DNA | 1 TTCTGCCACC | ACCGGGAAAT | GGACAGCAAA | TATACGAGAT | TGACCCAACG | CTCCGAGACT | TTAAGTACCA | TCTTGAGTAT | CGGTATGCTT | 90 |
| SBE2_B.DNA | 1 ---------- | ---------- | ---------- | ---------- | ---------- | ---------- | ---------- | ---------- | ----GCTT | 90 |
| SBE2_DL.DNA | 1 TTCTGCCACC | ACCGGGAAAT | GGACAGCAAA | TATACGAGAT | TGACCCAACG | CTCCGAGACT | TTAAGTACCA | TCTTGAGTAT | CGGTATGCTT | 90 |
| | 100 | 110 | 120 | 130 | 140 | 150 | 160 | 170 | 180 | |
| SBE2_AL.DNA | 91 CGCTTCTATT | GTGTGCACTT | TAAACTTTTAA | ATACAATTTA | CAGTCTTTGA | TAAGATGTGA | ATGGCTGCTT | GCTGTGACAC | AAAACTCTTG | 180 |
| SBE2_B.DNA | 91 CGCTTCTATT | GTGTGCACTT | TAAA------ | -AACAATTTA | CAGTCTTTGA | TAAGATGTGA | ATGGCTGCTT | GCTGTGACAC | AAAACTCTTG | 180 |
| SBE2_DL.DNA | 91 CGCTTCTATT | GTGTGCACTT | TAAA------ | -AACAATTTA | CAGTCTTTGA | TAAGATGTGA | ATGGCTGCTT | GCTGTGACAC | GAAACTCTTG | 180 |
| | 190 | 200 | 210 | 220 | 230 | 240 | 250 | 260 | 270 | |
| SBE2_AL.DNA | 181 AAGTTCGTAG | TCACTCTTGT | GTGTTCATGG | CTCTGAGGTG | ACATGGTAAC | CGAACAAAAA | TAGGAAAGTG | GCAAGAACTG | CAATGTGAGC | 270 |
| SBE2_B.DNA | 181 AAGTTCGTAG | TCACTCTTGT | GTGTTCATGG | CTCTGAGGTG | ACATGGTAAC | CGAACAAAAA | TAGGAAAGTG | GCAAGAACTG | CAATGTGAGC | 270 |
| SBE2_DL.DNA | 181 AAGTTCGTAG | TCACTCTTGT | GTGTTCATGG | TTCTGAGGTA | ACATGGTAAC | CGAACAAAAA | TAGGAAAGTG | GCAAGCACTG | CAATGTGAGC | 270 |
| | 280 | 290 | 300 | 310 | 320 | 330 | 340 | 350 | 360 | |
| SBE2_AL.DNA | 271 TACCGATAAG | CACCCATTGT | AATTGGGTAC | ACTGATTAAT | ATA--TGTCT | TGATGGGTTC | TATGTTTTTT | CAGTATCTAT | GCCAATTGAA | 360 |
| SBE2_B.DNA | 271 TACCGATAAG | CACCCATTGT | AATTGGGTAC | ACTGATTAAT | ATA--TGTCT | TGATGGGTTC | TATGTTTTTT | CAGTATCTAT | GCCAATTGAA | 360 |
| SBE2_DL.DNA | 271 TACTGATAAC | CACCCATTGT | AATTGGGTAC | ACTGATTAAT | ATATATGTCT | TCATGGGCTC | TATTTTTTTT | CAATATCTAT | GCCAATTGAA | 360 |
| | 370 | 380 | 390 | 400 | 410 | 420 | 430 | 440 | 450 | |
| SBE2_AL.DNA | 361 CAACAATGC- | ---------- | ---------- | ---------- | ---------- | ---------- | ---------- | ---------- | ---------- | 450 |
| SBE2_B.DNA | 361 CAACAATGC- | ---------- | ---------- | ---------- | ---------- | ---------- | ---------- | ---------- | ---------- | 450 |
| SBE2_DL.DNA | 361 CAACAATGCT | TTGTGGACGG | GTGTTCTTTT | ACCCTCTCTTCT | TCTATCAATA | GATGATATGC | ATACTCATGC | GTATCCTACA | AAAAATTGAA | 450 |
| | 460 | 470 | 480 | 490 | 500 | 510 | 520 | 530 | 540 | |
| SBE2_AL.DNA | 451 ----CACTT | CATTTCCCCT | GTGTTGCTTT | TGTAAGGATG | AAACCCATAT | GTCCAGATCA | AACTGTACTA | GCAGTCTCAC | TGTGCCTTAA | 540 |
| SBE2_B.DNA | 451 ----CACTT | CATTTCCCCT | GTGTTGCTTT | TGTAAGGATG | AAACACATAT | GTCCAGATCA | AACTATACTA | GCAGTC.... | .......... | 540 |
| SBE2_DL.DNA | 451 CAACAATGCC | ACTTTCCCCC | GTGTTGCTTT | TGTAAGGATG | AAACACATAT | GTCCAGATCA | AACTATACTA | GCAGTCTAAC | TGTGCCTTAA | 540 |
| | 550 | 560 | 570 | 580 | 590 | 600 | 610 | 620 | 630 | |
| SBE2_AL.DNA | 541 TGGATCAAAA | ACAGATACAG | CCTATATAGG | AGAATACGTT | CAGACATTGA | TGAACACG.. | .......... | .......... | .......... | 630 |
| SBE2_B.DNA | 541 .......... | .......... | .......... | .......... | .......... | .......... | .......... | .......... | .......... | 630 |
| SBE2_DL.DNA | 541 TGGATCAAAA | ACAGATATAG | CCTATACAGG | AGAATACGTT | CAGACATTGA | TGAACACG.. | .......... | .......... | .......... | 630 |

*Figure 22*

Duplex Construct

STARCH BRANCHING ENZYME

This invention relates to a new starch branching enzyme, and to the gene encoding the enzyme. In particular, the invention relates to a new starch branching enzyme type II from wheat. The invention also relates to a novel method for identification of such branching enzyme type II proteins, which is useful for screening wheat germplasm for null or altered alleles of wheat branching enzyme IIb. The novel gene, protein and methods of the invention are useful in production of wheat plants which produce grain with novel properties for food and industrial applications, for example wheat grain containing high amylose or low amylopectin starch.

BACKGROUND OF THE INVENTION

In plants, two classes of genes encode starch branching enzymes, known respectively as BEI, and BEII. In the monocotyledonous cereals, there is strong evidence demonstrating that the BEII class contains two independent types of genes, known in maize as BEIIa and BEIIb (Gao et al., 1996; Fisher et al., 1996). In barley, two types of genes have been reported, and shown to be differentially expressed (Sun et al., 1998), An additional class of branching enzyme (50/51 kD) from barley has also been described (Sun et al., 1996).

In dicotyledonous plants, loss of BEII activity through either mutation (Bhattacharyya et al., 1990) or gene suppression technologies gives rise to starches containing high amylose levels (Safford, 1998, Jobling 1999).

In monocotyledonous plants, mutations giving rise to high amylose contents are known in maize, rice and barley. In neither rice (Mizuno et al., 1993) nor barley (Schondelmaier et al., 1992) have the known high amylose phenotypes been associated with the BEIIa or BEIIb mutations respectively. However, in maize it is firmly established that the high amylose phenotype is associated with down regulation of the BEIIb gene (Boyer et al., 1980; Boyer and Preiss, 1981, Fisher et al, 1996).

The impact of down-regulation of BEI has been investigated through antisense inhibition in potato tuber; the down-regulation has been found to alter the properties of the starch, but not its gross structural features, such as the amylose content (Filpse et al., 1996). In wheat, antisense down-regulation of BEI activity has small but significant effects on starch structure (Baga et al, 1999). The branching enzyme I gene from maize has been cloned (Kim et al., 1998), but mutants affecting branching enzyme I activity in maize are not known.

No mutations specifically reducing BEIIa activity have been reported, and no gene suppression experiments in plants have succeeded in reducing BEIIa activity, although the du1 mutation in maize is known to reduce the expression of both BEIIa and starch synthase III. However, the du1 mutation is now known to be due to mutation of the structural gene for starch synthase III (Gao 1998, Cao 1999).

In our previous patent application No. PCT/AU98/00743 (WO99/14314), we have described the structure of a BEII gene from wheat, which we have subsequently designated the BEIIa gene.

In the present application we describe the isolation of a second BEII gene from wheat, which we have designated the BEIIb gene, and discuss the uses to which this gene sequence can be applied. We have surprisingly found that in wheat the expression level of the various branching enzymes is very different to that in maize and barley. In this specification we show that BEIIb in wheat is expressed at low levels in the soluble fraction of the wheat endosperm, and is predominantly found within the starch granule. This indicates that there are important differences in the regulation of gene expression in wheat compared to other cereals, suggesting that the manipulation of the amylose to amylopectin ratio in wheat will involve the manipulation of more than just the BEIIb gene.

We have also surprisingly found that the BEIIa and BEIIb gene structures are highly conserved with respect to exon size and position, allowing us to prepare DNA-based diagnostics which they can distinguish not only the BEIIa and BEIIb classes of genes, but also the forms of these genes encoded on the A, B and D genomes of wheat, and to identify the BEIIb proteins expressed by the wheat A, B and D genomes, providing an essential tool for the screening of wheat germplasm for null or altered alleles of wheat branching enzyme IIa.

SUMMARY OF THE INVENTION

In a first aspect, the invention provides an isolated nucleic acid molecule encoding wheat starch branching enzyme IIb (BEIIb).

Preferably the nucleic acid sequence is a DNA sequence, and may be genomic DNA or cDNA.

Preferably the nucleic acid molecule has the sequence depicted in FIG. 8 (SEQ ID NO:5), FIG. 9 (SEQ ID NO:6), or SEQ ID NO:10. It will be clearly understood that the invention also encompasses nucleic acid molecules capable of hybridising to these sequences under at least low stringency hybridization conditions, or a nucleic acid molecule with at least 70% sequence identity to at least one of these sequences. Methods for assessing ability to hybridize and % sequence identity are well known in the art. Even more preferably the nucleic acid molecule is capable of hybridizing thereto under high stringency conditions, or has at least 80%, most preferably at least 90% sequence identity. A nucleic acid molecule having at least 70%, preferably at least 90%, more preferably at least 95% sequence identity to one or more of these sequences is also within the scope of the invention.

Biologically-active untranslated control sequences of genomic DNA are also within the scope of the invention. Thus the invention also provides the promoter of BEIIb.

In a second aspect of the invention, there is provided a genetic construct comprising a nucleic acid sequence of the invention, a biologically-active fragment thereof, or a fragment thereof encoding a biologically-active fragment of BEIIb operably linked to one or more nucleic acid sequences which are capable of facilitating expression of BEIIb in a plant, preferably a cereal plant. The construct may be a plasmid or a vector, preferably one suitable for use in transformation of a plant. Such a suitable vector is a bacterium of the genus *Agrobacterium*, preferably *Agrobacterium tumefaciens*. Methods of transforming cereal plants using *Agrobacterium tumefaciens* are known; see for example Australian Patent No. 667939 by Japan Tobacco Inc.; Australian Patent No. 687863 by Japan Tobacco Inc.; International Patent Application No. PCT/US97/10621 by Monsanto Company; and Tingay et al (1997).

In a third aspect, the invention provides a genetic construct for targeting of a desired gene to endosperm of a cereal plant, and/or for modulating the time of expression of a desired gene in endosperm of a cereal plant, comprising a BEIIb promoter, operatively linked to a nucleic acid sequence encoding a desired protein, and optionally also operatively linked to one or more additional targeting sequences and/or one or more 3' untranslated sequences.

The nucleic acid encoding the desired protein may be in either the sense orientation or in the anti-sense orientation.

Alternatively it may be a duplex construct, comprising a portion of the nucleic acid sequence encoding the desired protein in both the sense and anti-sense orientations, operably linked by a spacer sequence. It is contemplated that any desired protein which is encoded by a gene which is capable of being expressed in the endosperm of a cereal plant is suitable for use in the invention. Preferably the desired protein is an enzyme of the starch biosynthetic pathway. For example, the antisense sequences of GBSS, starch debranching enzyme, SBE II, low molecular weight glutenin, or grain softness protein I, may be used Preferred sequences for use in sense orientation include those of bacterial isoamylase, bacterial glycogen synthase, or wheat high molecular weight glutenin Bx17.

In a fourth aspect, the invention provides a wheat BEIIb polypeptide, comprising an amino acid sequence encoded by a nucleic acid molecule according to the invention, or a polypeptide having at least 70%, more preferably 80%, even more preferably 90% amino acid sequence identity thereto, and having the biological activity of BEIIb.

The polypeptide may be designed on the basis of amino acid sequences deduced from the nucleic acid sequences of the invention, or may be generated by expression of the wheat BEIIb nucleic acid molecule in a heterologous system. Suitable heterologous systems are very well known in the art, and the skilled person will readily be able to select a system suitable for the particular purpose desired.

In a fifth aspect, the invention provides an antibody directed against BEII polypeptide. The antibody may be polyclonal or monoclonal. It will be clearly understood that the invention also encompasses biologically-active antibody fragments, such as Fab, $(Fab)_2$, and ScFv. Methods for production of antibodies and fragments thereof are very well known in the art.

The antibodies of the invention may be used for identification and separation of BEIIb proteins, for example by affinity electrophoresis. This greatly facilitates the identification and combination of altered forms of BEIIb via analysis of germplasm, and greatly assists plant breeding. The antibodies of the invention are suitable for use in any affinity-based separation system, preferably using methods which overcome interference by amylases. Suitable methods are known in the art.

In a sixth aspect, the invention provides a plant cell transformed by a genetic construct according to the invention, or a plant derived from such a cell. Additionally, a transformed plant cell may also comprise one or more null alleles for a gene selected from the group consisting of GBSS, BEIIa, and SSII. Preferably the plant is a cereal plant, more preferably wheat or barley.

In a seventh aspect, the invention provides a method of modifying the characteristics of starch produced by a plant, comprising the steps of:

a) increasing the level of expression of BEIIb in the plant, for example by introducing a nucleic acid molecule encoding BEIIb into a host plant, or b) decreasing the level of expression of BEIIb in the plant, for example by introducing an anti-sense nucleic acid sequence directed to a nucleic acid molecule encoding BEIIb into a host plant.

As is well known in the art, over-expression of a gene can be achieved by introduction of additional copies of the gene, and anti-sense sequences can be used to suppress expression of the protein to which the anti-sense sequence is complementary. Other methods of suppressing expression of genes are known in the art, for example co-suppression, RNA duplex formation, or homologous recombination. It would be evident to the person skilled in the art that sense and anti-sense sequences may be chosen depending on the host plant, so as to effect a variety of different modifications of the characteristics of the starch produced by the plant.

Preferably the plant is a cereal plant, more preferably wheat or barley.

Preferably the branching of the amylopectin component of starch is modified by either of these procedures. More preferably a plant with high amylose content is produced.

In an eighth aspect, the invention provides a method of targeting expression of a desired gene to the endosperm of a cereal plant, comprising the step of transforming the plant with a construct according to the invention.

In a ninth aspect, the invention provides a method of identifying a null or altered allele encoding an enzyme of the starch biosynthetic pathway, comprising the step of subjecting DNA from a plant suspected to possess such an allele to a DNA fingerprinting or amplification assay, which utilizes at least one DNA probe comprising one or more of the nucleic acid molecules of the invention. The nucleic acid molecule may be a genomic DNA or a cDNA, and may comprise the full-length coding sequence or a fragment thereof. Any suitable method for identification of BEIIb sequences may be used, including but not limited to PCR, rolling circle amplification, RFLP, and AFLP. Such methods are well known in the art, and any suitable technique may be used.

In a tenth aspect, the invention provides a plant comprising one or more BEIIb null alleles, in combination with one or more other null alleles selected from the group consisting of BEIIa, GBSS, SSII and BEI. Optionally the plant may also comprise a BEIIa or BEIIb gene expressed in either the sense or the anti-sense orientation. The null alleles for BEIIa, GBSS SSII and BEI may be identified using methods described in PCT/AU97/00743.

It will clearly understood that the invention also encompasses products produced from plants according to the invention, including but not limited to whole grain, part grain, flour or starch.

Because of the very close relationship between *Aegilops tauschii*, formerly known as *Triticum tauschii*, and wheat, as discussed in PCT/AU97/00743, results obtained with *A. tauschii* can be directly applied to wheat with little it any modification. Such modification as may be required represents routine trial and error experimentation. Sequences from these genes can be used as probes to identify null or altered alleles in wheat, which can then be used in plant breeding programes to provide modifications of starch characteristics. The novel sequences of the invention can be used in genetic engineering strategies or to introduce a desired gene into a host plant, or to provide anti-sense sequences for suppression of expression of the BEIIb gene in a host plant, in order to modify the characteristics of starch produced by the plant.

While the invention is described in detail in relation to wheat, it will be clearly understood that it is also applicable to other cereal plants of the family Gramineae, such as maize, barley and rice.

Methods for transformation of monocotyledonous plants such as wheat, maize, barley and rice and for regeneration of plants from protoplasts or immature plant embryos are well known in the art. See for example Lazzeri et al, 1991; Jahne et al, 1991 and Wan and Lemaux, 1994 for barley; Wirtzens et al, 1997; Tingay et al, 1997; Canadian Patent Application No. 2092588 by Nehra; Australian Patent Application No. 61781/94 by National Research Council of Canada, and Australian Patents No. 667939 and No. 687863 by Japan Tobacco Co.

The sequences of ADP glucose pyrophosphorylase from barley (Australian Patent Application No. 65392/94), starch debranching enzyme and its promoter from rice (Japanese Patent Publication No. Kokai 6261787 and Japanese Patent Publication No. Kokai 5317057), and starch debranching enzyme from spinach and potato (Australian Patent Application No. 44333/96) are all known.

BRIEF DESCRIPTION OF THE FIGURES

FIG. 1 shows the sequence of the SBE9 branching enzyme cDNA encodes SBE IIa, cloned from a wheat cv Rosella cDNA library (SEQ ID NO:1).

FIG. 2 shows the sequence of the branching enzyme BEIIa gene (SEQ ID NO:2) contained within the F2 lambda clone isolated from an *Aegilops tauschii* genomic DNA library.

FIG. 4 shows the alignment of sequences of Intron 5 fragments (SEQ ID NOS 18-21, respectively in order of appearance) from the A, B and D genomes of wheat.

FIG. 6 shows the alignment of a 262bp PCR fragment amplified from hexaploid wheat using the primers sr913F and WBE2E6R, and a region from the wheat branching enzyme IIb gene wSBE II-DB1 (SEQ ID NO: 21 aligned with residues 2010-2290 of SEQ ID NO: 5, respectively in order of appearance).

FIG. 7 shows the alignment of barley branching enzyme IIb cDNA (SEQ ID NO: 22), wheat branching enzyme IIb cDNA (residues 802-1146 of SEQ ID NO: 6), and SBE9 (residues 537-645 of SEQ ID NO: 1) sequences with the sequence of the wheat (*A. tauschii*) branching enzyme IIb gene (residues 2000-3234 of SEQ ID NO: 5).

FIG. 8 shows the partial genomic sequence of a branching enzyme IIb gene from *A. tauschii* (SEQ ID NO:5).

FIG. 9 shows the sequence of a cDNA for branching enzyme IIb gene from hexaploid wheat (SEQ ID NO: 6).

FIG. 10 shows the sequence alignment of branching enzyme genes (SEQ ID NOS 23-31, respectively in order of appearance). The cDNA sequences used for this analysis were SBE9 (SEQ ID NO: 1; FIG. 1), wheat BEIIb cDNA (SEQ ID NO: 6; FIG. 9), Y11282, a wheat branching enzyme sequence (Nair et al. 1997), barley BEIIa (Sun et al. 1998), barley BEIIb (Sun et al. 1998), rice BEIII (Mizuno et al. 1993), rice BEIV (Genbank Accession No. E14723) maize BEIIa (Gao et al. 1997) and maize BEIIb (Gao et al. 1997). The observed N-terminal of wheat (Morell et al., 1997; Y11282) is shown in bold. (FIG. 1), wheat BEIIb (SEQ ID NO: 9; FIG. 9), barley IIa and IIb (Sun et al. 1998), maize IIa (Gao et al. 1997), maize IIb (Fisher et al. 1993), rice III (Mizuno et al. 1993), rice IV (Genbank accession E14723), potato BEI (Khoshnoodi et al. 1997), potato BE II (Cangiano et al 1993), pea BEI and BEII (Burton et al. 1995), *E.coli* BE (Baecker et al. 1986) and *bacillus* (Kiel et al 1992). Note that pea BE I and pea BE II sequences correspond to maize BE II and BE I respectively because of differences in nomenclature conventions.

Lanes 1 and 4 contain leaf mRNA; lanes 2 and 5 contain pre-anthesis floret mRNA; lanes 3 and 6 contain mRNA from wheat endosperm collected 15 days after anthesis.

Figure 14:

FIG. 14 shows the results of analysis of wheat endosperm branching enzyme IIa by affinity electrophoresis.

Samples: Lanes 1, 4 and 7 contained 20 µg endosperm soluble protein, lanes 2, 5 and 8 contained 30 µg endosperm soluble protein and lanes 3 and 6 contained 10 µg endosperm soluble protein.

Figure 15:
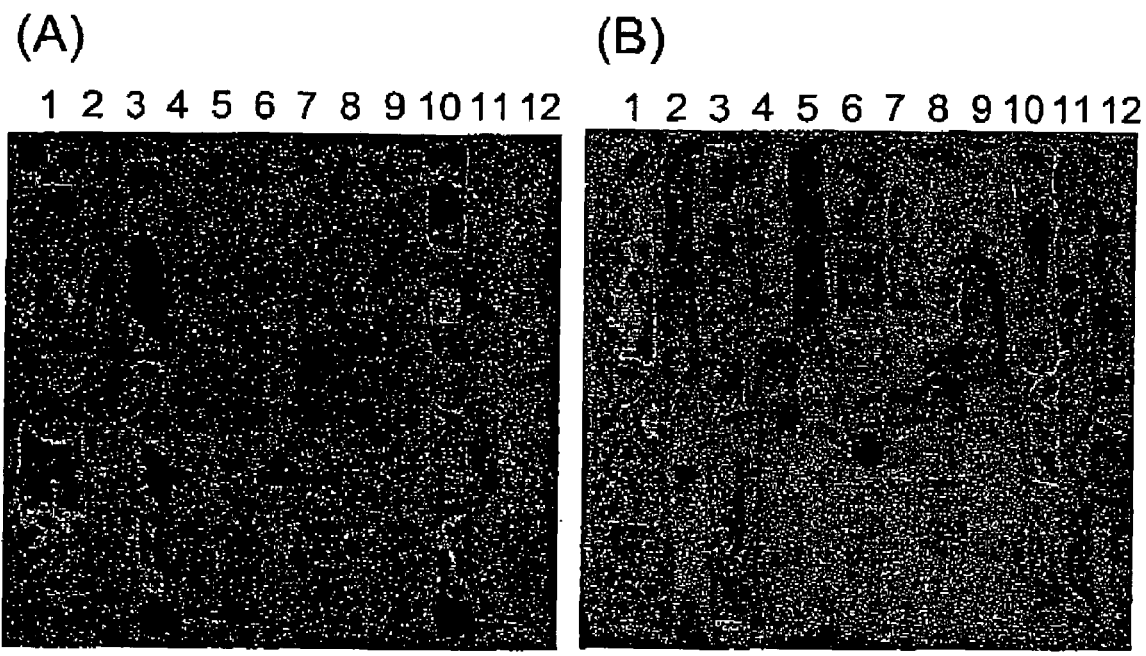

FIG. 15 shows the results of non-denaturing gel electrophoresis analysis of branching enzymes in the soluble fraction of wheat endosperm.

Samples were; Lane 1, R6 pre-immune, 1:100; Lane 2, R6 pre-immune, 1:3000; Lane 3, R6, 1:100; Lane 4, R6, 1:1000; Lane 5, R6, 1:3000; Lane 6, 3KLH, 1:2000; Lane 7, 3KLH, 1:5000; Lane 8, R7 pre-immune, 1:1000; Lane 9, R7 pre-immune 1:5000; Lane 10, R7, 1:1000; Lane 11, R7, 1:3000; Lane 12, R7, 1:5000

Figure 11:
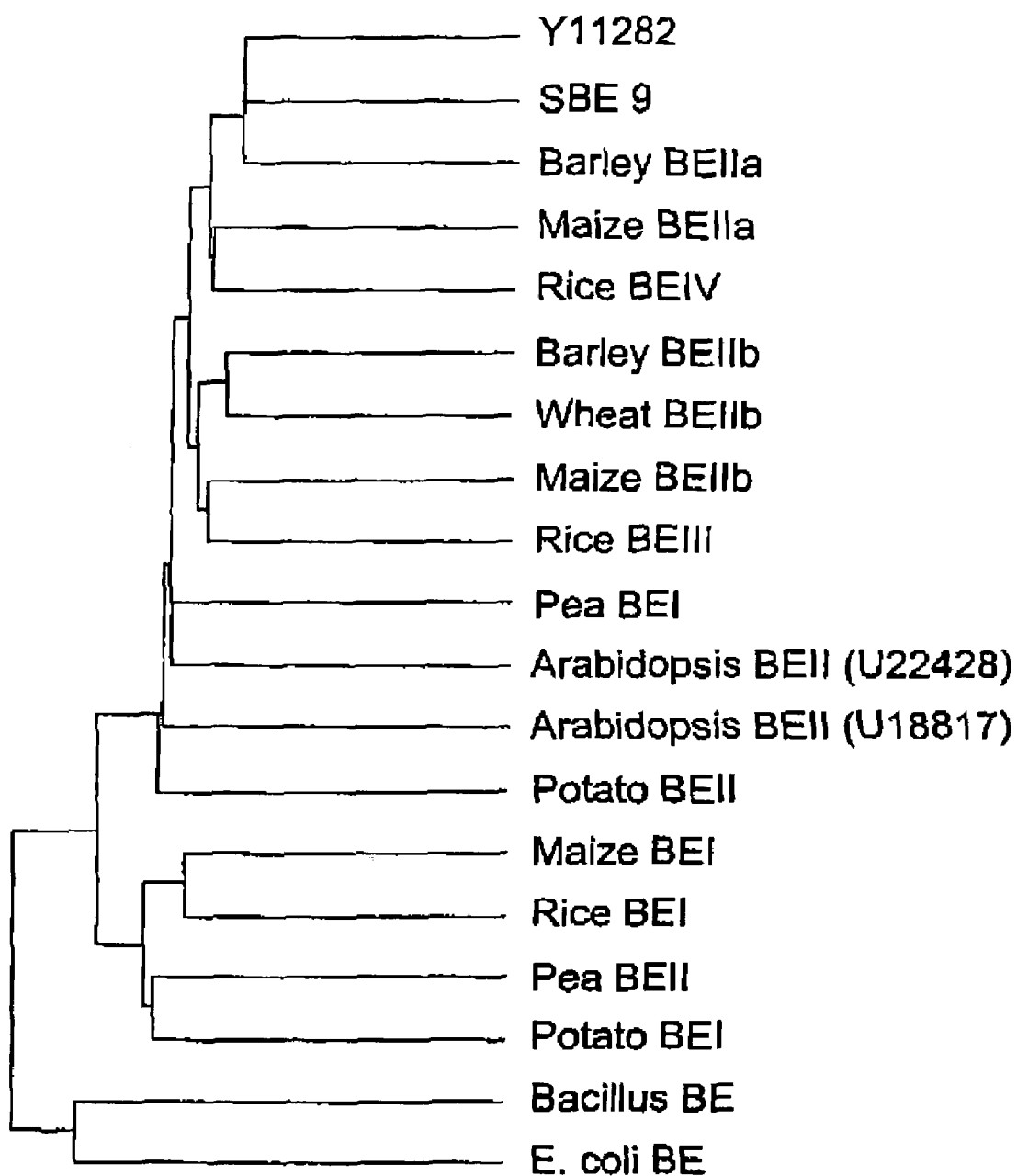
FIG. 11 shows the dendrogram of BE sequences. The sequences analysed were for wheat Y11282 (Nair et al., 1997), SBE 9 (SEQ ID NO: 1.

FIG. 16 shows the results of affinity electrophoresis separation of branching enzyme IIa forms from diverse wheat germplasm using the gel conditions described in FIG. 11 (Panel C). Panel A. Lane 1, Durati, *T. durum*; Lane 2, *A. tauschii*, Accession No. 24242; Lane 3, *A. tauschii*, Accession No. 24095; Lane 4, *A. tauschii*, Accession No. 24092; Lane 5, Hartog, *Triticum aestivum*; Lane 6, Rosella, *T. aestivum*; Lane 7, Corrigin, *T. aestivum*; Lane 8, Bodallin, *T. aestivum*; Lane 9, Beulah, *T. aestivum*; Lane 10 Bindawarra, *T. aestivum*; Lane 11, Barley (*Hordeum vulgare*). Panel B. Lane 1: Afghanistan 006, *Triticum durum*; Lane 2, Persia 20, *T. aestivum*; Lane 3, Afghanistan 8, *T. aestivum*; Lane 4, Kashmir 4, *T. aestivum*; Lane 5, Gandum Sockhak, *T. aestivum*; Lane 6, Warbler, *T. aestivum*; Lane 7, Bayles, *T. aestivum*; Lane 8, Kometa; Lane 9, Kashmir 14, *T. aestivum*; Lane 10, Rosella, *T. aestivum*; Lane 11, Kashmir 8, *T. aestivum*; Lane 12, Beijing 10, *T. aestivum*; Lane 13, Savannah, *T. aestivum*; Lane 14, Afghanistan 55-623, *T. aestivum*; Lane 15, Karizik, *T. aestivum*; Lane 16, Indore E98, *T. durum*; Lane 17, Iraq 17, *T. durum*; Lane 18, Seri 82, *T. aestivum*: Lane 19, Indore 19, *T. aestivum*.

FIG. 17 shows the results of two-dimensional separation of the components of the wheat starch granule 88 kD band. The wheat starch granule 88 kDa band was electrophoresed in the first dimension through an SDS-PAGE gel. Lanes were excised, renatured, and placed on top of a non-denaturing PAGE gel and electrophoresed ina second dimension. Two lanes were placed on top of each non-denaturing PAGE gel. (A) protein staining with Coomassie blue reagent (B) Immunoblotting of gels with either 3KLH or R6 antibodies, as indicated on the figure.

Figure 18:
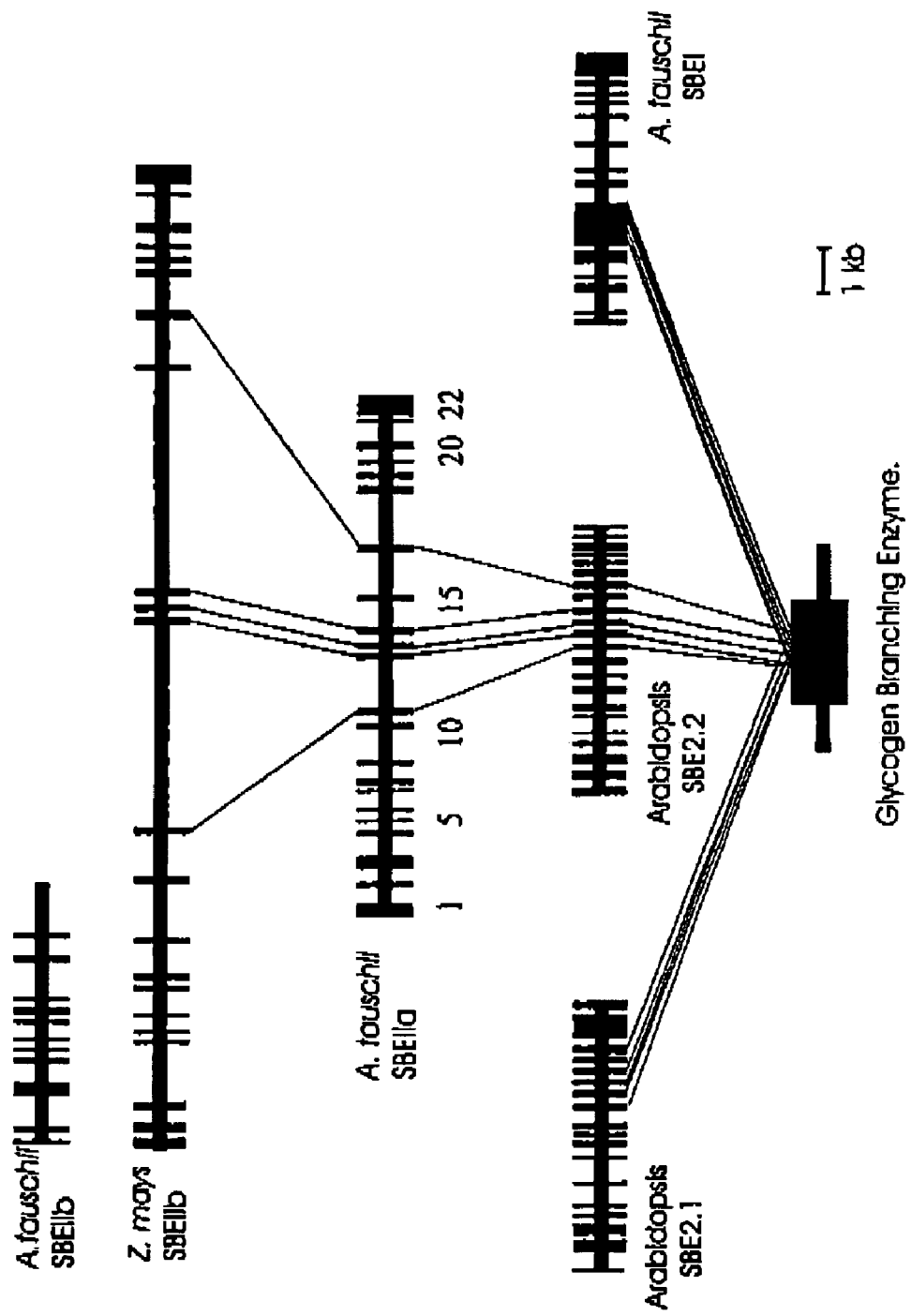

FIG. 18 is a diagrammatic representation of the BEII genes from various species, showing the exon/intron structure. The dark rectangles represent exons.

Figure 19:

FIG. 19 shows the results of PCR amplification of SBE IIb gene from CS nullisomic lines, using the primers ARA 12F and ARA 10R.

Figure 20:
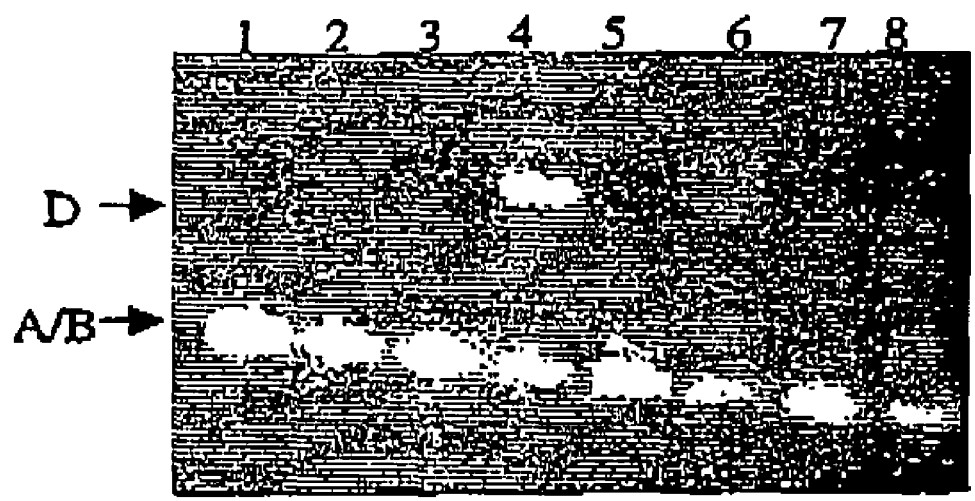

FIG. 20 shows the results of PCR amplification of SBE IIb gene, using the primers ARA 6F and ARA 8R from *Triticum* spp. Lanes: 1) *T. monococcum*, 2) *T. durum*, 3) *T. urartu*, 4) *T. tauschii*, 5) CSDT2DS, 6) CSDT2BL-9, 7) CSDT2AS and 8) CS.

FIG. 21 shows the alignment of the exon 1-intron 1-exon 2 region of the SBE IIb gene from the A, B and D genomes (SEQ ID NOS 32-34, respectively in order of appearance). ★indicates that the sequence could not be specifically assigned to the A or B genome.

FIG. 22 shows the alignment of the BEIIb sequences from each genome (SEQ ID NOS 35-37, respectively in order of appearance).

Figure 23:
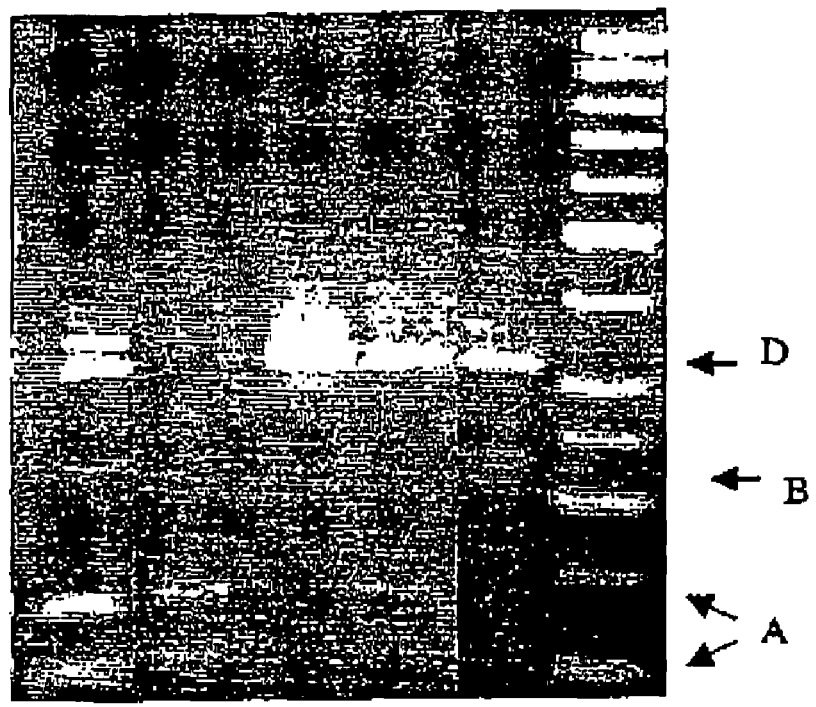

FIG. 23 shows the results of PCR amplification of the SBE IIb gene was carried out using the primers ARA 19F and ARA 15R, followed by restriction digestion using Rsa1. Lanes 1) CS, 2) *T. monococcum,* 3) *T. tauschii,* 4) CSDT2BL-9, which is missing part of the long arm of chromosome 2B, and 6) CSDT2AS, which is missing the long of chromosome 2A.

Figure 24:
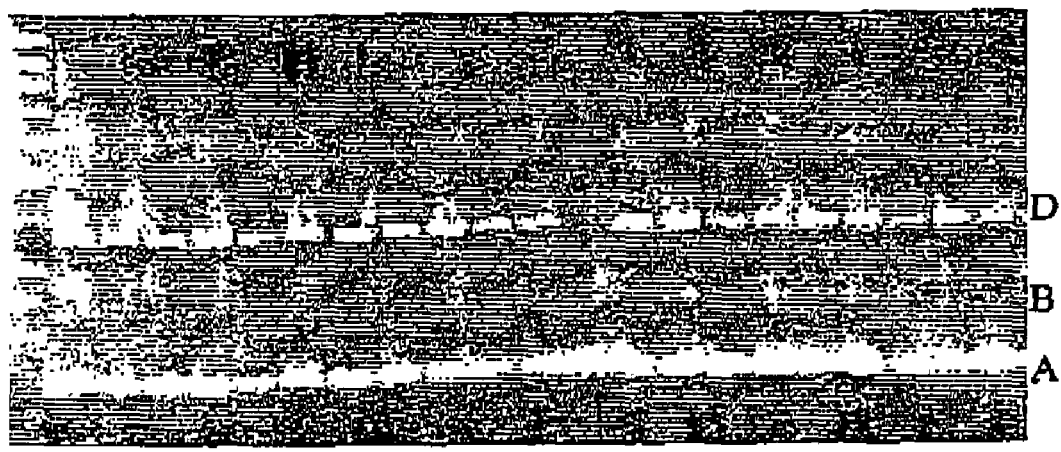
Figure 25:
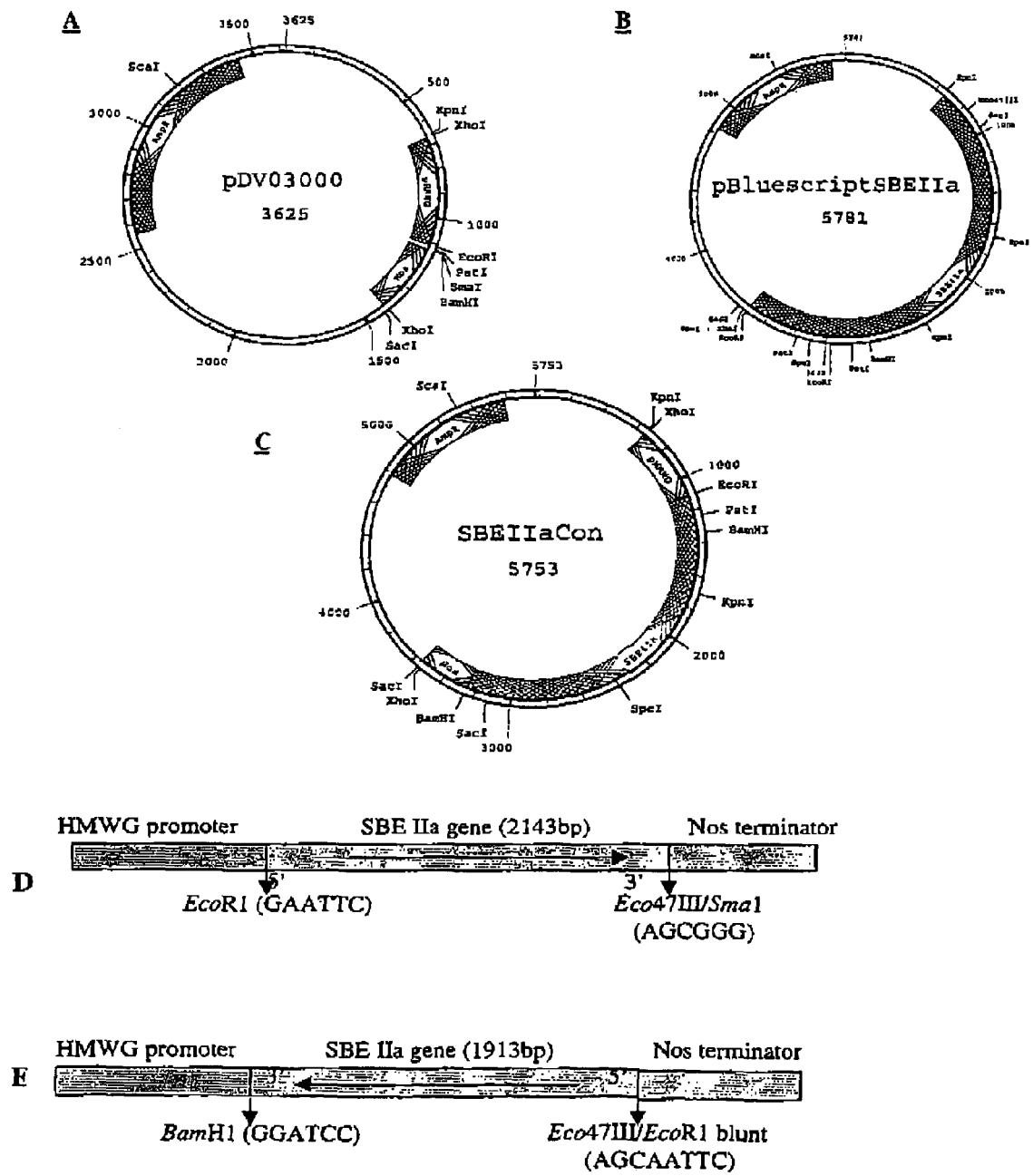

FIG. 24 shows the results of PCR amplification of intron 3 region of SBE IIb from wheat lines, using the primers ARA 19F and ARA 23R followed by Rsa 1 digestion. Lane 12 is the null mutant for the D genome FIG. 25 is a schematic representation showing the development of the SBE IIa construct. A) Biogemma vector, pDV03000; B) pBluescript carrying the full length cDNA of SBE IIa; C) SBE IIa construct in pDV03000; D) Sense IIa construct and E) Antisense IIa construct.

Figure 26:
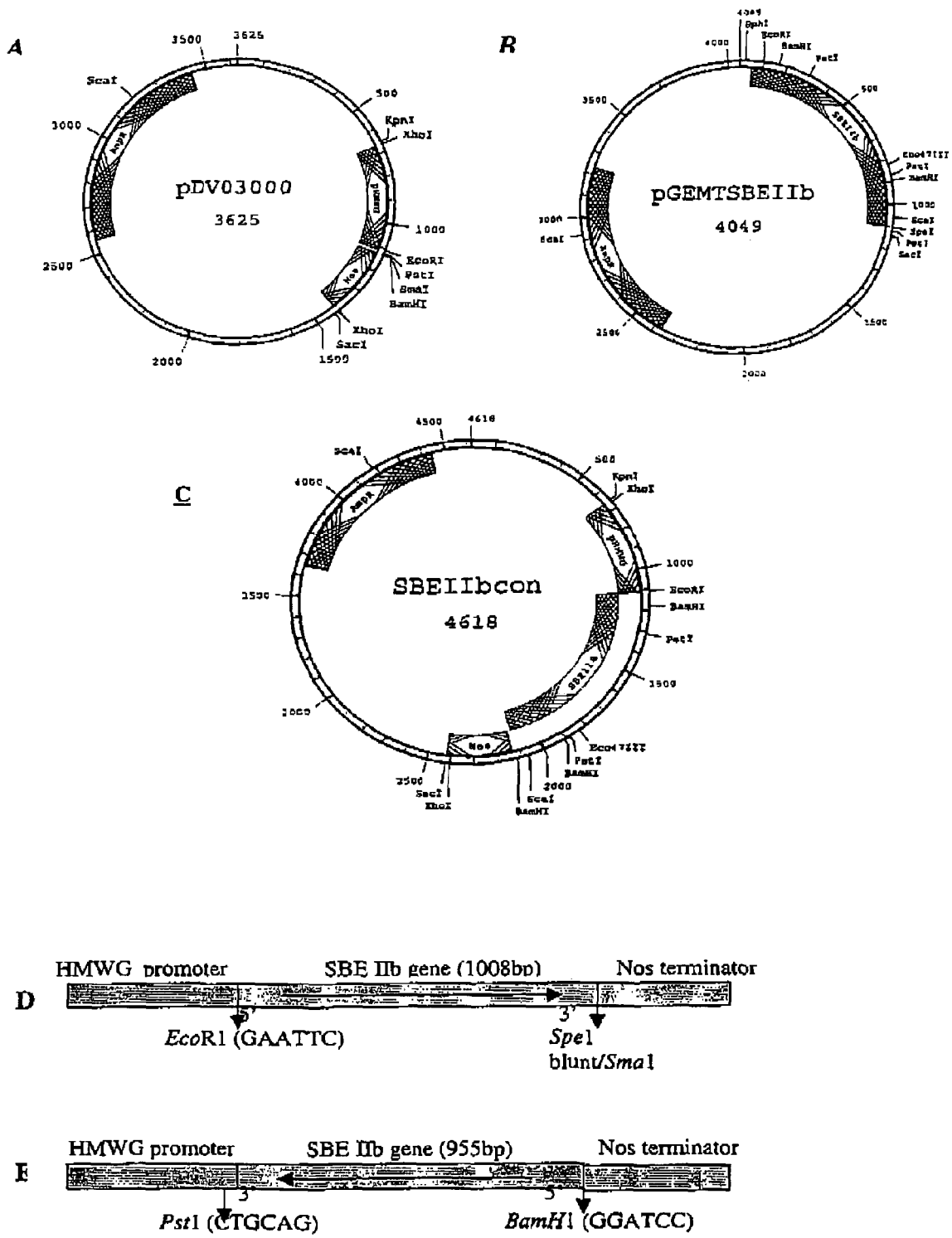

FIG. 26 is a schematic representation of the development of the SBE IIb construct. A) Biogemma vector, pDV03000; B) pGEM-T carrying a 1046bp fragment of SBE IIb; C) SBE IIb construct in pDV03000; D) Sense IIb construct and E) Antisense IIb construct.

Figure 27:
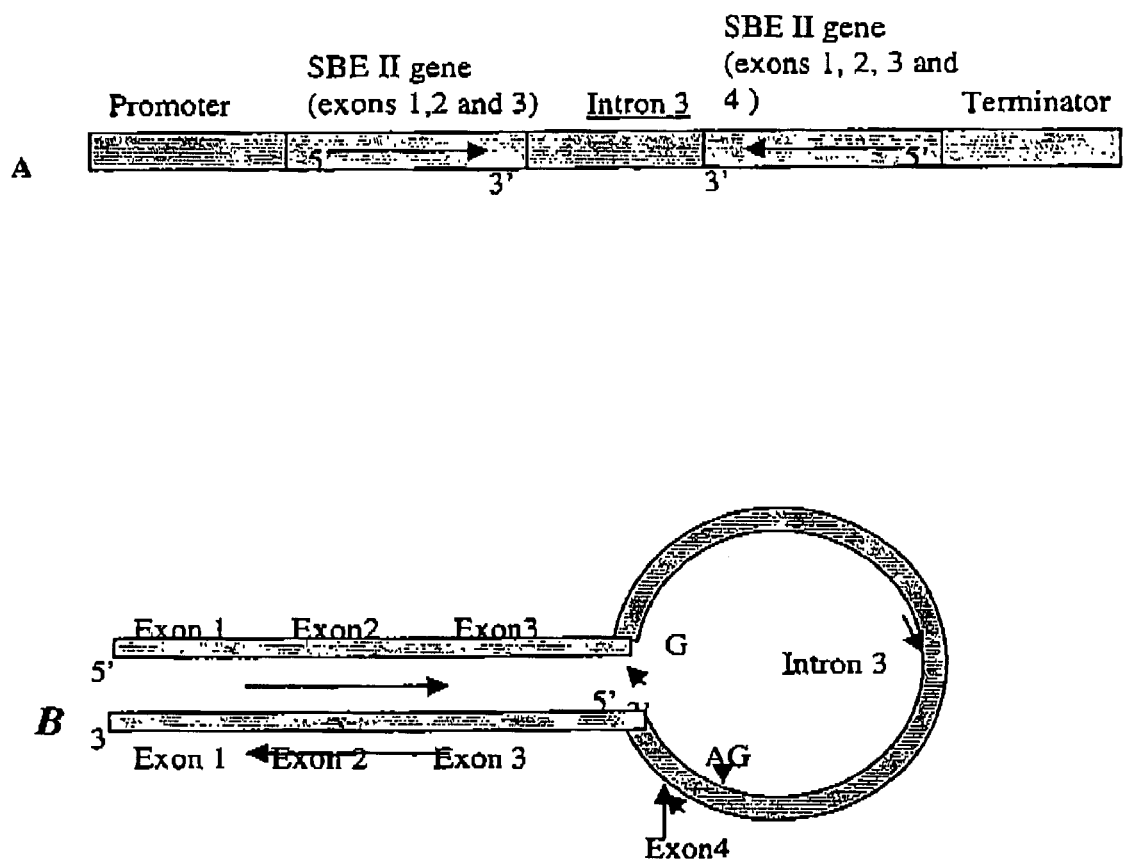

FIG. 27 is a schematic representation of a SBE II duplex construct. A) SBE sequence inserted in between the promoter and the terminator in its linear form; B) Duplex formation of mRNA within the transgenic plant.

EXAMPLE 1

Isolation of BEII Genes from an *A. tauschii* Genomic Library and their Characterisation by PCR Plant Material

*Aegilops tauschii*, CPI 110799, was used for the construction of the genomic library. Previously this accession has been shown to be most like the ancestral D genome donor of wheat, on the basis of the conservation of order of genetic markers (Lagudah et al. 1991). The *Triticum aestivum* cultivars Rosella, Wyuna and Chinese Spring were used for the construction of different cDNA libraries.

cDNA and Genomic Libraries

The construction of the cDNA and genomic libraries used in this example was as described in Rahman et al., (1997, 1999) and in Li et al. (1999). Conditions for library screening were hybridisation at 25% formamide, 5×SSC, 0.1% SDS, 10× Denhardts, 100 µg/ml salmon sperm DNA at 42° C. for 16 h, followed by washing at 2×SSC, 0.1% SDS at 65° C. for 3×1 h.

Screening of a Wheat cDNA Library

Screening of a wheat cv Rosella cDNA library prepared from endosperm (mid-stage of development) with the maize SBE I clone (Baba et al., 1991) at low hybridisation stringency led to the isolation of two classes of positive plaques. One class hybridised strongly to the probe, and encoded wheat SBE I (Rahman et al., 1997, 1999). The second class was weakly hybridising. The clone with the longest insert from this second class was called SBE 9, and its sequence showed greater identity to SBE II than to SBE I type sequences. This was designated SBE IIa. The sequence of SBE 9 (SEQ ID NO:1) is set out in FIG. 1.

Screening of *A. tauschii* Genomic Library

A genomic library constructed from *A. tauschii* was screened by DNA hybridisation with SBE9, and four positive clones were purified. These were designated F1 to F4. The sequence from positions 537 to 890 of SBE9 was amplified by PCR, and used to screen the *A. tauschii* library again. Clones isolated from this screening are referred to as G1 and G2 and H1 to H8

(1) Number of BEII Type Genes in Wheat

Figure 3:
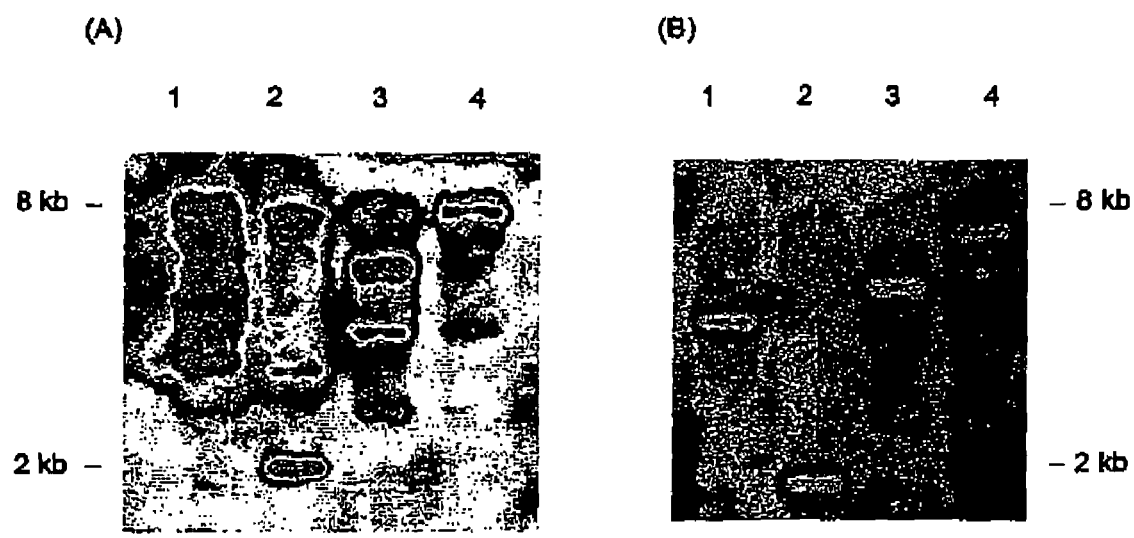
FIG. 3 shows the results of hybridisation of *Aegilops tauschii* DNA with probes derived from wSBE II-DA1 type sequences. A. Hybridisation with a probe from SBE9 consisting of exons 5-9. B. Hybridisation with fragment F2.2 (consisting of exons 4-9 and introns 4-8 and part of introns 3 and 9). Enzymes used for the digest were: 1. Bam HI, 2. Dra I, 3. EcoR I, 4. EcoR V. Molecular size markers are indicated.

The sequence of a branching enzyme gene, designated F2, from *Aegilops tauschii* was described in WO99/14314, and is given in FIG. 2 (SEQ ID NO:2). A probe generated from F2, designated F2.2, contained sequences from 2704 to 4456 bp of SEQ ID NO:2, and contained exons 4-9, introns 4-8, and parts of intron 3 and 9. Hybridisation of *A. tauschii* DNA (cut with four different restriction enzymes) with F2.2 revealed only one strongly hybridising band and several very faint bands (FIG. 3, panel B), consistent with the presence of a single BEII type gene in the *A. tauschii* genome. The cDNA clone, SBE9 (SEQ ID NO:1) has >95% identity to the exon regions of the F2 branching enzyme gene. A region of SBE9 from nucleotides 537 to 890, including exons 5 to 9, was used as a hybridisation probe, and gave a much more complex pattern (FIG. 3, panel A), strongly indicating that there is more than one BEII gene type in the *A. tauschii* genome.

EXAMPLE 2

PCR Analysis of BEIIa—Intron 5

PCR primers, sr913F (5' ATC ACT TAC CGA GAA TGG G 3', SEQ ID NO:3) and WBE2E6R (5' CTG CAT TTG CAT TTC AAT TG 3', SEQ ID NO:4) were designed to anneal to Exon 5 and Exon 6 respectively of the wheat F2 gene in order to amplify the intron region (Intron 5) between these exons. Analysis of the products of PCR reactions using these primers shows that the primers amplify fragments of 228 bp from the A-genome of wheat, 226 bp from the D genome and 217 bp from the B genome. These fragments were shown to be amplified from chromosome 2A, 2D and 2B of wheat respectively by analysis of nullisomic/tetrasomic chromosome-engineered lines of wheat. In addition to these fragments, a 262 bp fragment was amplified, and this fragment (designated the 262 bp Universal fragment) was not polymorphic among the chromosome engineered lines tested. The 262 bp Universal fragment and the A, B and D regions from the F2 gene were cloned and sequenced, and the sequence comparison is shown in FIG. 4.

EXAMPLE 3

Classification of the G1-G2 and H1-H10 Genes

Figure 5:
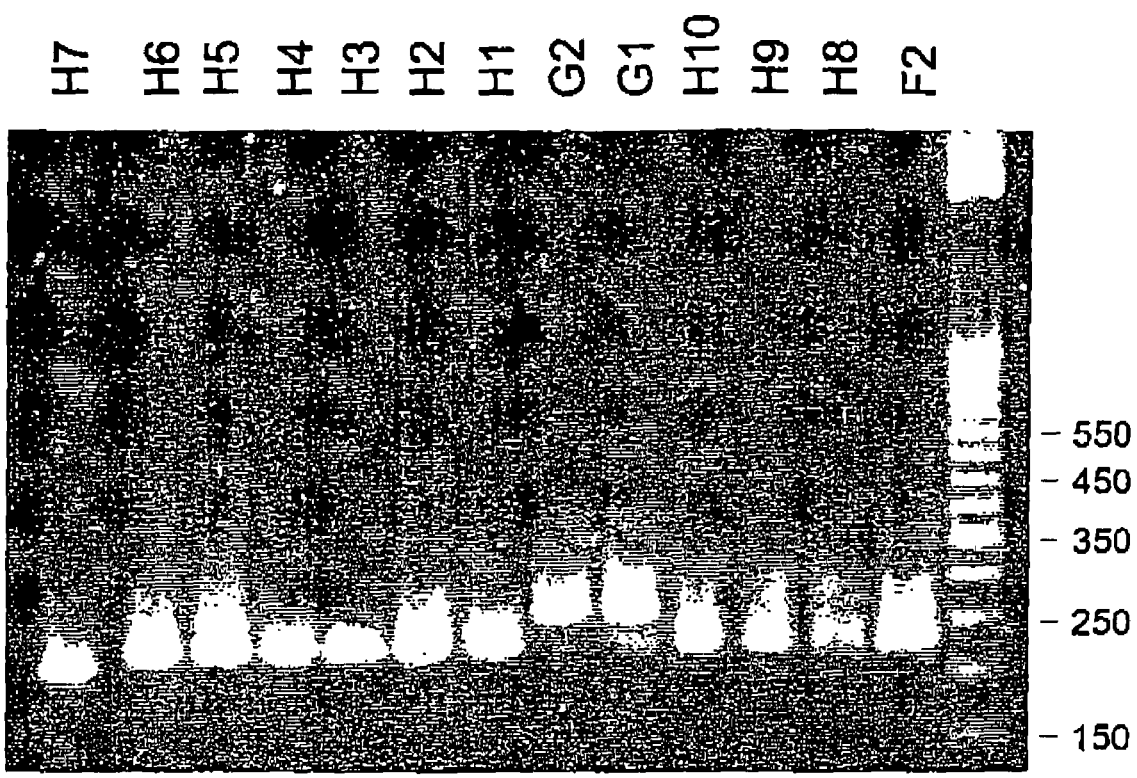
FIG. 5 shows the PCR analysis of *A. tauschii* genomic clones using Intron V sequences.

PCR analysis using PCR primers sr913F (5' ATC ACT TAC CGA GAA TGG G 3', SEQ ID NO: 3) and WBE2E6R (5' CTG CAT TTG GAT TTC AAT TG 3', SEQ ID NO: 4) showed that the H1 to H10 lambda clones yielded an approximately 200 bp fragment, and the G1 and G2 clones yielded an approximately 260 bp fragment (FIG. 5). Partial sequencing of G1 and G2 showed that the parts of the sequence analysed had 80% identity with the exons 4 and 5 of wSBE II-DA1, but the intervening intron contained a sequence that showed no homology to any sequence contained within F2.

Figure 7:
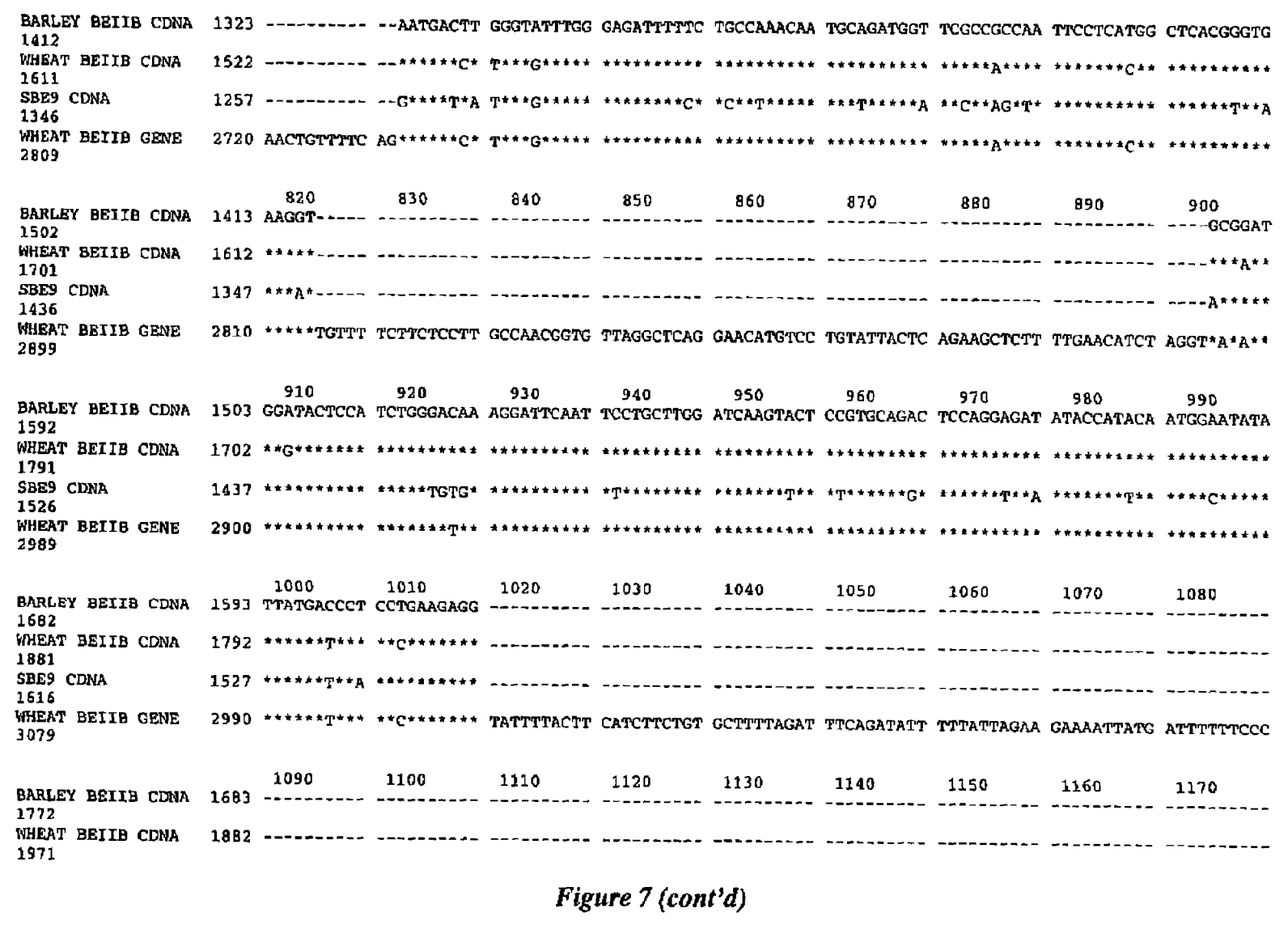

However, the G1 and G2 clones from *A. tauschii* showed 92.7% identity to the sequence of the 262 bp universal fragment amplified and cloned from hexaploid wheat, and an alignment of these sequences is shown in FIG. 6. FIG. 7 shows an alignment of a region corresponding to the 537 to 890 bp region of the SBE9 clone from the cDNAs for barley BEIIb (Sun et al., 1995, Sun et al., 1998), SBE9, wheat BEIIb cDNA with the sequence from clone G1. Further sequencing of G1 led to the isolation of a sequence, shown in FIG. 8 (SEQ ID NO:5), which showed high identity with the sequence reported by Sun et al.(1998) for the 5' end of barley IIb cDNA and the partial sequence for the cognate gene. G1 and G2 therefore contain a gene which is distinct from F2, and which has high homology to barley BEIIb. We have designated this gene wSBE II-DB1.

EXAMPLE 4

Isolation of a Wheat BEIIb cDNA and an Additional Genomic Fragment

A barley cDNA library was constructed using 5 µg of polyA+ mRNA (1.67 µg of polyA+ mRNA from 10, 12 and 15 DPA endosperm tissues were pooled). cDNA was synthesised using the cDNA synthesis system marketed by Life Technology, except that the NotI-(dT)$_{18}$ primer (Pharmacia Biotech) was used to synthesise the first strand of cDNA. Pfu polymerase was added to the reaction after second strand synthesis to flush the ends of cDNAs. SalI-XhoI adapter (Stratagene) was then added to the cDNAs. cDNAs were ligated to SalI-NotI arms of λZipLox (Life Technology) after digestion of cDNAs with NotI followed by size fractionation (SizeSep 400 spun Column of Pharmacia Biotech). The entire ligation reaction (5 µl) was packaged using Gigapack III Gold packaging extract (Stratagene). The titre of the library was tested by transfecting either the Y1090(ZL) or the LE392 strain of *E. coli*.

Primers 1 and 2 (Sun et al. 1998)), were used for PCR amplification of a fragment from a barley cDNA library (Ali et al., 2000) using conditions described in Sun at al. (1998). The identity of this fragment was confirmed by sequence analysis, and the fragment was used as a probe to isolate a cDNA by hybridisation, cDNA from a cDNA library constructed from Chinese Spring (Li et al. 1999).

This cDNA was designed wBEIIb, and its sequence is shown in FIG. 9 (SEQ ID NO:6). This probe was also used to reprobe the genomic library from *A. tauschii* referred to above, and a clone, designated G5, was recovered from this screen. Analysis showed that the wBEIIb cDNA sequence showed 98.5% identity and the G5 sequence showed 100% identity to sequences already recovered from G1 and G2. G5 therefore represented the same wSBE II-DB1 gene, and the wBEIIb cDNA is a product of the orthologous gene in hexaploid wheat.

EXAMPLE 5

Relationships Between BEII Sequences

Deduced amino acid sequences for branching enzymes from various cereals were analysed using the PILEUP program from the GCG suite of programs (Devereux 1984), and an alignment of these sequences is shown in FIG. 10. The PILEUP analysis used a penalty of 12 for insertion of a gap and 0.1 for extending the gap per residue. The cDNA sequences used for this analysis were SBE9 (SEQ ID NO:1; FIG. 1), wheat BEIIb cDNA (SEQ ID NO:6; FIG. 9), Y11282, a wheat branching enzyme sequence (Nair et al. 1997), barley BEIIa (Sun et al. 1998), barley BEIIb (Sun et al. 1998); rice BEIII (Mizuno et al. 1993), rice BEIV (Genbank Accession No. E14723) maize BEIIa (Gao et al. 1997) and maize BEIIb (Fisher et al., 1993). The observed N-terminal of wheat (Morell et al., 1997; Y11282) is shown in bold.

The relationships between branching enzyme sequences are illustrated in FIG. 11, using a dendrogram generated by the PILEUP program. The sequences analysed were for wheat Y11282 (Nair at al., 1997), SBE 9 (FIG. 1), wheat BEIIb (FIG. 9), barley IIa and IIb (Sun et al. 1998), maize BEI (Kim et al, 1998), maize IIa (Gao et al. 1997), maize IIb (Fisher et al. 1993), *Arabidopsis* BEII (U22428, Fisher et al., 1996), *Arabidopsis* BEII (U18817, Fisher et al., 1996), rice I (Kawasaki et al., 1993), rice III (Mizuno et al. 1993), rice IV (Genbank accession E14723), potato BEI (Khoshnoodi et al. 1997), potato BE II (Cangiano et al 1993), pea BEI and BEII (Burton et al. 1995), *E. coli* BE (Baecker et al. 1986) and *bacillus* (Kiel et al 1992). Note that pea BE I and pea BE II sequences correspond to maize BE II and BE I respectively because of differences in nomenclature conventions.

On the basis of this comparison, the branching enzyme gene contained on clone F2 was classified as a BEIIa type gene and designated wSBE II-DA1.

EXAMPLE 6

Structure of the wSBE II-DA1 and wSBE II-DB1 Genes

Figure 12:
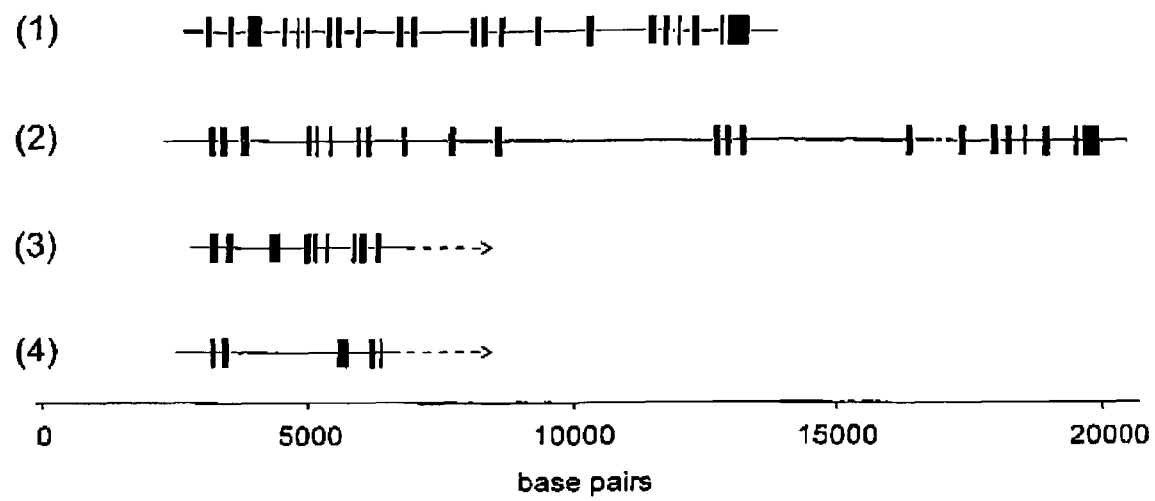
FIG. 12 shows the comparison of exon/intron structure for the BEIIa and BEIIb genes. (1) wheat branching enzyme IIa gene, wSBE II DA1 (2) maize amylose extender BEIIb gene (3) partial wheat branching enzyme IIb gene, wSBE II DB1 (4) partial barley branching enzyme IIb gene.

FIG. 12 shows a comparison of the exon/intron structures of the wheat wSBE II-DA1 and wSBE II-DB1 genes. The structure of the wSBE II-DB1 gene is shown from the beginning of the wheat BEIIb cDNA through to exon 5. Hybridisation results suggest that regions at the 3' end of the wheat BEIIb cDNA are not contained within any of the clones G1, G2 and G5. This is not surprising, as the maize SBE II b gene extends over 16.5 kb and required the isolation of two genomic clones (Kim et al 1998). The positions of the intron/exon boundaries for the first five introns of the wheat BEIIa and BEIIb genes are conserved, as shown in Table 1. The size of the first five introns in wSBE II-DB1 vary considerably in size from the first five introns in wSBE II-DA1.

TABLE 1

Exon/Intron Structures of Cereal branching Enzyme Genes

| | Exons | | | | | Introns | | | |
|---|---|---|---|---|---|---|---|---|---|
| | Wheat wSBE II-DAl | Maize BEIIb | Wheat WSBE II-DB1 | Barley BEIIb | | Wheat wSBE II-DA1 | Maize BEIIb | Wheat WSBE II-DB1 | Barley BEIIb |
| 1 | 123[a] | 112[a] | 148[a] | 121[a] | 1 | 327 | 106 | 148 | 105 |
| 2 | 98 | 146 | 146 | 152 | 2 | 276 | 244 | 663 | 2064 |
| 3 | 242 | 155 | 230 | 230 | 3 | 401 | 1086 | 465 | 388 |
| 4 | 99 | 99 | 99 | 99 | 4 | 169 | 76 | 74 | 74 |

TABLE 1-continued

Exon/Intron Structures of Cereal branching Enzyme Genes

| | Exons | | | | | Introns | | |
|---|---|---|---|---|---|---|---|---|
| | Wheat wSBE II-DA1 | Maize BEIIb | Wheat WSBE II-DB1 | Barley BEIIb | | Wheat wSBE II-DA1 | Maize BEIIb | Wheat WSBE II-DB1 | Barley BEIIb |
| 5 | 43 | 43 | 43 | 43[b] | 5 | 152 | 196 | 181 | |
| 6 | 60 | 60 | 60 | | 6 | 335 | 499 | 442 | |
| 7 | 81 | 81 | 81 | | 7 | 83 | 81 | 79 | |
| 8 | 117 | 117 | 117 | | 8 | 288 | 567 | 178 | |
| 9 | 81 | 84 | 84 | | 9 | 629 | 775 | | |
| 10 | 122 | 122 | | | 10 | 175 | 751 | | |
| 11 | 120 | 120 | | | 11 | 974 | 4020 | | |
| 12 | 130 | 130 | | | 12 | 88 | 86 | | |
| 13 | 111 | 111 | | | 13 | 201 | 148 | | |
| 14 | 129 | 129 | | | 14 | 579 | 3051 | | |
| 15 | 104 | 104 | | | 15 | 841 | 872 | | |
| 16 | 145 | 145 | | | 16 | 1019 | 457 | | |
| 17 | 148 | 148 | | | 17 | 135 | 144 | | |
| 18 | 105 | 101 | | | 18 | 176 | 226 | | |
| 19 | 74 | 78 | | | 19 | 201 | 266 | | |
| 20 | 156 | 156 | | | 20 | 377 | 448 | | |
| 21 | 75 | 75 | | | 21 | 89 | 96 | | |
| 22 | 384 | 84 | | | | | | | |

[a]Exon 1 numbering begins from ATG of translation start codon
[b]Partial sequence for exon or intron

EXAMPLE 7

Expression Analysis at the mRNA Level

Figure 13:
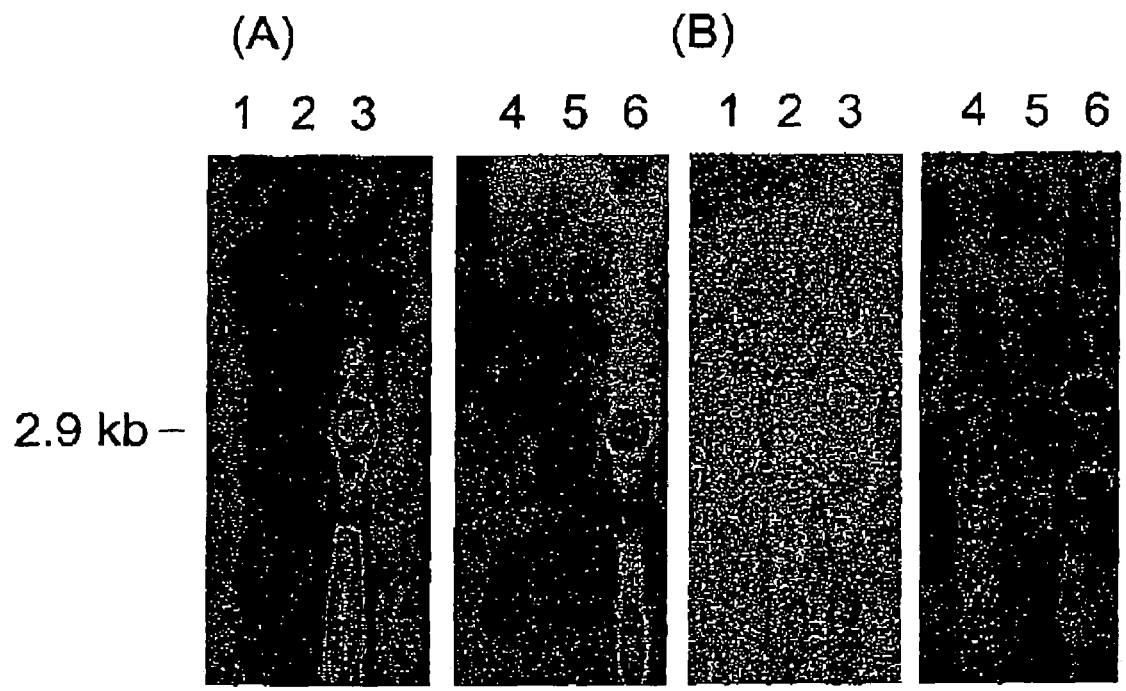
FIG. 13 shows the results of analysis of the expression of mRNA for the BEIIa and BEIIb genes in wheat. Panel (A): Hybridisation of SBE9 probe to lanes 1 to 3 and hybridisation of wheat BEIIb cDNA probe to lanes 4 to 6 Panel (B): mRNA loading for each lane.

RNA from endosperm at different developmental stages was obtained from wheat grown in the glasshouse as described in Li et al. (1999). RNA was extracted by the method of Higgins et al. (1976), separated on denaturing formamide gels and blotted onto Hybond N+ paper, essentially as described in Maniatis et al. (1992). Probes were prepared from the extreme 3' ends of SBE9 (bases 2450 to 2640 of SEQ ID NO:1) and wBEIIb cDNA (bases 2700 to 2890 of SEQ ID NO:6) by PCR using the following scheme: 94° C., 2 min, 1 cycle, 94° C., 30 s, 55° C., 30 s, 72° C., 30 s, 36 cycles, 72° C. 5 min, 1 cycle, 25° C., 1 min, 1 cycle. The probes were from the 3' untranslated region, and were specific for either wSBE II-DA1 or wSBE II-DB1 type sequences. An RNA species of about 2.9 kb hybridised to each probe (FIG. 13 Panel B). However, the intensity of hybridisation determined by densitometry, and normalised for differences in RNA loading), indicated that RNA hybridising to the wSBE II-DB1 gene was present at 2.5 to 3 fold lower concentration than RNA hybridising to the wSBE II-DA1 gene

EXAMPLE 8

Analysis of Branching Enzymes by Affinity Electrophoresis Demonstrates that only BEIIa is Predominant in the Soluble Fraction In Morell et al., (1997), we reported that only a single form of branching enzyme II could be identified in the wheat developing endosperm soluble fraction. However, this was on the basis of anion-exchange chromatography, and it remained possible that there were multiple forms, even though they could not be separated by this technique. Matsumoto has developed an affinity electrophoresis method for measuring the interaction of branching enzymes with polysaccharide substrates (Matsumoto et al., 1990), and we have further developed this technique specifically to allow the separation of the branching enzyme IIa forms encoded by each of the three wheat genomes. FIG. 14 shows an immunoblot of a non-denaturing polyacrylamide gel electrophoresis experiment in which the gel matrix contained the β-limit dextrin of maize amylopectin alone (FIG. 14, lanes 1 and 2), showing separation of three forms of branching enzyme IIa. Resolution is slightly enhanced by the addition of the α-amylase inhibitor acarbose (FIG. 14, lanes 3,4 and 5), and substantially enhanced by the addition of α-cyclodextrin (FIG. 14 lanes 6, 7 and 8).

A non-denaturing gel was prepared, containing a stacking gel composed of 0.125 M Tris-HCl buffer (pH 6.8), 6% acrylamide, 0.06% ammonium persulphate and 0.1% TEMED. The separating gel was composed of three panels. The basic non-denaturing gel mix contained 0.34 M Tris-HCl buffer (pH 8.8), CHAPS (0.05%), glycerol (10.3%), acrylamide (6.2%), 0.06% ammonium persulphate, 0.1% TEMED and the β-limit dextrin of maize amylopectin (0.155%). Panel A (lanes 1 and 2) contained only the basic non-denaturing gel reagents. Panel B (Lanes 3, 4 and 5) contained the basic non-denaturing gel reagents and 0.066 mM acarbose. Panel C (lanes 6, 7 and 8) contained the basic non-denaturing gel reagents and 0.067 mM α-cyclodextrin.

Following electrophoresis at 100 V for 16 hours at 4° C., the proteins in the separating gel were transferred to nitrocellulose membrane according to Morell et al (1997) and immunoreacted with 1:5000 dilution of 3KLH antibodies (raised against the synthetic peptide AASPGKVLVPDESDDLGC (SEQ ID NO:7) coupled to the keyhole limpet hemocyanin via the heterobifunctional reagent m-Maleimidobenzoyl-N-hydroxysuccinimide ester).

The use of a β-limit dextrin provides a superior separation because it prevents interference with the separation by endogenous β-amylases in the wheat endosperm tissue, and the use of α-cyclodextrin in the assay further enhances the separation. Without wishing to limit the invention by any proposed mechanism, we believe that this enhancement may result from the inhibition of endogenous wheat endosperm α-amylases.

The analysis shows that three branching enzyme II proteins are present, and that each of these proteins cross-reacts with antibodies to a synthetic oligopeptide designed from the N-terminal region of the BEIIa protein in a region that shares no homology with the wheat BEIIb protein.

The soluble fraction of the wheat endosperm was reacted with various antibodies raised against peptides designed on the basis of the sequences of the wheat BEIIa (see FIG. 12) or the wheat BEIIb cDNA. FIG. 15 shows that only 3KLH, raised against the N-terminus of BEIIa, cross-reacted with proteins (marked by arrows) in the soluble fraction which show a specific shift in mobility in the presence of the β-limit dextrin of amylopectin and α-cyclodextrin. Gels were prepared as described in FIG. 14, except that the gel used in Panel A contained the non-denaturing gel mix without the β-limit dextrin of maize amylopectin. Panel B contained the non-denaturing gel mix plus α-cyclodextrin. An extract of developing wheat endosperm was prepared using 3 volumes of extraction buffer per g of tissue, and 140 µl of sample applied per gel. Following electrophoresis at 100 V for 16 hours at 4° C., the proteins in the separating gel were transferred to nitrocellulose membrane according to Morell et al (1997) which was cut into 1 cm strips. The antibodies prepared were 3KLH (see FIG. 11), R6 (raised in rabbit against the synthetic peptide AGGPSGEVMIGC (SEQ ID NO:8) coupled to the keyhole limpet hemocyanin via the heterobifunctional reagent m-Maleimidobenzoyl-N-hydroxysuccinimide ester); pre-immune serum from the R6 rabbit; R7 (raised in rabbit against the synthetic peptide GGTPPSIDGPVQDSDGC (SEQ ID NO:9) coupled to the keyhole limpet hemocyanin via the heterobifunctional reagent m-maleimidobenzoyl-N-hydroxysuccinimide ester) and pre-immune serum from the R7 rabbit.

As in FIG. 14, the BEIIa protein is separated into three forms (indicated by arrows in FIG. 15, Panel B), by affinity electrophoresis in the presence of β-limit dextrin. In barley (Sun et al., 1997) and maize (Bayer and Preiss 1981) both branching enzymes IIa and IIb are present in the soluble fraction. In some subsequent experiments we have detected low levels of BE IIb in the soluble fraction. The separation of the forms of BEIIa encoded by each wheat genome is demonstrated in FIG. 16. In Panel (A) the diploid *A. tauschii* (lanes 2,3 and 4) and barley line (lane 11) yields a single band. However, the tetraploid *T. durum* lines (Panel A lane 1, Panel B, lanes 1, 16, and 17) and hexaploid *T. aestivum* lines (Panel A lanes 5-10, Panel B lanes 2-15, 18-19) give at least 2 bands. Some hexaploid lines (panel A, lane 7 and 9, Panel B lanes 2-6, lanes 8-9, lane 13) yield 2 bands, indicating either that they are null for one genome or that the products of two genomes migrate with identical mobility in the gel system.

The use of the separation system as a means of screening for wheat genomes with altered or null alleles of branching enzyme IIa is demonstrated by FIG. 14 (Panel B), where different lines are shown to have different numbers and mobilities of branching enzyme IIa proteins.

EXAMPLE 9

Presence of Two Classes of Proteins in the Starch Granule at 88 kDa and their Differential Antibody Binding The wheat starch granule contains a number of proteins that have been analysed by SDS-PAGE (Rahman et al., 1995, Denyer at al., 1995, Takaoka et al, Li et al., 1999a, Li et al, 1999b) and two-dimensional gel electrophoresis (Yamamori and Endo, 1996). The following bands have been identified: 60 kDa, GBSS; 75 kDa, SSI; 100 kDa, 108 kDa and 115 kDa, SSII). An 88 kDa band is also observed, and has been shown to be associated with branching enzyme activity (Denyer et al., 1995) and to react to antibodies to maize BEII (Rahman et al., 1995). This protein band was shown to contain at least two protein components.

This analysis has been extended by purification and analysis of the individual granule proteins. The granule proteins were isolated from 4.7 g of wheat starch granules by boiling in 24 ml of SDS buffer (50 mM Tris-HCl buffer pH 6.8, 10% SDS and 6.25% 2-mercaptothanol) as described by Rahman et al., (1995). Residual granular starch was removed by centrifugation, and granule proteins were separated by applying the supernatant to a 9% SDS-PAGE gel prepared in a Biorad Model 491 Prep Cell apparatus. The SDS gel contained a stacking gel composed of 0.125 M Tris-HCl buffer (pH 6.8), 0.25% SDS, 6% acrylamide, 0.06% ammonium persulphate and 0.1% TEMED and a separating gel containing 0.34 M Tris-HCl buffer (pH 8.8), 0.25% SDS, acrylamide (9%), 0.06% ammonium persulphate, and 0.1% TEMED. The samples were electrophoresised at 60 mAmp constant current for 16 hours, and fractions of ractions (5 ml) collected by a pump operating at 0.5 ml/min. Fractions were analysed by SDS-PAGE, and fractions containing an 88 kDA band precipitated by the addition of 3 volumes of acetone. The precipitate from each 5 ml fraction was collected by centrifugation, the sample dissolved in SDS buffer, and electrophoresed through a standard 8% SDS-PAGE gel. The lane was excised from the gel and renatured in 0.04 M Tris for 2 hours. To generate a two-dimensional separation, the gel was then laid across the top of a second non-denaturing PAGE gel and electrophoresed. Proteins were identified by staining with Coomassie blue (a 50:50 mixture of 2.5% Coomassie Blue R-250 and Coomassie Blue G250 solutions).

FIG. 17, Panel (A) shows that two proteins were visible after staining, and these were designated 88 kD (U) and 88 kD (L), as indicated by the arrows. Immunoblotting of the two-dimensional gel with peptide antibodies to the N-terminal of BEIIa (3KLH) and to the N-terminus of the wheat BEIIb cDNA sequence (R6; see FIGS. 12 and 13 for details of the antibodies are set out in Example 8) indicated preferential binding of the R6 antibody to 88 kD (U) and preferential binding of 3KLH to 88 kD (L) (FIG. 17, Panel B), providing a provisional assignment of these proteins as BEIIb and BEIIa respectively.

The proteins were further analysed by digestion with trypsin, and the peptides released were identified by MALDI-TOF analysis at the Australian Proteome Analysis Facility, Macquarie University, Sydney. The results of this analysis, shown in Table 2, demonstrated that 88 kD (U) was the product of the wheat BEIIb gene, and that while the assignment of 88 kD (L) was inconclusive, the results were consistent with the protein being a branching enzyme encoded by either SBE9 or the wheat BEIIb cDNA.

TABLE 2

(a) Comparison of 88 kD (U) and the predicted
protein encoded by the wheat BEIIb cDNA.
Matches: 6
MOWSE Score: 4.97e+001
Coverage: 8.85%
Matching Peptides:

| MW | Delta | Start | End | Sequence | SEQ ID NO: |
|---|---|---|---|---|---|
| 755.4766 | −0.13 | 320 | 325 | (K) RPKSLR (I) | 38 |
| 1337.7092 | 0.01 | 453 | 463 | (R) VFNYGNKEVIR (F) | 39 |
| 1337.6728 | −0.03 | 703 | 713 | (R) RFDLGDAEFLR (Y) | 40 |
| 1508.7623 | −0.12 | 785 | 799 | (K) VVLDSDAGLFGGFGR (I) | 41 |
| 1589.6933 | −0.08 | 731 | 743 | (K) YGFMTSDHQYVSR (K) | 42 |
| 1692.7049 | −0.17 | 184 | 198 | (R) SDIDEHEGGMDVFSR (G) | 43 |
| 1706.8740 | −0.04 | 340 | 353 | (K) INTYANFRDEVLPR (I) | 44 |

(b) Comparison of 88 kD (L) and the predicted
proteins encoded by the wheat BEIIb cDNA and SBE9 cDNA.
Matches to wheat BEIIb cDNA
Matches: 8
MOWSE Score: 1.32e+003
Likelihood: 2.053 + 003
Coverage: 11.72%
Matching Peptides:

| MW | Delta | Start | End | Sequence | SEQ ID NO: |
|---|---|---|---|---|---|
| 819.4603 | 11.23 | 464 | 470 | (R) FLLSNAR (W) | 45 |
| 1210.5090 | −105.27 | 444 | 452 | (R) GHHWMWDSR (V) | 46 |
| 1337.7092 | 10.53 | 453 | 463 | (R) VFNYGNKEVIR (F) | 39 |
| 1337.6728 | −16.68 | 703 | 713 | (R) RFDLGDAEFLR (Y) | 40 |
| 1508.7623 | −44.33 | 785 | 799 | (K) VVLDSDAGLFGGFGR (I) | 41 |
| 1573.7446 | −16.81 | 326 | 339 | (R) IYETHVGMSSPEPK (I) | 47 |
| 1589.6933 | −23.46 | 731 | 743 | (K) YGFMTSDHQYVSR (K) | 42 |
| 1692.7049 | −95.07 | 184 | 198 | (R) SDIDEHEGGMDVFSR (G) | 43 |
| 1706.8740 | −15.57 | 340 | 353 | (K) INTYANFRDEVLPR (I) | 44 |

Matches to wheat SBE9
Matches: 6
MOWSE Score: 1.04e+001
Coverage: 8.63%
Matching Peptides:

| MW | Delta | Start | End | Sequence | SEQ ID NO: |
|---|---|---|---|---|---|
| 819.4603 | 11.23 | 451 | 457 | (R) FLLSNAR (W) | 45 |
| 1210.5090 | −105.27 | 431 | 439 | (R) GHHWMWDSR (V) | 46 |
| 1508.7875 | −27.64 | 145 | 156 | (K) IYEIDPTLKDFR (S) | 48 |
| 1573.7446 | −16.81 | 313 | 326 | (R) IYESHIGMSSPEPK (I) | 49 |
| 1599.7641 | −9.93 | 171 | 185 | (R) AAIDQHEGGLEAFSR (G) | 50 |
| 1692.8583 | −4.45 | 327 | 340 | (K) INSYANFRDEVLPR (I) | 51 |

EXAMPLE 10

Sequencing of the SBE IIb Gene

A partial genomic sequence of the SBEIIb gene was obtained, using clone G5 described in Example 4. So far approximately 8.4 kb of sequence has been obtained. This includes approximately 500bp upstream of the start codon, presumably comprising the promoter region, and exons 1 to 14 in full. This partial sequence is set out in SEQ ID NO:10. From the sequences of the corresponding maize and *Arabidopsis* BEII genes, we would expect the gene to contain 22 exons. A comparison between the exon/intron structures of various BEII genes and the wheat BEIIb gene is shown in FIG. 18, and the sizes of the exons in various SBEII genes are compared in Table 3. In this table "Arab" represents *Arabidopsis*.

TABLE 3

Sizes of exons in various SBE IIb genes

| Exon no | Arab21 | Arab22 | Wheat BEIIa | Maize BEIIb | Barley BEIIb | Wheat BEIIb |
|---|---|---|---|---|---|---|
| 1 | 42 | 124 | 279 | 212 | 121 | 148 |
| 2 | 253 | 120 | 98 | 146 | 152 | 146 |
| 3 | 236 | 182 | 243 | 155 | 230 | 230 |
| 4 | 99 | 99 | 99 | 99 | 99 | 99 |
| 5 | 43 | 43 | 43 | 43 | 43 | 43 |
| 6 | 60 | 60 | 60 | 60 | | 60 |
| 7 | 81 | 81 | 81 | 81 | | 81 |
| 8 | 117 | 117 | 117 | 117 | | 117 |
| 9 | 84 | 84 | 84 | 84 | | 84 |
| 10 | 122 | 122 | 122 | 122 | | 122 |
| 11 | 120 | 120 | 120 | 120 | | 120 |
| 12 | 130 | 130 | 130 | 130 | | 130 |
| 13 | 111 | 111 | 111 | 111 | | 111 |
| 14 | 129 | 129 | 129 | 129 | | 129 |
| 15 | 104 | 104 | 104 | 104 | | |
| 16 | 145 | 145 | 145 | 145 | | |
| 17 | | 148 | 148 | 148 | | |
| 18 | | 101 | 101 | 101 | | |
| 19 | | 78 | 78 | 78 | | |
| 20 | | 156 | 156 | 156 | | |
| 21 | | 75 | 75 | 75 | | |
| 22 | | 90 | 384 | 304 | | |
| 17 | 558 | | | | | |
| 18 | 164 | | | | | |

Using a probe specific for the 3' end of SBE IIb, three clones designated G7, G8 and G9 respectively, have now been isolated from the *T. tauschii* genomic library, and are being subjected co sequence analysis to provide the 3' region of the gene.

EXAMPLE 11

Development of PCR Primer Sets for the Discrimination of the BEIIb Genes from each Genome A number of primer sets, designed on the basis of comparisons between SBE IIa and SBE IIb genes, were tested on wheat genomic DNA. The sequences of these primers were as follows:

```
                                          SEQ ID NO: 11
ARA 12F:    5' CCG TCC TAC ATG ACA CCT GGC CG 3'

SEQ ID NO: 12
ARA 10R:    5' CCG CCG GAT CGA GGA GCC GAC GG 3'

SEQ ID NO: 13
ARA 6F:     5' GGC GGC GGC GAC GGG ATG GCT GC 3'

SEQ ID NO: 14
ARA 8R:     5' CGC CGT CAG GGA TCA TCA CCT CC 3'

SEQ ID NO: 15
ARA 19F:    5' CAC CCA TTG TAA TTG GGT ACA CTG 3'

SEQ ID NO: 16
ARA 15R:    5' TCC ATG CCT CCT TCG TGT TCA TCA 3'

SEQ ID NO: 17
ARA 23R:    5' CTG CGC ATA AAT CCA AAC TTC TCG 3'
```

Targeting the promoter region of SBE IIb using the primers ARA 12F and ARA 13R resulted in the specific amplification of only the D genome gene. Aneuploid analysis using this pair of primers showed that the SBE IIb was located on the long arm of chromosome 2 in wheat, as ilisutrated in FIG. 19.

The primers ARA6F and ARA8R, which amplify the exon 1-intron 1-exon 2 region of SBE IIb, could distinguish the D genome from the A and B genomes, as shown in FIG. 20. Sequence analysis of this region indicated that the genes from the A and B genomes completely lack intron 1. This is illustrated in FIG. 21.

EXAMPLE 12

Identification of SBE IIb in Genomes A, B and D

Sequence analysis of the intron 3 region of SBE IIb, amplified by PCR using the primers ARA 19F and ARA 15R, followed by digestion using the restriction enzyme Rsa1, revealed significant polymorphism amongst the three genomes. This polymorphism, illustrated in the seqnuce alignment set out in FIG. 22, was utilised to develop genome specific markers which can distinguish between the A, B and D genomes.

PCR amplification of the SBE IIb gene was carried out using the primers ARA 19F and ARA 15R, followed by restriction digestion using Rsa1. The results of the PCR analysis, shown in FIG. 23, indicate that these primers can distinguish between the three genomes.

Screening of approximately 600 wheat lines using the genome specific primer pair, ARA 19F and ARA 23R, which amplifies the same region as ARA 19F and ARA 15R, identified one null mutant of the wheat genome. The amplification was performed as described for FIG. 23, and the results are shown in FIG. 24.

EXAMPLE 13

Constructs for Expression of BEII Genes

Recombinant DNA technology may be used to inhibit or abolish expression of either or both of BE IIa and BE IIb. Three general approaches are used, using transformation of the target plant cells with one of the following types of construct:

a) 'Antisense' constructs of SBE IIa and SBE IIb, in which the desired nucleic acid sequence is inserted into the construct in the opposite direction to the functional gene.

b) 'Sense' constructs of SBE IIa and SBE IIb, in which the desired nucleic acid is inserted in the same direction as the functional gene; this utilises co-suppression events to inhibit the expression of the target gene;

c) Duplex constructs of SBE IIa and SBE IIb, in which the desired nucleic acid in both the sense and antisense orientations is co-located in the construct on either side of a "spacer" loop formed by an intron sequence.

In all three cases, the desired nucleic acid is operably linked to a promoter sequence in the construct.

Sense and antisense constructs have been widely used to modulate gene expression in plants. More recently, it has been shown that the delivery of RNAs with potential to form duplexes is a particularly efficient strategy for generating post-transcriptional gene silencing in transgenic plants (Waterhouse at al., 1998; Smith et al., 2000).

Transformation of the target wheat cells, or cells of other plants, using these constructs is effected using methods known in the art, such as transformation with *Agrobacterium tumefaciens*. Once transgenic plants are obtained, they are assessed for the effects of the transgenes on BE IIa and BE IIb expression. For example, in both maize and potato it has been shown that crossing BE II mutations or BE II transgenes into BE I-deficient backgrounds greatly increases amylose content. Wheat BE I null lines, identified using the methods described in WO99/14314, provide a ready source of BE I-deficient genetic material into which BE IIa and BE IIb transgenics can be crossed, in order to extend further the range of starches which can be produced.

Sense, antisense and duplex constructs of SBE IIa and SBE IIb were generated in the vector pDV03000 (Biogemma Ltd, UK) which carries the high molecular weight gluten promoter (pHMWG) and the Nopaline synthase (Nos) terminator. These constructs are schematically represented in FIGS. 25, 26 and 27. The Biogemma vectors are based on the well-known plasmid pBR322, and comprise a number of restriction sites, as illustrated in FIGS. 25 and 26, for incorporation of desired DNA sequences. The entire desired DNA, plus the promoter and terminator sequences referred to above, can then be excised as a Xho fragment and cloned into a suitable vector, such as *Agrobacterium tumefaciens*. Those skilled in the art will be aware of other suitable vectors which could be used.

SBE IIa Constructs

A sense construct of SB IIa was prepared by inserting a 2143bp fragment of SBE IIa coding sequence in the sense orientation at the EcoR1/Sma1 site of pDV03000. An SBE IIa antisense construct was prepared by inserting 1913 bp of SBE IIa coding sequence in the antisense orientation at the EcoR1/BamH1 site of pDV03000. This is also illustrated in FIG. 25.

SBE IIb Constructs

A sense construct of SBE IIb was generated by inserting a 1008 bp fragment of the SBE IIb coding sequence in the sense orientation at the EcoR1/Sma1 site of pDV03000. An antisense SBE IIb construct was prepared by inserting a 955 bp sequence of the coding region for SBE IIb at the BamH1/Pst1 site of pDV03000 in the antisense orientation. This is illustrated in FIG. 26.

Duplex Constructs

A schematic model of a duplex construct is set out in FIG. 27. The duplex construct was prepared using the following protocol, in which all the amplification steps were performed using PCR under conventional conditions.

SBE IIa Duplex 1) a 468 bp sequence of SBE IIa, which includes the whole of exons 1 and 2 and part of exon 3, with EcoR1 and Kpn1 restriction sites on either side, was amplified to obtain a first fragment (fragment 1);

2) a second fragment, 512 bp in length, consisting of part of exons 3 and 4, and the whole of intron 3 of SBE IIa, with Kpn1 and Sac1 sites on either side, was amplified to provide fragment 2;

3) a 528 bp fragment consisting of the complete exons 1, 2 and 3 of SBE IIa, with BamH1 and Sac1 sites on either side, was amplified to provide fragment 3;

4) fragments 1, 2 and 3 were ligated so that the sequence of fragment 3 was ligated to fragment 2 in the antisense orientation to fragment 1.

SBE IIb Duplex 1) a 471 bp sequence consisting of the whole of exons 1 and 2 and part of exon 3 of SBE IIb was amplified with EcoRI and KpnI restriction sites on either side to generate fragment 1;

2) a 589 bp fragment consisting of part of exons 3 and 4 and the whole of intron 3 of SBE IIb, with Kpn1 and Sac1 sites on either side, was amplified to provide fragment 2;

3) a 528 bp fragment consisting of the complete exons 1, 2 and 3, with BamH1 and Sac1 sites on either side was amplified to provide fragment 3;

4) fragments 1, 2 and 3 were ligated so that fragment 3 was in the antisense orientation to fragment 1 when ligated to fragment 2.

The start and end points of the sequences used for making the constructs were as follows:

a) SBE IIa Sense Construct
Start: 461bp of Sbe 9 (SBE IIa) cDNA
End: 2603bp of Sbe 9 (SBE IIa) cDNA b) SBE IIa Anti-Sense Construct
Start: 691bp of Sbe 9 (SBE IIa) cDNA
End: 2603bp of Sbe 9 (SBE IIa) cDNA This fragment was ligated in the anti-sense orientation.

c) SBE IIb Sense Construct
Start: 85bp of SBE IIb cDNA
End: 1085bp of SBE IIb cDNA d) SBE IIb Anti-Sense Construct
Start: 153bp of SBE IIb cDNA
End: 1085bp of SBE IIb cDNA This fragment was ligated in the anti-sense orientation.

e) SBE IIa Duplex Construct i) Fragment 1
Full exon 1: 1151bp-1336bp of SBE IIa genomic sequence
Full exon 2: 1664bp-1761bp of SBE IIa genomic sequence
Partial exon 3: 2038bp-2219bp of SBE IIa genomic sequence This fragment had an EcoR1 site (GAATTC) introduced at the start of the exon 1 sequence and a KpnI site (GGTACC) introduced at the end of the partial exon 3 sequence.

ii) Fragment 2
Partial exon 3: 2220bp-2279bp of SBE IIa genomic sequence
Full intron 3: 2280bp-2680bp of SBE IIa genomic sequence
Partial exon 4: 2681bp-2731bp of SBE IIa genomic sequence This fragment had a KpnI site (GGTACC) introduced at the start of the partial exon 3 and a SacI site (GAGCTC) introduced at the end of the partial exon 4 sequence.

iii) Fragment 3
  Full exon 1: 1151bp-1336bp of SBE IIa genomic sequence
  Full exon 2: 1664bp-1761bp of SBE IIa genomic sequence
  Full exon 3: 2038bp-2279bp of SBE IIa genomic sequence This fragment had a BamH1 site (GGATCC) introduced at the start of the complete exon 1 sequence and a Sac1 site (GAGCTC) introduced at the end of the complete exon 3 sequence.

f) SBE IIb Duplex Construct i) Fragment 1
  Full exon 1: 489bp-640bp of SBE IIb genomic sequence
  Full exon 2: 789bp-934bp of SBE IIb genomic sequence
  Partial exon 3: 1598 bp-1770 bp of SBE IIb genomic sequence This fragment had an EcoR1 site (GAATTC) introduced at the start of exon 1 and a Kpn1 site (GGTACC) introduced at the end of the partial exon 3 sequence.

ii) Fragment 2
  Partial exon 3: 1771bp-1827bp of SBE IIb genomic sequence
  Full intron 3: 1828bp-2292bp of SBE IIb genomic sequence
  Partial exon 4: 2293bp-2359bp of SBE IIb genomic sequence This fragment had a Kpn1 site (GGTACC) introduced at the start of the partial exon.3 sequence and a Sac1 site (GAGCTC) introduced at the end of the partial exon 4 sequence.

iii) Fragment 3
  Full exon1: 489bp-640bp of SBE IIb genomic sequence
  Full exon 2: 789bp-934bp of SBE IIb genomic sequence
  Full exon 3: 1598bp-1827bp of SBE IIb genomic sequence This fragment had a BamH1 site (GGATCC) introduced at the start of exon 1 and a Sac1 site (GAGCTC) introduced at the end of exon 3.

The SBE IIa and SBE IIb duplexes thus formed were respectively inserted at the EcoR1/BamH1 site of pDV03000.

Samples of λ phage clones G5 and G9 have been deposited in the Australian Government Analytical Laboratories, acting as an International Depository Authority under the Budapest Treaty on 20 Feb. 2001, under accession numbers NM01/19255 and NM01/19256 respectively.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Ali, S., Holloway B., and Taylor W. C., W. C. 2000 Plant Molecular Biology Report 18 123-132.

Baba, T., K. Kimura, K. Mizuno, H. Etoh, Y. Ishida, O. Shida, and Y. Arai. 1991. Sequence conservation of the catalytic regions of amylolytic enzymes in maize branching enzyme-I. Bioc Biop R 181: 87-94.

Baecker P A, Greenberg E, Preiss J (1986). Biosynthesis of the bacterial glucan: primary structure of Escherichia coli 1,4 alpha D glucan 6-alpha-D-(1,4 alpha-D-glucano)-transferase as deduced from the nucleotide sequence of the g1gB gene. J. Biol. Chem. 261, 8738-8743.

Baga, M., A. Repellin, T. Demeke, K. Caswell, N. Leung, E. S. M. Abdel-aal, P. Hucl, and R. N. Chibbar. 1999. Wheat starch modification through biotechnology. STARCH-STARKE 51: 111-116.

Bhattacharyya, M., A. M. Smith, T. H. N. Ellis, C. Hedley, and C. Martin. 1990. The wrinkled-seed character of pea described by Mendel is caused by a transposon-like insertion in a gene encoding starch-branching enzyme. Cell 60: 115-122.

Boyer, C. D., P. A. Damewood, and E. K. G. Simpson. 1980. Effect of gene dosage at high amylose loci on the properties of the amylopectin fractions of the starches. Starch 32: 217-222.

Boyer, C. D. and J. Preiss. 1981. Evidence for independent genetic control of themultiple forms of maize endosperm branching enzymes and starch synthases. Plant Physiology 67: 1141-1145.

Burton, R. A., J. D. Bewley, A. N. Smith, M. K. Bhattacharyya, H. Tatge, S. Ring, V. Bull, W. O. Hamilton, and C. Martin. 1995. Starch branching enzymes belonging to distinct enzyme families are differentially expressed during pea embryo development. Plant J. 7: 3-15.

Cangiano G, La Volpe A, Poulsen P, Kreiberg J D (1993) Starch branching enzyme cDNA from *Solanum tuberosum*. Plant Physiol 102: 1053-1054.

Cao, H. P., J. Imparl-Radosevich, H. P. Guan, P. L. Keeling, H. G. James, and A. M. Myers. 1999. Identification of the soluble starch synthase activities of maize endosperm. Plant Physiology 120: 205-215.

Denyer, K., C. M. Hylton, C. F. Jenner, and A. M. Smith. 1995. Identification of multiple isoforms of soluble and granule-bound starch synthase in developing wheat endosperm. Planta 196: 256-265.

Devereaux, J, Haeberli P, Smithies O (1984) A comprehensive set of sequence analysis programs for the VAX. Nucleic Acids Res 12; 387-395

Filpse, E., L. Suurs, and R. G. F. Visser. 1996. Introduction of sense and antisense cDNA for branching enzyme in the amylose-free potato mutant leads to physico-chemical changes in the starch. Planta 198: 340.

Fisher, D. K., M. Gao, K. N. Kim, C. D. Boyer, and M. J. Guiltinan. 1996. Two closely related cDNAs encoding starch branching enzyme from *Arabidopsis thaliana*. Plant Mol Biol 30: 97-108.

Fisher, D. K., M. Gao, K.-N. Kim, C. D. Boyer, and M. J. Guiltinan, 1996. Allelic analysis of the maize amylose-extender locus suggests that independent genes encode starch-branching enzymes IIa and IIb. Plant Physiology 110: 611-619.

Fisher, D. K., C. D. Boyer, and L. C. Hannah. 1993. Starch branching enzyme II from maize endosperm. Plant Physiology 102: 1045-1046.

Gao, M., D. K. Fisher, K. N. Kim, J. C. Shannon, and M. J. Guiltinan. 1996. Evolutionary conservation and expression patterns of maize starch branching enzyme I and IIb genes suggests isoform specialization. Plant Mol Biol 30: 1223-1232.

Gao, M., J. Wanat, P. S. Stinard, M. G. James, and A. M. Myers. 1998. Characterization of dull1, a maize gene coding for a novel starch synthase. Plant Cell 10: 399-412.

Gao, M., D. K. Fisher, K. N. Kim, J. C. Shannon, and M. J. Guiltinan. 1997, Independent genetic control of maize starch-branching enzymes IIa and IIb—Isolation and characterization of a Sbe2a cDNA. Plant Physiology 114: 69-78.

Higgins T J V, Zwar J A, Jacobsen J V (1976) Gibberellic acid enhances the level of translatable mRNA for a amylase in barley aleurone layers. Nature 260: 166-168.

Jähne A., Lazzeri P. A. and Lörz H. (1991) Regeneration of fertile plants from protoplasts derived from embryonic cell suspensions of barley (*Hordeum vulgare* L.). *Plant Cell Reports* 10, 1-6.

Jobling, S. A., G. P. Schwall, R. J. Westcott, C. M. Sidebottom, M. Debet, M. J. Gidley, R. Jeffcoat, and R. Safford. 1999. A minor form of starch branching enzyme in potato (*Solanum tuberosum* L.) tubers has a major effect on starch structure: cloning and characterization of multiple forms of SBE A. Plant J 18: 163-171.

Kawasaki, T., K. Mizuno, T. Baba, and H. Shimada. 1993. Molecular analysis of the gene encoding a rice starch branching enzyme. Molecular and General Genetics 237: 10-16.

Khoshnoodi, J., A. Blennow, B. Ek, L. Rask, and H. Larsson. 1996. The multiple forms of starch-branching enzyme I in *Solanum tuberosum*. Eur J Biochem 242: 148-155.

Kiel J A K W, Boels J M, Beldman G, Venema G. (1992). The glgB gene from the thermophile *Bacillus caldolyticus* encodes a thermolabile branching enzyme. DNA Seq 3, 221-232.

Kim, K. N., D. K. Fisher, M. Gao, and M. J. Guiltinan. 1998. Genomic organization and promoter activity of the maize starch branching enzyme I gene. Gene 216: 233-243.

Kim, K. N., D. K. Fisher, M. Gao, and M. J. Guiltinan. 1998. Molecular cloning and characterization of the amylose-extender gene encoding starch branching enzyme IIB in maize. Plant Mol Biol 38: 945-956.

Lazzeri, P. A., Brettschneider, R., Luhsrs, R., and Lorz. H. Theor. Appl. Genet. 1991, 81, 437-444.

Lagudah E S, Appels R, McNeil D (1991) The Nor-D3 locus of *Triticum tauschii*: natural variation and genetic linkage to markers in chromosome 5. Genome 34: 387-395.

Li, Z., S. Rahman, B. Kosar-Hashemi, G C Mouille, R. Appels, and M. K. Morell. 1999. Cloning and characterization of a gene encoding wheat starch synthase I. Theor Appl Genet 98: 1208-1216.

Li, Z. Y., X. S. Chu, G. Mouille, L. L. Yan, B. Kosar-Hashemi, S. Hey, J. Napier, P Shewry, B. Clarke, R. Appels, M. K. Morell, and S. Rahman 1999. The localization and expression of the class II starch synthases of wheat. Plant physiology. 120: 1147-1155.

Maniatis T, Fritsch E F, Maniatis J (1982) *Molecular cloning. A Laboratory Manual*. New York. Cold Spring Harbor Laboratory.

Matsumoto, A., T. Nakajima, and K. Matsuda. 1990. A kinetic study of the interaction between glycogen and *Neurospora crassa* branching enzyme. J Biochem 107: 123-126.

Mizuno, K., T Kawasaki, H. Shimada, H. Satoh, E. Kobayashi, S. Okumura, Y. Arai, and T. Baba. 1993. Alteration of the structural properties of starch components by the lack of an isoform of starch branching enzyme in rice seeds. J Biol Chem 268: 19084-19091.

Morell. M. K., A. Blennow, B. Kosar-Hashemi, and M. S. Samuel. 1997. Differential expression and properties of starch branching enzyme isoforms in developing wheat endosperm. Plant Physiology 113: 201-208.

Nair, R. B., M. Baga, G J. Scoles, K. K. Kartha, and R. N. Chibbar. 1997. Isolation, characterization and expression analysis of a starch branching enzyme II cDNA from wheat. Plant Science 122: 153-163.

Rahman, S., S. Abrahams, D. Abbott, Y. Mukai, M. Samuel, M. Morell, and R. Appels. 1997. A complex arrangement of genes at a starch branching enzyme I locus in the D-genome donor of wheat. Genome 40: 465-474.

Rahman, S., Z. Li, S. Abrahams, D. Abbott, R. Appels, and M. K. Morell. 1999. Characterisation of a gene encoding wheat endosperm starch branching enzyme-I. Theor Appl Genet 98: 156-163.

Rahman, S., B. Kosar-Hashemi, M. S. Samuel, A. Hill, D. C. Abbott, J. H. Skerritt, J. Preiss, R. Appels, and M. K. Morell. 1995. The major proteins of wheat endosperm starch granules Aust J Plant Phys 22: 793-803.

Safford, R., S. A. Jobling, C. M. Sidebottom, R. J. Westcott, D. Cooke, K. J. Tober, B. H. Strongitharm, A. L. Russell, and M. J. Gidley. 1998. Consequences of antisense RNA inhibition of starch branching enzyme activity on properties of potato starch. Carbohydrate polymers 35: 155-168.

Sathish, P., C. X. Sun, A. Deiber, C. Jansson, and C. X. Sun. Cloning and anti-sense RNA constructs of a starch branching enzyme gene from barley endosperm. Mathis, P. 313-316. 1995. Photosynthesis: from light to biosphere. Volume V. Proceedings of the Xth International Photosynthesis Congress, Montpellier, France, 20-25 Aug. 1995.

Schondelmaier, J., A. Jacobi, G. Fischbeck, and A. Jahoor. 1992. Genetical Studies on the mode of inheritance and localization of the amol (High Amylose) gene in barley. Plant Breeding 109: 274-280.

Smith, N. A., Singh S. P., Wang M. B., Stoutjesdijk P. A., Green A. G., Waterhouse P. M. (2000) Nature 407, 319-420.

Sun, C. X., P. Sathish, B. Ek, A. Deiber, C. Jansson, and C. X. Sun 1996. Demonstration of in vitro starch branching enzyme activity for a 51/50-kDa polypeptide isolated from developing barley (*Hordeum vulgare*) caryopses. Physiologia. Plantarum. 96: 474-483.

Sun, C. X., P. Sathish, S. Ahlandsberg, A. Dieber, C. Jansson, and C. X. Sun. 1997. Identification of four starch-branching enzymes in barley endosperm: partial purification of forms I, Ia and IIb. New Phytologist 137: 215-222.

Sun, C. X, P. Sathish, S. Ahlandsberg, C. Jansson, and C. X. Sun. 1998. The two genes encoding starch-branching enzymes IIa and IIb are differentially expressed in barley Plant Physiology. 118: 37-49.

Takaoka, M., S. Watanabe, H. Sassa, M. Yamamori, T. Nakamura, T. Sasakuma, and H. Hirano. 1997. Structural characterization of high molecular weight starch granule-bound proteins in wheat (*Triticum aestivum* L). J. Agric. Food Chem. 45: 2929-2934.

Tingay, S., McElroy, D., Kalla, R., Fieg, S., Wang. M, Thornton, S. and Brettel, R. 1997, The Plant Journal, 11, 1369-1376.

Wan Y., and Lemaux, P. G. 1994, Plant Physiology. 104, 37-48.

Wirtzens, B, Brettel R I S, Murray F., McElroy D, Li Z, Dennis E S (1998) Comparison of three selectable marker genes for transformation of wheat by microprojectile bombardment. Aust. J. Plant. Physiol. 25, 39-44.

Waterhouse P. M., Graham M. W., Wang M. B. (1998). Virus resistance and gene silencing can be induced by simultaneous expression of sense and antisense RNA. Proc. Natl. Acad. Sci. USA. 95, 13959-13964.

Yamamori, M. and T. R. Endo. 1996. Variation of starch granule proteins and chromosome mapping of their coding genes in common wheat. Theor Appl Genet 93: 275-281.

The invention claimed is:

1. A wheat plant comprising a null allele of a gene on a long arm of chromosome 2 encoding wheat starch branching enzyme IIb (BEIIb), in combination with one or more null alleles of genes which encode starch branching enzyme IIa (BEIIa), granule bound starch synthase (GBSS), starch synthase II (SSII) or starch branching enzyme I (BEI).

2. The wheat plant of claim 1, wherein the gene encoding BEIIb is a wSBEII gene on a long arm of chromosome 2D.

3. The wheat plant of claim 1, wherein the gene encoding BEIIb corresponds to the partial BEIIb gene present on λ phage clone G5, wherein a sample of G5 has been deposited with the Australian Government Analytical Laboratories under Accession No. NM01/19255.

4. The wheat plant of claim 2, wherein the wSBEII gene comprises introns of the following sizes: intron 1, 148 base pairs; intron 2, 663 base pairs; intron 3, 465 base pairs; intron 4, 74 base pairs; intron 5, 181 base pairs; intron 6, 442 base pairs; intron 7, 79 base pairs; and intron 8, 178 base pairs.

5. The wheat plant of claim 1, wherein the gene encoding BEIIb encodes an RNA corresponding to a cDNA having a nucleotide sequence as set forth in SEQ ID NO: 6.

6. The wheat plant of claim 1, further comprising a null allele of a second gene encoding BEIIb.

7. The wheat plant of claim 1, wherein the grain of the plant comprises an altered amylose-to-amylopectin ratio.

8. The wheat plant of claim 2, further comprising a null allele of a second gene encoding BEIIb.

9. The wheat plant of claim 1, comprising more than one null alleles of genes which encodes BEIIa.

* * * * *

SEQUENCE LISTING

<160> NUMBER OF SEQ ID NOS: 51

<210> SEQ ID NO 1
<211> LENGTH: 2726
<212> TYPE: DNA
<213> ORGANISM: Triticum sp.

<400> SEQUENCE: 1

| | | | | | |
|---|---|---|---|---|---|
| acgttgctcc | cccttctcat | cgcttctcaa | ttaatatctc | catcactcgg | ttccgcgctg | 60 |
| catttcggcc | ggcgggttga | gtgagatctg | ggccactgac | cgactcactc | gctcgctgcg | 120 |
| gggatggcga | cgttcgcggt | gtccggcgcg | accctcggtg | tggcgcggcc | gccggcggcg | 180 |
| gcgcaacctg | aagaattaca | gatacctgaa | gacatcgagg | agcaaacggc | tgaagtaaac | 240 |
| atgacagggg | ggactgcaga | aaaacttgaa | tcttcagaac | cgactcaagg | cattgtggaa | 300 |
| acaatcactg | atggtgtaac | caaggagtt | aaggaactag | tcgtggggga | gaaaccgcga | 360 |
| gttgtcccaa | aaccaggaga | tgggcagaaa | atatacgaga | ttgacccaac | gctgaaagat | 420 |
| tttcggagcc | atcttgacta | ccgatacagc | gaatacagga | gaattcgtgc | tgctattgac | 480 |
| caacatgaag | gtggattgga | agcattttct | cgtggttatg | aaaagcttgg | atttacccgc | 540 |
| agtgctgaag | gtatcactta | ccgagaatgg | gctcctggag | cgcattctgc | agcattagta | 600 |
| ggtgacttca | acaattggaa | tccgaatgca | gatactatga | ccagagatga | ttatggtgtt | 660 |
| tgggagattt | tcctccctaa | caatgctgat | ggatccccag | ctattcctca | tggctcacgt | 720 |
| gtaaagatac | ggatggatac | tccatctggt | gtgaaggatt | caatttctgc | ttggatcaag | 780 |
| ttctctgtgc | aggctccagg | tgaaatacca | ttcaatggca | tatattatga | tccacctgaa | 840 |
| gaggagaagt | atgtcttcca | acatcctcaa | cctaaacgac | cagagtcact | gaggatttat | 900 |
| gaatcacaca | ttggaatgag | cagcccagaa | ccgaagataa | attcatatgc | taattttagg | 960 |
| gatgaggtgc | tgccaagaat | taaaaggctt | ggatacaatg | cagtgcagat | aatggcaatc | 1020 |
| caggagcatt | catactatgc | gagctttggg | taccatgtta | ctaattttt | tgcaccaagt | 1080 |
| agccgttttg | gaactccaga | ggacttaaaa | tccctgatcg | atagagcaca | tgagcttggt | 1140 |
| ttgcttgttc | ttatggatat | tgttcatagt | cattcatcaa | ataatacccct | tgacggcttg | 1200 |
| aatggtttcg | atggcactga | tacacattac | ttccacggtg | gtccacgtgg | ccatcattgg | 1260 |
| atgtgggatt | ctcgtctatt | caactatggg | agttgggaag | tattgagatt | cttactgtca | 1320 |
| aacgcgagat | ggtggcttga | agaatataag | tttgatggat | ttcgatttga | tggggtgacc | 1380 |
| tccatgatgt | atactcacca | tggattacaa | atgacatttta | ctgggaacta | tggcgagtat | 1440 |
| tttggatttg | ctactgatgt | tgatgcggta | gtttacttga | tgctggtcaa | cgatctaatt | 1500 |
| catggacttc | atcctgatgc | tgtatccatt | ggtgaagatg | tcagtggaat | gcccacattt | 1560 |
| tgcatccctg | ttcagatgg | tggtgttggt | tttgactatc | gcttgcatat | ggctgtagca | 1620 |
| gataaatgga | ttgaactcct | caagcaaagt | gacgaatctt | ggaaaatggg | tgatattgtg | 1680 |
| cacacccctaa | caaatagaag | gtggcttgag | aagtgtgtaa | cttatgcaga | aagtcatgat | 1740 |
| caagcactag | ttggtgacaa | gactattgca | ttctggttga | tggataagga | tatgtatgat | 1800 |
| ttcatggctc | tggataggcc | ttcaactcct | cgcattgatc | gtggcatagc | attacataaa | 1860 |
| atgatcaggc | ttgtcaccat | gggtttaggt | ggtgaaggct | atcttaactt | catgggaaat | 1920 |
| gagtttgggc | atcctgaatg | gatagatttt | ccaagaggtc | cgcaaactct | tccaaccggc | 1980 |
| aaagttctcc | ctggaaataa | caatagttat | gataaatgcc | gccgtagatt | tgatcttgga | 2040 |

-continued

```
gatgcagatt ttcttagata tcatggtatg caagagttcg atcaggcaat gcagcatctt    2100
gaggaaaaat atgggtttat gacatctgag caccagtatg tttcacggaa acatgaggaa    2160
gataaggtga tcatcttcga aagaggagat ttggtatttg ttttcaactt ccactggagc    2220
aatagctttt ttgactaccg tgttgggtgt tccaggcctg ggaagtacaa ggtggcctta    2280
gactccgacg atgcactctt tggtggattc agcaggcttg atcatgatgt cgactacttc    2340
acaaccgaac atccgcatga caacaggccg cgctctttct cggtgtacac tccgagcaga    2400
actgcggtcg tgtatgccct tacagagtaa gaaccagcag ctgcttgtta caaggcaaag    2460
agagaactcc agagagctcg tggatcgtga gcgaagcgac gggcaacggc gcgaggctgc    2520
tctaagcgcc atgactggga ggggatcgtg cctcttcccc agatgccagg aggagcagat    2580
ggataggtag cttgttggtg agcgctcgaa agaaaatgga cgggcctggg tgtttgtcgt    2640
gctgcactac cctcctccta tcttgcacat tcccggttgt ttttgtacat ataactaata    2700
attgcccgtg cgctcaacgt gaacaa                                        2726
```

```
<210> SEQ ID NO 2
<211> LENGTH: 11476
<212> TYPE: DNA
<213> ORGANISM: Aegilops tauschii
<220> FEATURE:
<221> NAME/KEY: modified_base
<222> LOCATION: (1722)..(1722)
<223> OTHER INFORMATION: a, c, g, or t
<220> FEATURE:
<221> NAME/KEY: modified_base
<222> LOCATION: (4794)..(4794)
<223> OTHER INFORMATION: a, c, g, or t
<220> FEATURE:
<221> NAME/KEY: modified_base
<222> LOCATION: (4972)..(4972)
<223> OTHER INFORMATION: a, c, g, or t
<220> FEATURE:
<221> NAME/KEY: modified_base
<222> LOCATION: (5077)..(5078)
<223> OTHER INFORMATION: a, c, g, or t
<220> FEATURE:
<221> NAME/KEY: modified_base
<222> LOCATION: (5081)..(5081)
<223> OTHER INFORMATION: a, c, g, or t
<220> FEATURE:
<221> NAME/KEY: modified_base
<222> LOCATION: (7009)..(7009)
<223> OTHER INFORMATION: a, c, g, or t
<220> FEATURE:
<221> NAME/KEY: modified_base
<222> LOCATION: (7326)..(7326)
<223> OTHER INFORMATION: a, c, g, or t
<220> FEATURE:
<221> NAME/KEY: modified_base
<222> LOCATION: (7380)..(7380)
<223> OTHER INFORMATION: a, c, g, or t
<220> FEATURE:
<221> NAME/KEY: modified_base
<222> LOCATION: (7383)..(7383)
<223> OTHER INFORMATION: a, c, g, or t
<220> FEATURE:
<221> NAME/KEY: modified_base
<222> LOCATION: (7818)..(7818)
<223> OTHER INFORMATION: a, c, g, or t
<220> FEATURE:
<221> NAME/KEY: modified_base
<222> LOCATION: (8188)..(8188)
<223> OTHER INFORMATION: a, c, g, or t
<220> FEATURE:
<221> NAME/KEY: modified_base
<222> LOCATION: (10458)..(10458)
<223> OTHER INFORMATION: a, c, g, or t
```

<400> SEQUENCE: 2

```
agaaacacct ccatttaga ttttttttt gttcttttcg gacggtgggt cgtggagaga       60
ttagcgtcta gttttcttaa aagaacaggc catttaggcc ctgctttaca aaaggctcaa    120
ccagtccaaa acgtctgcta ggatcaccag ctgcaaagtt aagcgcgaga ccaccaaaac    180
aggcgcattc gaactggaca gacgctcacg caggagccca gcaccacagg cttgagcctg    240
acagcggacg tgagtgcgtg acacatgggg tcatctatgg gcgtcggagc aaggaagaga    300
gacgcacatg aacaccatga tgatgctatc aggcctgatg gagggagcaa ccatgcacct    360
tttcccctct ggaaattcat agctcacact tttttttaat ggaagcaaga gttggcaaac    420
acatgcattt tcaaacaagg aaaattaatt ctcaaaccac catgacatgc aattctcaaa    480
ccatgcaccg acgagtccat gcgaggtgga aacgaagaac tgaaaatcaa catcccagtt    540
gtcgagtcga aagaggatg acactgaaag tatgcgtatt acgatttcat ttacatacat    600
gtacaaatac ataatgtacc ctacaatttg tttttggag cagagtggtg tggtcttttt    660
tttttacacg aaaatgccat agctggcccg catgcgtgca gatcggatga tcggtcggag    720
acgacggaca atcagacact caccaactgc ttttgtctgg gacacaataa atgttttgt     780
aaacaaaata aatacttata aacgagggta ctagaggccg ctaacggcat ggccaggtaa    840
acgcgctccc agccgttggt ttgcgatctc gtcctcccgc acgcagcgtc gcctccaccg    900
tccgtccgtc gctgccacct ctgctgtgcg cgcgcacgaa gggaggaaga acgaacgccg    960
cacacacact cacacacggc acactccccg tgggtcccct ttccggcttg gcgtctatct   1020
cctctccccc gcccatcccc atgcactgca ccgtacccgc cagcttccac ccccgccgca   1080
cacgttgctc ccccttctca tcgcttctca attaatatct ccatcactcg ggttccgcgc   1140
tgcatttcgg ccggcgggtt gagtgagatc tgggcgactg gctgactcaa tcactacgcg   1200
gggatggcga cgttcgcggt gtccggcgcg actctcggtg tggcgcgggc cggcgtcgga   1260
gtggcgcggg ccggctcgga gcggaggggc ggggcggact tgccgtcgct gctcctcagg   1320
aagaaggact cctctcgtac gcctcgctct ctcgaatctc ccccgtctgg ctttggctcc   1380
ccttctctct cctctgcgcg cgcatggcct gttcgatgct gttccccaat tgatctccat   1440
gagtgagaga gatagctgga ttaggcgatc gcgcttcctg aacctgtatt tttttccccg   1500
cggggaaatg cgttagtgtc acccaggccc tggtgttacc acggctttga tcattcctcg   1560
tttcattctg atatatattt tctcattctt tttcttcctg ttcttgctgt aactgcaagt   1620
tgtggcgttt tttcactatt gtagtcatcc ttgcattttg caggcgccgt cctgagccgc   1680
gcggcctctc cagggaaggt cctggtgcct gacggcgaga gngacgactt ggcaagtccg   1740
gcgcaacctg aagaattaca ggtacacaca ctcgtgccgg taaatcttca tacaatcgtt   1800
attcacttac caaatgccgg atgaaaccaa ccacggatgc gtcaggtttc gagcttcttc   1860
tatcagcatt gtgcagtact gcactgcctt gttcattttg ttagccttgg ccccgtgctg   1920
gctcttgggc cactgaaaaa atcagatgga tgtgcattct agcaagaact tcacaacata   1980
atgcaccgtt tggggtttcg tcagtctgct ctacaattgc tatttttcgt gctgtagata   2040
cctgaagata tcgaggagca aacggcggaa gtgaacatga cagggggggac tgcagagaaa   2100
cttcaatctt cagaaccgac tcagggcatt gtggaaacaa tcactgatgg tgtaaccaaa   2160
ggagttaagg aactagtcgt gggggagaaa ccgcgagttg tcccaaaacc aggagatggg   2220
cagaaaatat acgagattga cccaacactg aaagattttc ggagccatct tgactaccgg   2280
taatgcctac ccgctgcttt cgctcatttt gaattaaggt cctttcatca tgcaaatttg   2340
```

```
gggaacatca aagagacaaa gactagggac caccatttca tacagatccc ttcgtggtct    2400
gagaatatgc tgggaagtaa atgtataatt gatggctaca atttgctcaa aattgcaata    2460
cgaataactg tctccgatca ttacaattaa agagtggcaa actgatgaaa atgtggtgga    2520
tgggttatag attttacttt gctaattcct ctaccaaatt cctagggggg aaatctacca    2580
gttgggaaac ttagtttctt atctttgtgg ccttttttgtt ttggggaaaa cacattgcta    2640
aattcgaatg attttgggta tacctcggtg gattcaacag atacagcgaa tacaagagaa    2700
ttcgtgctgc tattgaccaa catgaaggtg gattggaagc attttctcgt ggttatgaaa    2760
agcttggatt tacccgcagg taaatttaaa gctttattat tatgaaacgc ctccactagt    2820
ctaattgcat atcttataag aaaatttata attcctgttt tccctctct tttttccagt    2880 gctgaaggta tcgtctaatt gcatatctta taagaaaatt tatattcctg ttttccccta    2940
ttttccagtg ctgaaggtat cacttaccga gaatgggctc cctggagcgc atgttatgtt    3000
cttttaagtt ccttaacgag acaccttcca atttattgtt aatggtcact attcaccaac    3060
tagcttactg gacttacaaa ttagcttact gaatactgac cagttactat aaatttatga    3120
tctggctttt gcaccctgtt acagtctgca gcattagtag gtgacttcaa caattggaat    3180
ccaaatgcag atactatgac cagagtatgt ctacagcttg gcaattttcc acctttgctt    3240
cataactact gatacatcta tttgtattta tttagctgtt tgcacattcc ttaaagttga    3300
gcctcaacta catcatatca aaatggtata atttgtcagt gtcttaagct tcagcccaaa    3360
gattctactg aatttagtcc atcttttga gattgaaaat gagtatatta aggatgaatg    3420
aatacgtgca acactcccat ctgcattatg tgtgcttttc catctacaat gagcatattt    3480
ccatgctatc agtgaaggtt tgctcctatt gatgcagata tttgatatgg tcttttcagg    3540
atgattatgg tgtttgggag attttcctcc ctaacaacgc tgatggatcc tcagctattc    3600
ctcatggctc acgtgtaaag gtaagctggc caattattta gtcgaggatg tagcattttc    3660
gaactctgcc tactaagggt cccttttcct ctctgttttt tagatacgga tggatactcc    3720
atccggtgtg aaggattcaa tttctgcttg gatcaagttc tctgtgcagg ctccaggtga    3780 aataccttc aatggcatat attatgatcc acctgaagag gtaagtatcg atctacatta    3840
cattattaaa tgaaatttcc agtgttacag tttttaata cccacttctt actgacatgt    3900
gagtcaagac aatactttg aatttggaag tgacatatgc attaattcac cttctaaggg    3960
ctaaggggca accaccttg gtgatgtgtg tatgcttgtg tgtgacataa gatcttatag    4020
ctcttttatg tgttctctgt tggttaggat attccatttt ggccttttgt gaccatttac    4080
taaggatatt tacatgcaaa tgcaggagaa gtatgtcttc caacatctca actaaacgac    4140
cagagtcact aaggatttat gaatcacaca ttggaatgag cagcccggta tgtcaataag    4200
ttatttcacc tgtttctggt ctgatggttt attctatgga ttttctagtt ctgttatgta    4260
ctgttaacat attacatggt gcattcactt gacaacctcg atttttatttt ctaatgtctt    4320 catattggca agtgcaaaac tttgcttcct cttttgtctgc ttgttctttt gtcttctgta    4380
agatttccat tgcatttgga ggcagtgggc atgtgaaagt catatctatt tttttttttgt    4440 cagagcatag ttatatgaat tccattgttg ttgcaatagc tcggtataat gtaaccatgt    4500
tactagctta agatttccca cttaggatgt aagaaatatt gcattggagc gtctccagca    4560
agccatttcc taccttatta atgagagaga gacaagggg ggggggggg gggggttccc    4620 ttcattattc tgcgagcgat tcaaaaactt ccattgttct gaggtgtacg tactgcaggg    4680
```

```
atctcccatt atgaagagga tatagttaat tctttgtaac ctacttggaa acttgagtct    4740
tgaggcatcg ctaatatata ctatcatcac aatacttaga ggatgcatct gaanatttta    4800
gtgtgatctt gcacaggaac cgaagataaa ttcatatgct aattttaggg atgaggtgtt    4860
gccaagaatt aaaaggcttg gatacaatgc agtgcagata atggcaatcc aggagcattc    4920
atactatgca agctttgggt attcacacaa tccatttttt tctgtataca cntcttcacc    4980
catttggagc tattacatcc taatgcttca tgcacataaa atatttggat ataatccttt    5040
attagatata tagtacaact acacttagta ttctgannaa naagatcatt ttattgttgt    5100
tggcttgttc caggtaccat gttactaatt tttttgcacc aagtagccgt tttggaactc    5160
cagaggactt aaaatccttg atcgatagag cacatgagct tggtttgctt gttcttatgg    5220
atattgttca taggtaatta gtccaattta attttagctg ttttactgtt tatctggtat    5280
tctaaaggga aattcaggca attatgatac attgtcaaaa gctaagagtg gcgaaagtga    5340
aatgtcaaaa tctagagtgg cataaggaaa attggcaaaa actagagtgg caaaaataaa    5400
attttcccat cctaaatggc agggccctat cgccgaatat ttttccattc tatataattg    5460
tgctacgtga cttctttttt ctcagatgta ttaaaccagt tggacatgaa atgtatttgg    5520
tacatgtagt aaactgacag ttccatagaa tatcgttttg taatggcaac acaatttgat    5580
gccatagatg tggattgaga agttcagatg ctatcaatag aattaatcaa ctggccatgt    5640
actcgtggca ctacatatag tttgcaagtt ggaaaactga cagcaatacc tcactgataa    5700
gtggccaggc cccacttgcc agcttcatac tagatgttac ttccctgttg aattcatttg    5760
aacatattac ttaaagttct tcatttgtcc taagtcaaac ttctttaagt ttgaccaagt    5820
ctattggaaa atatatcaac atctacaaca ccaaattact ttgatcagat taacaatttt    5880
tattttatta tattagcaca tctttgatgt tgtagatatc agcacatttt tctatagact    5940
tggtcaaata tagagaagtt tgacttagga caaatctaga acttcaatca atttggatca    6000
gagggaacat caaataatat agatagatgt caacacttca acaaaaaaat cagaccttgt    6060
caccatatat gcatcagacc atctgtttgc tttagccact tgctttcata tttatgtgtt    6120
tgtacctaat ctacttttcc ttctacttgg tttggttgat tctatttcag ttgcattgct    6180
tcatcaatga ttttgtgtac cctgcagtca ttcgtcaaat aatacccttg acggtttgaa    6240
tggtttcgat ggcactgata cacattactt ccacggtggt ccacgcggcc atcattggat    6300
gtgggattct cgtctattca actatgggag ttgggaagta tgtagctctg acttctgtca    6360
ccatatttgg ctaactgttc ctgttaatct gttcttacac atgttgatat tctattctta    6420
tgcaggtatt gagattctta ctgtcaaacg cgagatggtg gcttgaagaa tataagtttg    6480
atggatttcg atttgatggg gtgacctcca tgatgtatac tcaccatgga ttacaagtaa    6540
gtcatcaagt ggtttcagta acttttttag ggcactgaaa caattgctat gcatcataac    6600
atgtatcatg atcaggactt tgtgctacgga gtcttagata gttccctagt atgcttgtac    6660
aattttacct gatgagatca tggaagattg gaagtgatta ttatttattt tctttctaag    6720
tttgtttctt gttctagatg acattactg ggaactatgg cgaatatttt ggatttgcta    6780
ctgatgttga tgcggtagtt tacttgatgc tggtcaacga tctaattcat ggactttatc    6840
ctgatgctgt atccattggt gaagatgtaa gtgcttacag tatttatgat ttttaactag    6900
ttaagtagtt ttatttttggg gatcagtctg ttacactttt tgttaggggt aaaatctctc    6960
ttttcataac aatgctaatt tataccttgt atgataatgc atcacttang taatttgaaa    7020
agtgcaaggg cattcaagct tacgagcata ttttttgatg gctgtaattt atttgatagt    7080
```

```
atgcttgttt gggtttttca ataagtggga gtgtgtgact aatgttgtat tatttattta    7140
attgcggaag aaatgggcaa ccttgtcaat tgcttcagaa ggctaacttt gattccataa    7200
acgctttgga aatgagaggc tattcccaag gacatgaatt atacttcagt gtgttctgta    7260
catgtatttg taatagtggt ttaacttaaa ttcctgcact gctatggaat ctcactgtat    7320
gttgtnagtg tacacatcca caaacaagta atcctgagct ttcaactcat gagaaaatan    7380
gangtccgct tctgccagca ttaactgttc acagttctaa tttgtgtaac tgtgaaattg    7440
ttcaggtcag tggaatgcct acattttgca tccctgttcc agatggtggt gttggttttg    7500
actaccgcct gcatatggct gtagcagata aatggattga actcctcaag taagtgcagg    7560
aatattggtg attacatgcg cacaatgatc tagattacat tttctaaatg gtaaaaagga    7620
aaatatgtat gtgaatatct agacatttgc ctgttatcag cttgaatacg agaagtcaaa    7680
tacatgattt aaatagcaaa tctcggaaat gtaatggcta gtgtctttat gctgggcagt    7740
gtacattgcg ctgtagcagg ccagtcaaca cagttagcaa tattttcaga acaatatta    7800 tttatatccg tatatganga agttagtat ataaactgtg gtcattaatt gtgttcacct    7860
tttgtcctgt ttaaggatgg gcagtaggta ataaatttag ccagataaaa taaatcgtta    7920
ttaggtttac aaaaggaata tacagggtca tgtagcatat ctagttgtaa ttaatgaaaa    7980
ggctgacaaa aggctcggta aaaaaaactt tatgatgatc cagatagata tgcaggaacg    8040
cgactaaagc tcaaatactt attgctacta cacagctgcc aatctgtcat gatctgtgtt    8100
ctgctttgtg ctatttagat ttaaatacta actcgataca ttggcaataa taaacttaac    8160
tattcaacca atttggtgga taccaganat ttctgccctc ttgttagtaa tgatgtgctc    8220
cctgctgctg ttctctgccg ttacaaaagc tgttttcagt tttttgcatc attattttg    8280 tgtgtgagta gtttaagcat gttttttgaa gctgtgagct gttggtactt aatacattct    8340
tggaagtgtc caaatatgct gcagtgtaat ttagcatttc tttaacacag gcaaagtgac    8400
gaatcttgga aaatgggcga tattgtgcac accctaacaa atagaaggtg gcttgagaag    8460
tgtgtaactt atgcagaaag tcatgatcaa gcactagttg gtgacaagac tattgcattc    8520
tggttgatgg ataaggtact agctgttact tttggacaaa agaattactc cctcccgttc    8580
ctaaatataa gtctttgtag agattccact atggaccaca tagtatatag atgcatttta    8640
gagtgtagat tcactcattt tgcttcgtat gtagtccata gtgaaatctc tacagagact    8700
tatatttagg aacggaggga gtacataatt gatttgtctc atcagattgc tagtgttttc    8760
ttgtgataaa gattggctgc ctcacccatc accagctatt tcccaactgt tacttgagca    8820
gaatttgctg aaaacgtacc atgtggtact gtggcggctt gtgaactttg acagttatgt    8880
tgcaattttc tgttcttatt tatttgattg cttatgttac cgttcatttg ctcattcctt    8940
tccgagacca gccaaagtca cgtgttagct gtgtgatctg ttatctgaat cttgagcaaa    9000
ttttattaat aggctaaaat ccaacgaatt atttgcttga atttaaatat acagacgtat    9060
agtcacctgg ctctttctta gatgattacc atagtgcctg aaggctgaaa tagttttggt    9120
gtttcttgga tgccgcctaa aggagtgatt tttattggat agattcctgg ccgagtcttc    9180
gttacaacat aacattttgg agatatgctt agtaacagct ctgggaagtt tggtcacaag    9240
tctgcatcta cacgctcctt gaggttttat tatggcgcca tctttgtaac tagtggcacc    9300
tgtaaggaaa cacattcaaa aggaaacggt cacatcattc taatcaggac caccatacta    9360
agagcaagat tctgttccaa ttttatgagt ttttgggact ccaaagggaa caaaagtgtc    9420
```

```
tcatattgtg cttataacta cagttgtttt tataccagtg tagttttatt ccaggacagt      9480
tgatacttgg tactgtgctg taaattattt atccgacata gaacagcatg aacatatcaa      9540
gctctctttg tgcaggatat gtatgatttc atggctctgg ataggcttca actcttcgca      9600
ttgatcgtgg catagcatta cataaaatga tcaggcttgt caccatgggt ttaggtggtg      9660
aaggctatct taacttcatg ggaaatgagt ttgggcatcc tggtcagtct ttacaacatt      9720
attgcattct gcatgattgt gatttactgt aatttgaacc atgcttttct ttcacattgt      9780
atgtattatg taatctgttg cttccaagga ggaagttaac ttctatttac ttggcagaat      9840
ggatagattt tccaagaggc ccacaaactc ttccaaccgg caaagttctc ccctggaaat      9900
aacaatagtt atgataaatg ccgccgtaga tttgatcttg taagttttag ctgtgctatt      9960
acattccctc actagatctt tattggccat ttatttcttg atgaaatcat aatgtttgtt     10020
aggaaagatc aacattgctt ttgtagtttt gtagacgtta acataagtat gtgttgagag     10080
ttgttgatca ttaaaaatat catgattttt tgcaggaga tgcagatttt cttagatatc      10140
gtggtatgca agagttcgat caggcaatgc agcatcttga ggaaaaatat ggggtatgtc     10200
actggtttgt ctttgttgca taacaagtca cagtttaacg tcagtctctt caagtggtaa     10260
aaaaagtgta gaattaattc ctgtaatgag atgaaaactg tgcaaaggcg gagctggaat     10320
tgcttttcac caaaactatt ttcttaagtg cttgtgtatt gatacatata ccagcactga     10380
caatgtaact gcagtttatg acatctgagc accagtatgt ttcacggaaa catgaggaag     10440
ataaggtgat catcctcnaa aagaggagat ttggtatttg ttttcaactt ccactggagc     10500
aatagctttt ttgactaccg tgttgggtgt tccaagcctg ggaagtacaa ggtatgcttg     10560
ccttttcatt gtccacccctt caccagtagg gttagtgggg gcttctacaa cttttaattc     10620
cacatggata gagtttgttg gtcgtgcagc tatcaatata aagaataggg taatttgtaa     10680
agaaaagaat ttgctcgagc tgttgtagcc ataggaaggt tgttcttaac agccccgaag     10740
cacataccat tcattcatat tatctactta agtgtttgtt tcaatcttta tgctcagttg     10800
gactcggtct aatactagaa ctattttccg aatctaccct aaccatccta gcagttttag     10860
agcagcccca tttggacaat tggctgggtt tttgttagtt gtgacagttt ctgctatttc     10920
ttaatcaggt ggccttggac tctgacgatg cactctttgg tggattcagc aggcttgatc     10980
atgatgtcga ctacttcaca accgtaagtc tgggctcaag cgtcacttga ctcgtcttga     11040
ctcaactgct tacaaatctg atcaacttc ccaattgctg atgcccttgc aggaacatcc     11100
gcatgacaac aggccgcgct ctttctcggt gtacactccg agcagaactg cggtcgtgta     11160
tgcccttaca gagtaagaac cagcagcggc ttgttacaag gcaaagagag aactccagag     11220
agctcgtgga tcgtgagcga agcgacgggc aacggcgcga ggctgctcca agcgccatga     11280
ctgggagggg atcgtgcctc ttccccagat gccaggagga gcagatggat aggtagcttg     11340
ttggtgagcg ctcgaaagaa aatggacggg cctgggtgtt tgttgtgctg cactgaaccc     11400
tcctcctatc ttgcacattc ccggttgttt ttgtacatat aactaataat tgcccgtgcg     11460
ctcaacgtga aaatcc                                                    11476
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcacttacc gagaatggg                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgcatttgg atttcaattg                                                 20

<210> SEQ ID NO 5
<211> LENGTH: 3962
<212> TYPE: DNA
<213> ORGANISM: Aegilops tauschii

<400> SEQUENCE: 5
ggatccgatc cggctgcggc ggcggcgacg ggatggctgc gccggcattc gcagtttccg      60
cggcggggct ggcccggccg tcggctcctc gatccggcgg ggcagagcgg aggggcgcg      120 gggtggagct gcagtcgcca tcgctgctct tcggccgcaa caagggcacc cgttcacccc     180
gtaattattt gcgccacctt tctcactcac attctctcgt gtattctgtc gtgctcgccc     240
ttcgccgacg acgcgtgccg attccgtatc gggctgcggt gttcagcgat cttacgtcgg     300
ttccctcctg gtgtggtgat gtctgtaggt gccgtcggcg tcggaggttc tggatggcgc     360
gtggtcatgc gcgcgggggg gccgtccggg gaggtgatga tccctgacgg cggtagtggc     420
ggaacaccgc cttccatcga cggtcccgtt cagttcgatt ctgatgatct gaaggtagtt     480
ttttttttgc atcgatctga aggtacttga catatactac tgtattaccc tgagtaaata     540
ctgccaccat attttttatgg ttcgcttgaa ataccctgttt acttgctacg gttttcactt    600
tcattgagac gtcggacgaa attcactgaa ttcctataat ttggtagaca ccgaaatata     660
tactactcct tccgtcccat aatataagag cgttttttggc accttatatt ataggggcgga   720 gggagtacct tttaggtcaa aatattgtgg tagtttcaat tgtatacaag aattcaaata    780
ttttttttaa aaaaaaatca actaattggt tgagtttcaa gtgaagcgtt ttggtccttt    840
ggctgagatg taaaccgaaa tcactgaaat tcatagtagc cgaaacttta atagaactga    900
aactcaaaat ctgctatccg gcgaaattct aaagatttgc ttatttcaca cgtaggttgc    960
agtacaccct ctttctaatt tattggggaa ggggtattat tatcttgtta gtacctgcct   1020
gcatgacaat tgaaatctaa gacaaaacac catatgcgag gcctacacac ggtaggttgg   1080
tttacaacta tgtgtgccac agttcgtctg aacttttgt ccttcacatc gtgttaggtt    1140
ccattcattg atgatgaaac aagcctacag gatggaggtg aagatagtat ttggtcttca    1200
gagacaaatc aggttagtga agaaattgat gctgaagaca cgagcagaat ggacaaagaa    1260
tcatctacga gggagaaatt acgcattctg ccaccaccgg gaaatggaca gcaaatatac    1320
gagattgacc caacgctccg agactttaag taccatcttg agtatcggta tgcttcgctt    1380
ctattgtgtg cactttaaaa acaatttaca gtctttgata agatgtgaat ggctgccttgc    1440 tgtgacacga aactcttgaa gttcgtagtc actcttgtgt gttcatggtt ctgaggtaac    1500
atggtaaccg aacaaaaata ggaaagtggc aagcactgca atgtgagcta ctgataacca    1560
cccattgtaa ttgggtacac tgattaatat atatgtcttc atgggctcta ttttttttca    1620

-continued

```
atatctatgc caattgaaca acaatgcttt gtggacgggt gttcttttac cctcttcttc    1680
tatcaataga tgatatgcat actcatgcgt atcctacaaa aaattgaaca acaatgccac    1740
tttcccccgt gttgcttttg taaggatgaa acacatatgt ccagatcaaa ctatactagc    1800
agtctaactg tgccttaatg gatcaaaaac agatatagcc tatacaggag aatacgttca    1860
gacattgatg aacacgaagg aggcatggat gtattttccc gcggttacga gaagtttgga    1920
tttatgcgca ggtgaaattt cttgactaaa taactatgta tctacctttt ctttgtactc    1980
tatcaacatt cctcttccca tgcagcgctg aaggtatcac ttaccgagaa tgggctcctg    2040
gagcagatgt acgttcttct aaccatctga tcgtttacct gactatacta attctatctt    2100
tcaactaatt gtgaataatt actgctcatc agctatccta aggttgggga ttttgcacct    2160
cccagatgaa cagcatatta gtcgcacaa ctagcattat taagaactaa ctcctgcttc    2220
caattgcagt ctgcagcatt agttggcgac ttcaacaatt gggatccaaa tgcagaccat    2280
atgagcaaag tatgcatgta gtttcacaaa tatatcatat tttctttgta gattttttt    2340
tttagatcgg cttatctatt taaatgtggt tgaatataca ccttatatgt acgttgagct    2400
gtaaatatag ttggaagtgt ttaggagtat taaattcact ggactctatt ctttcacttg    2460
cctgttgcac gagcccatta ctagatatca atgttgatga tgcttttgtt gtatgaggtc    2520
gaagtgaaac atgcatgtta ccctttata taagtaaggt tgcacatgta ttttttatga    2580
tctaaacatt atttactgat tttgttcttg caagacacta agcagttta cataataatg    2640
gcgttggagc aggccgactg cacatctgaa ctgtagctcc atgtggttga tatagattac    2700
aaatgctcat attcaatgta actgttttca gaatgacctt ggtgtttggg agattttct    2760
gccaaacaat gcagatggtt cgccaccaat tcctcacggc tcacgggtga aggttgtttt    2820
cttctccttg ccaacggtgt taggctcagg aacatgtcct gtattactca gaagctcttt    2880
tgaacatcta ggtgagaatg gatactccat ctgggataaa ggattcaatt cctgcttgga    2940
tcaagtactc cgtgcagact ccaggagata taccatacaa tggaatatat tatgatcctc    3000
ccgaagaggt attttacttc atcttctgtg cttttagatt tcagatattt ttattagaag    3060
aaaattatga ttttttccct cacgaacctt cccaattgct atttcaagct gtcctactta    3120
tttgctgctg gcatcttatt tttctattct ctaaccagtt atgaaattcc ttacatgcat    3180
atgcaggaga agtatgtatt caagcatcct caacctaaac gaccaaaatc attgcggata    3240
tatgaaacac atgttggcat gagtagcccg gtatttcatc tttaccatgt attccataaa    3300
tgaagttagc tatatgcagt tcaaatttat ttacaggttg ttacaatggt attttgtgt    3360
tggtgcccct ctttcgtttt ataagtaaaa aacttatcat aaatttattt gttatgccgc    3420
ttggttaata caatctgaaa aatgtaactg tggacaatct agaactagat aatacaaatc    3480
tgaaaaaaca tgctggaata gtgtcatttc agtcaactag gatgttttga atgctcaaga    3540
gaagtactag tgtgtagcat caaaagctgg tgtccatttg ttcaaatgtt taattaacac    3600
tatagtgaaa acaagtaatt gcacaaagaa acaagtaatt gcccaagttc atatgttttt    3660
tcactatatt acatgtttca tcaacaattt aattaacctc attccttaca aacatttgta    3720
tttacatttg ttcctacata tatagttatt ttatatatca actttataaa tcatgactgt    3780
tataattaaa accgatggta tatcaacgat tgagataatt tggcatatgt ggatgaattt    3840
tgtggcttgt tatgctcttg ttttaataac ataataaata gattatgctt gttggtagcc    3900
tttttacatt aacacatggg caattacttg tttctttgtg caaccaggaa ccaaagatcg    3960
ag                                                                   3962
```

<210> SEQ ID NO 6
<211> LENGTH: 2968
<212> TYPE: DNA
<213> ORGANISM: Triticum sp.
<220> FEATURE:
<221> NAME/KEY: modified_base
<222> LOCATION: (35)..(35)
<223> OTHER INFORMATION: a, c, g or t
<220> FEATURE:
<221> NAME/KEY: modified_base
<222> LOCATION: (2937)..(2937)
<223> OTHER INFORMATION: a, c, g or t
<220> FEATURE:
<221> NAME/KEY: modified_base
<222> LOCATION: (2958)..(2958)
<223> OTHER INFORMATION: a, c, g or t
<220> FEATURE:
<221> NAME/KEY: modified_base
<222> LOCATION: (2965)..(2965)
<223> OTHER INFORMATION: a, c, g or t
<220> FEATURE:
<221> NAME/KEY: modified_base
<222> LOCATION: (2967)..(2968)
<223> OTHER INFORMATION: a, c, g or t

<400> SEQUENCE: 6

```
atggtcgacc tgcaggcggc cgcgaatgca ctagngattt tgacaccaga ccaactggta      60
atggtagcga ccggcgctca gctggaattc gcggccgcgt cgaccgtggg tttaagcagg     120
agacgaggcg gggtcagttg gcagttagg  ttggatccga tccggctgcg gcggcggcga     180
cgggatggct gcgccggcat cgcagtttc  gcggcgggg  ctggcccggc cgtcggctcc     240
tcgatccggc ggggcagagc ggaggggcg  cggggtggag ctgcagtcgc catcgctgct     300
cttcggccgc aacaagggca cccgttcacc ccgtgccgtc ggcgtcggag gttctggatg     360
gcgcgtggtc atgcgcgcgg gggggccgtc cggggaggtg atgatccctg acggcggtag     420
tggcggaaca ccgccttcca tcgacggtcc cgttcagttc gattctgatg atctgaaggt     480
tccattcatt gatgatgaaa caagcctaca ggatggaggt gaagatagta tttggtcttc     540
agagacaaat caggttagtg aagaaattga tgctgaagac acgagcagaa tggacaaaga     600
atcatctacg agggagaaat tacgcattct gccaccaccg ggaaatggac agcaaatata     660
cgagattgac ccaacgctcc gagactttaa gtaccatctt gagtatcgat atagcctata     720
caggagaata cgttcagaca ttgatgaaca cgaaggaggc atggatgtat tttcccgcgg     780
ttacgagaag tttggatta  tgcgcagcgc tgaaggtatc acttaccgag aatgggctcc     840
tggagcagat tctgcagcat tagttggcga cttcaacaat tgggatccaa atgcagacca     900
tatgagcaaa aatgaccttg gtgtttggga attttttctg ccaaacaatg cagatggttc     960
gccaccaatt cctcacggct cacgggtgaa ggtgcgaatg ggtactccat ctgggacaaa    1020
ggattcaatt cctgcttgga tcaagtactc cgtgcagact ccaggagata taccatacaa    1080
tggaatatat tatgatcctc ccgaagagga gaagtatgta ttcaagcatc ctcaacctaa    1140
acgaccaaaa tcattgcgga tatatgaaac acatgttggc atgagtagcc cggaaccaaa    1200
gatcaacaca tatgcaaact tcagggatga ggtgcttcca agaattaaaa gacttggata    1260
caatgcagtg caaataatgg caatccaaga gcactcatac tatggaagct ttgggtacca    1320
tgttaccaat ttctttgcac caagtagccg ttttgggtcc ccagaagatt taaaatcttt    1380
gattgataga gctcacgagc ttggcttggt tgtcctcatg gatgttgttc acagtcacgc    1440
gtcaaataat accttggacg ggttgaatgg ttttgatggc acgatacac  attacttcca    1500
```

```
tggcggttca cggggccatc actggatgtg ggattcccgt gtgtttaact atgggaataa    1560
ggaagttata aggtttctac tttccaatgc aagatggtgg ctagaggagt ataagtttga    1620
tggtttccga ttcgatggcg cgacctccat gatgtatacc catcatggat tacaagtaac    1680
ctttacagga agctaccatg aatattttgg ctttgccact gatgtagatg cggtcgttta    1740
cttgatgctg atgaatgatc taattcatgg gttttatcct gaagccgtaa ctatcggtga    1800
agatgttagt ggaatgccta catttgccct tcctgttcaa gttggtgggg ttggttttga    1860
ctatcgctta catatggctg ttgcccgcaa atggattgaa cttctcaaag gaaacgatga    1920
agcttgggag atgggtaata ttgtgcacac actaacaaac agaaggtggc tggaaaagtg    1980
tgttacttat gctgaaagtc acgatcaagc acttgttgga dacaagacta ttgcattctg    2040
gttgatggac aaggatatgt atgatttcat ggcgctgaac ggaccttcga cgcctaatat    2100
tgatcgtgga atagcactgc ataaaatgat tagacttatc acaatgggtc taggaggaga    2160
gggttatctt aactttatgg gaaatgagtt cgggcatcct gaatggatag actttccaag    2220
aggcccacaa gtacttccaa gtggtaagtt catcccagga acaacaaca gttacgacaa    2280 atgccgtcga agatttgacc tgggtgatgc agaatttctt aggtatcatg gtatgcagca    2340
gtttgatcag gcaatgcagc atcttgagga aaaatatggt tttatgacat cagaccacca    2400
gtacgtatct cggaaacatg aggaagataa ggtgatcgtg tttgaaaaag gggacttggt    2460
atttgtgttc aacttccact ggagtagtag ctatttcgac taccgggtcg gctgtttaaa    2520
gcctgggaag tacaaggtgg tcttagactc ggacgctgga ctctttggtg gatttggtag    2580
gatccatcac actgcagagc acttcacttc tgactgccaa catgacaaca ggccccattc    2640
attctcagtg tacactccta gcagaacctg tgttgtctat gctccaatga actaacagca    2700
aagtgcagca tacgcgtgcg cgctgttgtt gctagtagca agaaaaatcg tatggtcaat    2760
acaaccaggt gcaaggttta ataaggattt ttgcttcaac gagtcctgga tagacaagac    2820
aacatgatgt tgtgctgtgt gctcccaatc cccagggcgt tgtgaagaaa acatgctcat    2880
ctgtgttatt ttatggatca gcgacgaaac ctcccccaaa tacccctttt ttttttnaaa    2940
ggaggatagg ccccggnct ttgcntnn                                       2968
```

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ser Pro Gly Lys Val Leu Val Pro Asp Glu Ser Asp Asp Leu
1               5                   10                  15

Gly Cys

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Gly Pro Ser Gly Glu Val Met Ile Gly Cys
1               5                   10

```
<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Thr Pro Pro Ser Ile Asp Gly Pro Val Gln Asp Ser Asp Gly
1               5                   10                  15

Cys

<210> SEQ ID NO 10
<211> LENGTH: 8381
<212> TYPE: DNA
<213> ORGANISM: Triticum sp.
<220> FEATURE:
<221> NAME/KEY: modified_base
<222> LOCATION: (4636)..(4636)
<223> OTHER INFORMATION: a, c, g or t
<220> FEATURE:
<221> NAME/KEY: modified_base
<222> LOCATION: (4663)..(4663)
<223> OTHER INFORMATION: a, c, g or t
<220> FEATURE:
<221> NAME/KEY: modified_base
<222> LOCATION: (4696)..(4696)
<223> OTHER INFORMATION: a, c, g or t
<220> FEATURE:
<221> NAME/KEY: modified_base
<222> LOCATION: (4708)..(4708)
<223> OTHER INFORMATION: a, c, g or t
<220> FEATURE:
<221> NAME/KEY: modified_base
<222> LOCATION: (4724)..(4724)
<223> OTHER INFORMATION: a, c, g or t
<220> FEATURE:
<221> NAME/KEY: modified_base
<222> LOCATION: (4741)..(4741)
<223> OTHER INFORMATION: a, c, g or t
<220> FEATURE:
<221> NAME/KEY: modified_base
<222> LOCATION: (5488)..(5488)
<223> OTHER INFORMATION: a, c, g or t
<220> FEATURE:
<221> NAME/KEY: modified_base
<222> LOCATION: (5718)..(5718)
<223> OTHER INFORMATION: a, c, g or t
<220> FEATURE:
<221> NAME/KEY: modified_base
<222> LOCATION: (5726)..(5726)
<223> OTHER INFORMATION: a, c, g or t
<220> FEATURE:
<221> NAME/KEY: modified_base
<222> LOCATION: (5745)..(5745)
<223> OTHER INFORMATION: a, c, g or t
<220> FEATURE:
<221> NAME/KEY: modified_base
<222> LOCATION: (5798)..(5798)
<223> OTHER INFORMATION: a, c, g or t
<220> FEATURE:
<221> NAME/KEY: modified_base
<222> LOCATION: (5868)..(5868)
<223> OTHER INFORMATION: a, c, g or t
<220> FEATURE:
<221> NAME/KEY: modified_base
<222> LOCATION: (5909)..(5909)
<223> OTHER INFORMATION: a, c, g or t
<220> FEATURE:
<221> NAME/KEY: modified_base
<222> LOCATION: (5925)..(5925)
<223> OTHER INFORMATION: a, c, g or t
<220> FEATURE:
```

```
<221> NAME/KEY: modified_base
<222> LOCATION: (5967)..(5967)
<223> OTHER INFORMATION: a, c, g or t
<220> FEATURE:
<221> NAME/KEY: modified_base
<222> LOCATION: (5986)..(5986)
<223> OTHER INFORMATION: a, c, g or t
<220> FEATURE:
<221> NAME/KEY: modified_base
<222> LOCATION: (5999)..(5999)
<223> OTHER INFORMATION: a, c, g or t
<220> FEATURE:
<221> NAME/KEY: modified_base
<222> LOCATION: (6085)..(6085)
<223> OTHER INFORMATION: a, c, g or t
<220> FEATURE:
<221> NAME/KEY: modified_base
<222> LOCATION: (6177)..(6177)
<223> OTHER INFORMATION: a, c, g or t
<220> FEATURE:
<221> NAME/KEY: modified_base
<222> LOCATION: (6245)..(6245)
<223> OTHER INFORMATION: a, c, g or t
<220> FEATURE:
<221> NAME/KEY: modified_base
<222> LOCATION: (8004)..(8004)
<223> OTHER INFORMATION: a, c, g or t
<220> FEATURE:
<221> NAME/KEY: modified_base
<222> LOCATION: (8182)..(8182)
<223> OTHER INFORMATION: a, c, g or t

<400> SEQUENCE: 10
aagctttgta gccttgcacg ggctccccaa caaactgcct cactcgattg tcaaaaaagt      60
aaaaatgatt gtagaaaaaa aaactgactc actcgtcact accctaccgt cctacatgac     120
acctggccgc aagacgacgc cgtcctcctg ccgcgcgcgt ccgcgatcac accaccgcaa     180
aaaccaaaac ctcttcgccg gtgcgtccca cgctaccatc catgcagccg tccgcccgcg     240
cgcgcgttgc ccgcaccacc cgctggcggc caccacgccg ccactctcgc gtgaaggctc     300
cgtccgcttc ctcctagttc cactctctct ccgtgctagc agtatatagc atccgccctc     360
cgcccccctcc caatcttaga acaccectcc ctttgcctcc tcatttcgct cgcgtgggtt    420
taagcaggag acgaggcggg gtcagttggg cagttaggtt ggatccgatc cggctgcggc     480
ggcggcgacg ggatggctgc gccggcattc gcagtttccg cggcggggct ggcccggccg     540
tcggctcctc gatccggcgg ggcagagcgg aggggcgcg gggtggagct gcagtcgcca      600
tcgctgctct tcggccgcaa caagggcacc cgttcacccc gtaattattt gcgccacctt     660
tctcactcac attctctcgt gtattctgtc gtgctcgccc ttcgccgacg acgcgtgccg     720
attccgtatc gggctgcggt gttcagcgat cttacgtcgg ttccctcctg gtgtggtgat     780
gtctgtaggt gccgtcggcg tcggaggttc tggatggcgc gtggtcatgc gcgcgggggg     840
gccgtccggg gaggtgatga tccctgacgg cggtagtggc ggaacaccgc cttccatcga     900
cggtcccgtt cagttcgatt ctgatgatct gaaggtagtt ttttttttgc atcgatctga     960
aggtacttga catatactac tgtattaccc tgagtaaata ctgccaccat atttttatgg    1020
ttcgcttgaa atacctgttt acttgctacg gttttcactt tcattgagac gtcggacgaa    1080
attcactgaa ttcctataat ttggtagaca ccgaaatata tactactcct tccgtcccat    1140
aatataagag cgttttttggc acctatatt atagggcgga gggagtacct tttaggtcaa    1200
aatattgtgg tagtttcaat tgtatacaag aattcaaata tttttttttaa aaaaaaatca   1260
actaattggt tgagtttcaa gtgaagcgtt ttggtccttt ggctgagatg taaaccgaaa    1320
tcactgaaat tcatagtagc cgaaacttta atagaactga aactcaaaat ctgctatccg    1380
```

```
gcgaaattct aaagatttgc ttatttcaca cgtaggttgc agtacaccct ctttctaatt   1440
tattggggaa ggggtattat tatcttgtta gtacctgcct gcatgacaat tgaaatctaa   1500
gacaaaacac catatgcgag gcctacacac ggtaggttgg tttacaacta tgtgtgccac   1560
agttcgtctg aactttttgt ccttcacatc gtgttaggtt ccattcattg atgatgaaac   1620
aagcctacag gatggaggtg aagatagtat ttggtcttca gagacaaatc aggttagtga   1680
agaaattgat gctgaagaca cgagcagaat ggacaaagaa tcatctacga gggagaaatt   1740
acgcattctg ccaccaccgg gaaatggaca gcaaatatac gagattgacc caacgctccg   1800
agactttaag taccatcttg agtatcggta tgcttcgctt ctattgtgtg cacttttaaaa  1860
acaatttaca gtctttgata agatgtgaat ggctgcttgc tgtgacacga aactcttgaa   1920
gttcgtagtc actcttgtgt gttcatggtt ctgaggtaac atggtaaccg aacaaaaata   1980
ggaaagtggc aagcactgca atgtgagcta ctgataacca cccattgtaa ttgggtacac   2040
tgattaatat atatgtcttc atgggctcta tttttttttca atatctatgc caattgaaca   2100
acaatgcttt gtggacgggt gttcttttac cctcttcttc tatcaataga tgatatgcat   2160
actcatgcgt atcctacaaa aaattgaaca acaatgccac tttcccccgt gttgcttttg   2220
taaggatgaa acacatatgt ccagatcaaa ctatactagc agtctaactg tgccttaatg   2280
gatcaaaaac agatatagcc tatacaggag aatacgttca gacattgatg aacacgaagg   2340
aggcatggat gtattttccc gcggttacga gaagtttgga tttatgcgca ggtgaaattt   2400
cttgactaaa taactatgta tctacctttt cttttgtactc tatcaacatt cctcttccca   2460
tgcagcgctg aaggtatcac ttaccgagaa tgggctcctg gagcagatgt acgttcttct   2520
aaccatctga tcgtttacct gactatacta attctatctt tcaactaatt gtgaataatt   2580
actgctcatc agctatccta aggttgggga ttttgcacct cccagatgaa cagcatatta   2640
agtcgcacaa ctagcattat taagaactaa ctcctgcttc caattgcagt ctgcagcatt   2700
agttggcgac ttcaacaatt gggatccaaa tgcagaccat atgagcaaag tatgcatgta   2760
gtttcacaaa tatatcatat tttcttttgta gattttttttt tttagatcgg cttatctatt   2820
taaatgtggt tgaatataca ccttatatgt acgttgagct gtaaatatag ttggaagtgt   2880
ttaggagtat taaattcact ggactctatt ctttcacttg cctgttgcac gagcccatta   2940
ctagatatca atgttgatga tgcttttgtt gtatgaggtc gaagtgaaac atgcatgtta   3000
cccttttata taagtaaggt tgcacatgta ttttttatga tctaaacatt atttactgat   3060
tttgttcttg caagacacta agcagtttta cataataatg gcgttggagc aggccgactg   3120
cacatctgaa ctgtagctcc atgtggttga tatagattac aaatgctcat attcaatgta   3180
actgttttca gaatgacctt ggtgtttggg agattttttct gccaaacaat gcagatggtt   3240
cgccaccaat tcctcacggc tcacgggtga aggttgtttt cttctccttg ccaacggtgt   3300
taggctcagg aacatgtcct gtattactca gaagctcttt tgaacatcta ggtgagaatg   3360
gatactccat ctgggataaa ggattcaatt cctgcttgga tcaagtactc cgtgcagact   3420
ccaggagata taccatacaa tggaatatat tatgatcctc ccgaagaggt attttacttc   3480
atcttctgtg ctttagatt tcagatattt ttattagaag aaaattatga ttttttccct   3540
cacgaacctt cccaattgct atttcaagct gtcctactta tttgctgctg gcatcttatt   3600
tttctattct ctaaccagtt atgaaattcc ttacatgcat atgcaggaga agtatgtatt   3660
caagcatcct caacctaaac gaccaaaatc attgcggata tatgaaacac atgttggcat   3720
```

```
gagtagcccg gtatttcatc tttaccatgt attccataaa tgaagttagc tatatgcagt    3780
tcaaatttat ttacaggttg ttacaatggt attttgtgt tggtgccctt ctttcgtttt      3840
ataagtaaaa aacttatcat aaatttattt gttatgccgc ttggttaata caatctgaaa    3900
aatgtaactg tggacaatct agaactagat aatacaaatc tgaaaaaaca tgctggaata    3960
gtgtcatttc agtcaactag gatgttttga atgctcaaga gaagtactag tgtgtagcat    4020
caaaagctgg tgtccatttg ttcaaatgtt taattaacac tatagtgaaa caagtaatt     4080 gcacaaagaa acaagtaatt gcccaagttc atatgttttt tcactatatt acatgtttca    4140
tcaacaattt aattaacctc attccttaca aacatttgta tttacatttg ttcctacata    4200
tatagttatt ttatatatca actttataaa tcatgactgt tataattaaa accgatggta    4260
tatcaacgat tgagataatt tggcatatgt ggatgaattt tgtggcttgt tatgctcttg    4320
ttttaataac ataataaata gattatgctt gttggtagcc ttttttacatt aacacatggg    4380 caattacttg tttctttgtg caaccaggaa ccaaagatcg acacatatgc aaacttcagg    4440
gatgaggtgc ttccaagaat taaaagactt ggatacaatg cagtgcaaat aatggcaatc    4500
caagagcact catactatgg aagctttggg tagttctctg ggtcgatttc tggttctttt    4560
agttatcttt tgtccataga acatatttca actttagcaa ctatactatt atattaactt    4620
ttcagctatt gtcttncttt ttcttatgtg agagactgct gcntcttgct acttcctgtg    4680
ttctcattca gagtanacat cttatganta gacaactcta tgtngacatt ccggaagtat    4740
ncactggctg attcggtcta aaataacata ctgctcagat agccacataa cagtacgatt    4800
acacacataa tgaccatgtt tgcatagagt ggcggtagta tgttcctcac catactagca    4860
taatgacttg ttatataaga gtatatcata ttaacttctt ttccaatgac atggaagctg    4920
taacaacttt caaatcattt ttgtctttta agtgctgctt ttttcctgtt tgacaattaa    4980
tacaatacca cttttatgtg tttttacttc tattgcaggt accatgttac caatttcttt    5040
gcaccaagta gccgttttgg gtccccagaa gatttaaaat ctttgattga tagagctcac    5100
gagcttggct tggttgtcct catggatgtt gttcacaggt acttaatgta atttgaggtt    5160
ggcgtgttaa gttcacatta atcttaattc tttatttcaa ttcctatggc ctctctccta    5220
gattggaaca gtaaaagcat catccagttt gtataaattg ctaaaagaac attttacatg    5280
ttaagtattt tcaattacta tgaaacatat aaatttacat acttattgat tttacgacag    5340
aagtaccgat ctcacaagat gaacaattgg ttgatcacat atcatttcat actacaatac    5400
aagaaaatga atagagaacg agttaatatt agccttggta aaatcagcaa cttgtttgga    5460
aataaagtat agtgatgcca gtgcaaanaa caaggcatca agttggtttc agctcccacg    5520
gtcggtgcta gctgtcaagg gtaatttgca cgtagtcgca catagatttg tgtgggagtg    5580
gaaagtaacc acagattgtc cgaggaacac gggacacacg tcttagccac aggtttgggc    5640
tccccttgat gcgggtagta gctttactcc ttatatgaaa ttatctcaag atagatttca    5700 atttgggggtt acacttanga actcancaag ttaaggatca actcnctgag ttctatacga    5760
ctgatctttg accagagatat cttgatcagg ctaagtanca aaatccaggc cttgagatgt    5820
tgaacatgtc cttcattttg ggctgggtgc ccttgggcat aaggtgtngt ccttccttca    5880
tgtgcttctt gcagcgtatg acataaaacnt cctctgagtt ggtanatgca cggttccctt    5940
tgaggaaatc aggggtagtc gcatctnggg aaagttggtc acccangcat ggatcctcng    6000
cgcacaccgg gcaaacacgg tgaaaccact tctcctcgac actagctaac ttgacattca    6060
agcaaactaa gaatataact ttatntctaa atgaaccgga caccctcctt gtgcctgcac    6120
```

```
ctacagagta caatgccagt tttggactga actcttgtgt tcatgtatgt gctaatnaca      6180
taggttctaa ccatgattct aaatagcgcg ttataactcc actatagtaa tgctatagcg      6240
tttanaagat cccgcactaa gggaccttag tccaaataca tgatcaaaca ttttacatag      6300
cgcgctatag ctatttaaaa ctatggtcac ccgctaagag gcataactcg ctatttaaaa      6360
ctatggttct aacttttaat ctattttatg tcttggtcca aagccccttt ttgttctata      6420
gctttacctt tgggttgaga tcacccttaa cccattggta atcctggttg atttactcca      6480
tcctttcttg cgtagcttta cttttggttt tttgtttctc acagtcacgc gtcaaataat      6540
accttggacg ggttgaatgg ttttgatggc acggatacac attacttcca tggcggttca      6600
cggggccatc actggatgtg ggattcccgt gtgtttaact atgggaataa ggaagtatgg      6660
gactatagaa tttctattgc catttgttat gtatttatcc attaattaat cctccaaccg      6720
atattccaac attgttatct ttatacaggt tataaggttt ctactttcca atgcaagatg      6780
gtggctagag gagtataagt ttgatggttt ccgattcgat ggcgcgacct ccatgatgta      6840
tacccatcat ggattacaag taattcattg cttgattgtc tttgttctat cttgactacc      6900
tgtgcaactt taataagatt acgcctagct aatatttct tttatgttat agtatcaatt       6960
tttatttgag cttgaaacct aaattacttt ttttttgaat tgctgcgctc tattttaggt      7020
aacctttaca ggaagctacc atgaatattt tggctttgcc actgatgtag atgcggtcgt      7080
ttacttgatg ctgatgaatg atctaattca tgggttttat cctgaagccg taactatcgg      7140
tgaagatgta agtgtttcta tagtcatctt tcaaatatgaa tttgttagaa ctattggtac      7200
ttatcttttt tgtagtttag gctattctgt tcattcttac aggaggtgca tacagaagtt      7260
gctttagatt ttgaaacgca gtgcacattg tgccattact ttgtagctat atcgagttga      7320
gacttgagag ccatggtaat caagttcctg acgtggcatt gcattagata gttgcatgtc      7380
taagttcctg acgtggagat agaagaaaga acgcaccccc cgcgtcgctc ctctcagggc      7440
gacacgggcg gagccctcac ccccgccgcc acagggagca tccacccttc tcctctcccc      7500
tcgccgccgc cggagggcaa agaccgcgcg cgtcgcggc ggtgggtgcg gcctgggctg       7560
gcatctggca gcggcgattt ggcctcccct gcccagaact gtgctgccgc ggtttgtggc      7620
agcttgggca tcggcagtgg cccgagtctg cggtggcggc gtgtctggcg tccggaggtg      7680
cagcgattgt gcggttgtgt ggctcaggct cggagggcgt gcgggctgcc aggtccggcc      7740
agatctggcc tcgagtggct tcgtacgggg cgtggctgt tgcgggtccg tgggccgagg       7800
ttcgggtgtg gctgctgctt gcccggaccg gtggtgcgta acgatgccgg agcagcgtcc      7860
tcgggtcgtt gaagtgggcg ctcctccggc agcttcaggt ggtgattcgt cgcagcgggt      7920
ggtgcactgg gggtctcggc tgattgtggt gccatggtgg tggtggttgt tggcggtagc      7980
aaagtgcctg gtgcacacgg ctanggtttt gcggatggac agacttgatg caatgccta       8040
gggcatagtg aatttcagct aagtacctag caccgacctt ggtcaatgcc accgccgctg      8100
gtgtcttagg acgttgttgc ccttgttgga ggcgtgttgt ggagcccctt cacctccatg      8160
ggcatttaga tctcgagctc tntgggtgaa aacgccggct ttggctttgg ccggagtggg      8220
cggtggcggc gtaaccgtcg ctccccccat gggggtgtag tcttggaggt ctagactcga      8280
ggaattcggt accccgggtt cgaaatcgat aagcttggat ccgaagagct cccaacgcgt      8340
tggatgcata gcttgagtat tctatagtgt cacctaaata g                         8381
```

<210> SEQ ID NO 11

<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgtcctaca tgacacctgg ccg                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgccggatc gaggagccga cgg                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcggcggcg acgggatggc tgc                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgccgtcagg gatcatcacc tcc                                              23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacccattgt aattgggtac actg                                             24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccatgcctc cttcgtgttc atca                                             24

<210> SEQ ID NO 17
<211> LENGTH: 24

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgcgcataa atccaaactt ctcg                                          24

<210> SEQ ID NO 18
<211> LENGTH: 226
<212> TYPE: DNA
<213> ORGANISM: Triticum sp.

<400> SEQUENCE: 18
atcacttacc gagaatgggc tcctggagcg catgtatgtc ttttaagtct taacagacac    60
cttccaattt attgttaatg gtcactattc accaactagc ttactggact tacaaattag   120
cttactgaat actgaccagt tactataaat ttatgatctg gcttttgcac cctgttacag   180
tctgcagcat tagtaggtga cttcaacaat tgggatccaa atgcag                  226

<210> SEQ ID NO 19
<211> LENGTH: 228
<212> TYPE: DNA
<213> ORGANISM: Triticum sp.

<400> SEQUENCE: 19
atcacttacc gagaatgggc tcctggagcg catgtacgtc ttttaagtct taacagacac    60
cttccaattc attgttaatg gtcacactat tcaccaacta gcttactgga cttacaactt   120
agcttactga atactgacca gttgctctaa atttatgatc tggcttttgc atcctgttac   180
agtctgcagc attagtaggt gacttcaaca attggaatcc aaatgcag                228

<210> SEQ ID NO 20
<211> LENGTH: 217
<212> TYPE: DNA
<213> ORGANISM: Triticum sp.

<400> SEQUENCE: 20
atcacttacc gagaatgggc tcctggagcg catgtacgtc ttaacagaca ccttctaatt    60
tattgttaat ggtcactatt caccaactag cttactggac ttacaaaata gcttactgaa   120
tactgaccag ttactctaaa tttatgatct ggcttttgga tcctgttaca gtctgcagca   180
ttagtaggtg acttcaacaa ttggaatcca aatgcag                            217

<210> SEQ ID NO 21
<211> LENGTH: 262
<212> TYPE: DNA
<213> ORGANISM: Triticum sp.
<220> FEATURE:
<221> NAME/KEY: modified_base
<222> LOCATION: (26)..(26)
<223> OTHER INFORMATION: a, c, g or t
<220> FEATURE:
<221> NAME/KEY: modified_base
<222> LOCATION: (32)..(32)
<223> OTHER INFORMATION: a, c, g or t
<220> FEATURE:
<221> NAME/KEY: modified_base
<222> LOCATION: (180)..(180)
<223> OTHER INFORMATION: a, c, g or t

<400> SEQUENCE: 21
atcacttacc gagaatgggc tcctgngagc anatgtatgt tcttctgact gtctgatcgt    60
```

```
ttacctgact atactaattc tatctttcaa ctgcttgtga ataattagtg ctcatctgct    120
atcctaaggt tggggatttt gcacttccca gatgaacagc atattaagtt gcacaactan    180
ctttatttaa gaactaactc ttgcttccaa ttgcagtctg caacattagt tggcgacttc    240
aacaattgga atccaaatgc ag                                             262

<210> SEQ ID NO 22
<211> LENGTH: 348
<212> TYPE: DNA
<213> ORGANISM: Hordeum vulgare

<400> SEQUENCE: 22
tcgcagcgct gaaggtatca cttaccgaga atgggctcct ggagcagatt ctgcagcatt     60
agttggcgac ttcaacaatt gggatccaac tgcagaccat atgagcaaaa atgacttggg    120
tatttgggag attttttctgc caaacaatgc agatggttcg ccgccaattc ctcatggctc    180
acgggtgaag gtgcggatgg atactccatc tgggacaaag gattcaattc ctgcttggat    240
caagtactcc gtgcagactc caggagatat accatacaat ggaatatatt atgaccctcc    300
tgaagaggag aagtatgtat tcaagcatcc tcaacctaaa cgaccaaa               348

<210> SEQ ID NO 23
<211> LENGTH: 823
<212> TYPE: PRT
<213> ORGANISM: Triticum sp.

<400> SEQUENCE: 23

Met Ala Thr Phe Ala Val Ser Gly Ala Thr Leu Gly Val Ala Arg Pro
1               5                   10                  15

Ala Gly Ala Gly Gly Leu Leu Pro Arg Ser Gly Ser Glu Arg Arg
            20                  25                  30

Gly Gly Val Asp Leu Pro Ser Leu Leu Leu Arg Lys Lys Asp Ser Ser
        35                  40                  45

Arg Ala Val Leu Ser Arg Ala Ala Ser Pro Gly Lys Val Leu Val Pro
    50                  55                  60

Asp Gly Glu Ser Asp Asp Leu Ala Ser Pro Ala Gln Pro Glu Glu Leu
65                  70                  75                  80

Gln Ile Pro Glu Asp Ile Glu Glu Gln Thr Ala Glu Val Asn Met Thr
                85                  90                  95

Gly Gly Thr Ala Glu Lys Leu Glu Ser Ser Glu Pro Thr Gln Gly Ile
            100                 105                 110

Val Glu Thr Ile Thr Asp Gly Val Thr Lys Gly Val Lys Glu Leu Val
        115                 120                 125

Val Gly Glu Lys Pro Arg Val Val Pro Lys Pro Gly Asp Gly Gln Lys
    130                 135                 140

Ile Tyr Glu Ile Asp Pro Thr Leu Lys Asp Phe Arg Ser His Leu Asp
145                 150                 155                 160

Tyr Arg Tyr Ser Glu Tyr Arg Arg Ile Arg Ala Ala Ile Asp Gln His
                165                 170                 175

Glu Gly Gly Leu Glu Ala Phe Ser Arg Gly Tyr Glu Lys Leu Gly Phe
            180                 185                 190

Thr Arg Ser Ala Glu Gly Ile Thr Tyr Arg Glu Trp Ala Pro Gly Ala
        195                 200                 205

His Ser Ala Ala Leu Val Gly Asp Phe Asn Asn Trp Asn Pro Asn Ala
    210                 215                 220
```

```
Asp Thr Met Thr Arg Asp Asp Tyr Gly Val Trp Glu Ile Phe Leu Pro
225                 230                 235                 240

Asn Asn Ala Asp Gly Ser Pro Ala Ile Pro His Gly Ser Arg Val Lys
            245                 250                 255

Ile Arg Met Asp Thr Pro Ser Gly Val Lys Asp Ser Ile Ser Ala Trp
            260                 265                 270

Ile Lys Phe Ser Val Gln Ala Pro Gly Glu Ile Pro Phe Asn Gly Ile
            275                 280                 285

Tyr Tyr Asp Pro Pro Glu Glu Glu Lys Tyr Val Phe Gln His Pro Gln
            290                 295                 300

Pro Lys Arg Pro Glu Ser Leu Arg Ile Tyr Glu Ser His Ile Gly Met
305                 310                 315                 320

Ser Ser Pro Glu Pro Lys Ile Asn Ser Tyr Ala Asn Phe Arg Asp Glu
            325                 330                 335

Val Leu Pro Arg Ile Lys Arg Leu Gly Tyr Asn Ala Val Gln Ile Met
            340                 345                 350

Ala Ile Gln Glu His Ser Tyr Tyr Ala Ser Phe Gly Tyr His Val Thr
            355                 360                 365

Asn Phe Phe Ala Pro Ser Ser Arg Phe Gly Thr Pro Glu Asp Leu Lys
            370                 375                 380

Ser Leu Ile Asp Arg Ala His Glu Leu Gly Leu Leu Val Leu Met Asp
385                 390                 395                 400

Ile Val His Ser His Ser Ser Asn Asn Thr Leu Asp Gly Leu Asn Gly
            405                 410                 415

Phe Asp Gly Thr Asp Thr His Tyr Phe His Gly Pro Arg Gly His
            420                 425                 430

His Trp Met Trp Asp Ser Arg Leu Phe Asn Tyr Gly Ser Trp Glu Val
            435                 440                 445

Leu Arg Phe Leu Leu Ser Asn Ala Arg Trp Trp Leu Glu Glu Tyr Lys
            450                 455                 460

Phe Asp Gly Phe Arg Phe Asp Gly Val Thr Ser Met Met Tyr Thr His
465                 470                 475                 480

His Gly Leu Gln Met Thr Phe Thr Gly Asn Tyr Gly Glu Tyr Phe Gly
            485                 490                 495

Phe Ala Thr Asp Val Asp Ala Val Val Tyr Leu Met Leu Val Asn Asp
            500                 505                 510

Leu Ile His Gly Leu His Pro Asp Ala Val Ser Ile Gly Glu Asp Val
            515                 520                 525

Ser Gly Met Pro Thr Phe Cys Ile Pro Val Pro Asp Gly Gly Val Gly
            530                 535                 540

Phe Asp Tyr Arg Leu His Met Ala Val Ala Asp Lys Trp Ile Glu Leu
545                 550                 555                 560

Leu Lys Gln Ser Asp Glu Ser Trp Lys Met Gly Asp Ile Val His Thr
            565                 570                 575

Leu Thr Asn Arg Arg Trp Leu Glu Lys Cys Val Thr Tyr Ala Glu Ser
            580                 585                 590

His Asp Gln Ala Leu Val Gly Asp Lys Thr Ile Ala Phe Trp Leu Met
            595                 600                 605

Asp Lys Asp Met Tyr Asp Phe Met Ala Leu Asp Arg Pro Ser Thr Pro
            610                 615                 620

Arg Ile Asp Arg Gly Ile Ala Leu His Lys Met Ile Arg Leu Val Thr
625                 630                 635                 640

Met Gly Leu Gly Gly Glu Gly Tyr Leu Asn Phe Met Gly Asn Glu Phe
```

-continued

```
                645                 650                 655
Gly His Pro Glu Trp Ile Asp Phe Pro Arg Gly Pro Gln Thr Leu Pro
            660                 665                 670

Thr Gly Lys Val Leu Pro Gly Asn Asn Asn Ser Tyr Asp Lys Cys Arg
        675                 680                 685

Arg Arg Phe Asp Leu Gly Asp Ala Asp Phe Leu Arg Tyr His Gly Met
    690                 695                 700

Gln Glu Phe Asp Gln Ala Met Gln His Leu Glu Lys Tyr Gly Phe
705                 710                 715                 720

Met Thr Ser Glu His Gln Tyr Val Ser Arg Lys His Glu Glu Asp Lys
            725                 730                 735

Val Ile Ile Phe Glu Arg Gly Asp Leu Val Phe Val Phe Asn Phe His
        740                 745                 750

Trp Ser Asn Ser Phe Phe Asp Tyr Arg Val Gly Cys Ser Arg Pro Gly
    755                 760                 765

Lys Tyr Lys Val Ala Leu Asp Ser Asp Ala Leu Phe Gly Gly Phe
770                 775                 780

Ser Arg Leu Asp His Asp Val Asp Tyr Phe Thr Thr Glu His Pro His
785                 790                 795                 800

Asp Asn Arg Pro Arg Ser Phe Ser Val Tyr Thr Pro Ser Arg Thr Ala
            805                 810                 815

Val Val Tyr Ala Leu Thr Glu
            820

<210> SEQ ID NO 24
<211> LENGTH: 768
<212> TYPE: PRT
<213> ORGANISM: Triticum sp.

<400> SEQUENCE: 24

Met Ala Thr Phe Ala Val Ser Gly Ala Thr Leu Gly Val Ala Arg Pro
1               5                   10                  15

Pro Ala Ala Ala Gln Pro Glu Glu Leu Gln Ile Pro Glu Asp Ile Glu
            20                  25                  30

Glu Gln Thr Ala Glu Val Asn Met Thr Gly Gly Thr Ala Glu Lys Leu
        35                  40                  45

Glu Ser Ser Glu Pro Thr Gln Gly Ile Val Glu Thr Ile Thr Asp Gly
    50                  55                  60

Val Thr Lys Gly Val Lys Glu Leu Val Val Gly Glu Lys Pro Arg Val
65                  70                  75                  80

Val Pro Lys Pro Gly Asp Gly Gln Lys Ile Tyr Glu Ile Asp Pro Thr
            85                  90                  95

Leu Lys Asp Phe Arg Ser His Leu Asp Tyr Arg Tyr Ser Glu Tyr Arg
        100                 105                 110

Arg Ile Arg Ala Ala Ile Asp Gln His Glu Gly Gly Leu Glu Ala Phe
    115                 120                 125

Ser Arg Gly Tyr Glu Lys Leu Gly Phe Thr Arg Ser Ala Glu Gly Ile
130                 135                 140

Thr Tyr Arg Glu Trp Ala Pro Gly Ala His Ser Ala Ala Leu Val Gly
145                 150                 155                 160

Asp Phe Asn Asn Trp Asn Pro Asn Ala Asp Thr Met Thr Arg Asp Asp
            165                 170                 175

Tyr Gly Val Trp Glu Ile Phe Leu Pro Asn Asn Ala Asp Gly Ser Pro
        180                 185                 190
```

-continued

```
Ala Ile Pro His Gly Ser Arg Val Lys Ile Arg Met Asp Thr Pro Ser
        195                 200                 205

Gly Val Lys Asp Ser Ile Ser Ala Trp Ile Lys Phe Ser Val Gln Ala
210                 215                 220

Pro Gly Glu Ile Pro Phe Asn Gly Ile Tyr Tyr Asp Pro Pro Glu Glu
225                 230                 235                 240

Glu Lys Tyr Val Phe Gln His Pro Gln Pro Lys Arg Pro Glu Ser Leu
                245                 250                 255

Arg Ile Tyr Glu Ser His Ile Gly Met Ser Ser Pro Glu Pro Lys Ile
            260                 265                 270

Asn Ser Tyr Ala Asn Phe Arg Asp Glu Val Leu Pro Arg Ile Lys Arg
        275                 280                 285

Leu Gly Tyr Asn Ala Val Gln Ile Met Ala Ile Gln Glu His Ser Tyr
    290                 295                 300

Tyr Ala Ser Phe Gly Tyr His Val Thr Asn Phe Phe Ala Pro Ser Ser
305                 310                 315                 320

Arg Phe Gly Thr Pro Glu Asp Leu Lys Ser Leu Ile Asp Arg Ala His
                325                 330                 335

Glu Leu Gly Leu Leu Val Leu Met Asp Ile Val His Ser His Ser Ser
            340                 345                 350

Asn Asn Thr Leu Asp Gly Leu Asn Gly Phe Asp Gly Thr Asp Thr His
        355                 360                 365

Tyr Phe His Gly Gly Pro Arg Gly His His Trp Met Trp Asp Ser Arg
    370                 375                 380

Leu Phe Asn Tyr Gly Ser Trp Glu Val Leu Arg Phe Leu Leu Ser Asn
385                 390                 395                 400

Ala Arg Trp Trp Leu Glu Glu Tyr Lys Phe Asp Gly Phe Arg Phe Asp
                405                 410                 415

Gly Val Thr Ser Met Met Tyr Thr His His Gly Leu Gln Met Thr Phe
            420                 425                 430

Thr Gly Asn Tyr Gly Glu Tyr Phe Gly Phe Ala Thr Asp Val Asp Ala
        435                 440                 445

Val Val Tyr Leu Met Leu Val Asn Asp Leu Ile His Gly Leu His Pro
    450                 455                 460

Asp Ala Val Ser Ile Gly Glu Asp Val Ser Gly Met Pro Thr Phe Cys
465                 470                 475                 480

Ile Pro Val Pro Asp Gly Gly Val Gly Phe Asp Tyr Arg Leu His Met
                485                 490                 495

Ala Val Ala Asp Lys Trp Ile Glu Leu Leu Lys Gln Ser Asp Glu Ser
            500                 505                 510

Trp Lys Met Gly Asp Ile Val His Thr Leu Thr Asn Arg Arg Trp Leu
        515                 520                 525

Glu Lys Cys Val Thr Tyr Ala Glu Ser His Asp Gln Ala Leu Val Gly
    530                 535                 540

Asp Lys Thr Ile Ala Phe Trp Leu Met Asp Lys Asp Met Tyr Asp Phe
545                 550                 555                 560

Met Ala Leu Asp Arg Pro Ser Thr Pro Arg Ile Asp Arg Gly Ile Ala
                565                 570                 575

Leu His Lys Met Ile Arg Leu Val Thr Met Gly Leu Gly Gly Glu Gly
            580                 585                 590

Tyr Leu Asn Phe Met Gly Asn Glu Phe Gly His Pro Glu Trp Ile Asp
        595                 600                 605

Phe Pro Arg Gly Pro Gln Thr Leu Pro Thr Gly Lys Val Leu Pro Gly
```

```
                    610                 615                 620

Asn Asn Asn Ser Tyr Asp Lys Cys Arg Arg Phe Asp Leu Gly Asp
625                 630                 635                 640

Ala Asp Phe Leu Arg Tyr His Gly Met Gln Glu Phe Asp Gln Ala Met
                    645                 650                 655

Gln His Leu Glu Glu Lys Tyr Gly Phe Met Thr Ser Glu His Gln Tyr
                    660                 665                 670

Val Ser Arg Lys His Glu Glu Asp Lys Val Ile Ile Phe Glu Arg Gly
                    675                 680                 685

Asp Leu Val Phe Val Phe Asn Phe His Trp Ser Asn Ser Phe Phe Asp
690                 695                 700

Tyr Arg Val Gly Cys Ser Arg Pro Gly Lys Tyr Lys Val Ala Leu Asp
705                 710                 715                 720

Ser Asp Asp Ala Leu Phe Gly Gly Phe Ser Arg Leu Asp His Asp Val
                    725                 730                 735

Asp Tyr Phe Thr Thr Glu His Pro His Asp Asn Arg Pro Arg Ser Phe
                    740                 745                 750

Ser Val Tyr Thr Pro Ser Arg Thr Ala Val Val Tyr Ala Leu Thr Glu
                    755                 760                 765

<210> SEQ ID NO 25
<211> LENGTH: 736
<212> TYPE: PRT
<213> ORGANISM: Hordeum vulgare

<400> SEQUENCE: 25

Gly Glu Met Ala Glu Val Asn Met Thr Gly Gly Ala Ala Glu Lys Leu
1               5                   10                  15

Glu Ser Ser Glu Pro Thr Gln Gly Ile Ala Glu Thr Ile Thr Asp Gly
                20                  25                  30

Val Thr Lys Gly Val Lys Glu Leu Val Val Gly Glu Lys Pro Gln Val
            35                  40                  45

Val Pro Lys Pro Gly Asp Gly Gln Lys Ile Tyr Glu Ile Asp Pro Thr
        50                  55                  60

Leu Lys Asp Phe Arg Ser His Leu Asp Tyr Arg Tyr Ser Glu Tyr Lys
65                  70                  75                  80

Arg Ile Arg Ala Ala Ile Asp Gln His Glu Gly Gly Leu Glu Val Phe
                85                  90                  95

Ser Arg Gly Tyr Glu Lys Leu Gly Phe Thr Arg Ser Ala Lys Gly Ile
            100                 105                 110

Thr Tyr Arg Glu Trp Ala Pro Gly Ala His Ser Ala Ala Leu Val Gly
        115                 120                 125

Asp Phe Asn Asn Trp Asn Pro Asn Ala Asp Thr Met Thr Arg Asp Asp
130                 135                 140

Tyr Gly Val Trp Glu Ile Phe Leu Pro Asn Asn Ala Asp Gly Ser Pro
145                 150                 155                 160

Ala Ile Pro His Gly Ser Arg Val Lys Ile Arg Met Asp Thr Pro Ser
                165                 170                 175

Gly Val Lys Asp Ser Ile Ser Ala Trp Ile Lys Phe Ser Val Gln Ala
            180                 185                 190

Pro Gly Glu Ile Pro Phe Asn Gly Ile Tyr Tyr Asp Pro Pro Glu Glu
        195                 200                 205

Glu Lys Tyr Val Phe Gln His Pro Gln Pro Lys Arg Pro Glu Ser Leu
    210                 215                 220
```

-continued

```
Arg Ile Tyr Glu Ser His Ile Gly Met Ser Ser Pro Glu Pro Lys Ile
225                 230                 235                 240

Asn Ser Tyr Ala Asn Phe Arg Asp Glu Val Leu Pro Arg Ile Lys Arg
            245                 250                 255

Leu Gly Tyr Asn Ala Val Gln Ile Met Ala Ile Gln Glu His Ser Tyr
        260                 265                 270

Tyr Ala Ser Phe Gly Tyr His Val Thr Asn Phe Phe Ala Pro Ser Ser
    275                 280                 285

Arg Phe Gly Thr Pro Glu Asp Leu Lys Ser Leu Ile Asp Arg Ala His
290                 295                 300

Glu Leu Gly Leu Leu Val Leu Met Asp Ile Val His Ser His Ser Ser
305                 310                 315                 320

Asn Asn Thr Leu Asp Gly Leu Asn Gly Phe Asp Gly Thr Asp Thr His
            325                 330                 335

Tyr Phe His Gly Gly Pro Arg Gly His His Trp Met Trp Asp Ser Arg
        340                 345                 350

Leu Phe Asn Tyr Gly Ser Trp Glu Val Leu Arg Phe Leu Leu Ser Asn
    355                 360                 365

Ala Arg Trp Trp Leu Glu Glu Tyr Lys Phe Asp Gly Phe Arg Phe Asp
370                 375                 380

Gly Val Thr Ser Met Met Tyr Thr His His Gly Leu Gln Met Thr Phe
385                 390                 395                 400

Thr Gly Asn Tyr Gly Glu Tyr Phe Gly Phe Ala Thr Asp Val Asp Ala
            405                 410                 415

Val Val Tyr Leu Met Leu Val Asn Asp Leu Ile His Gly Leu Tyr Pro
        420                 425                 430

Asp Ala Val Ser Ile Gly Glu Asp Val Ser Gly Met Pro Thr Phe Cys
    435                 440                 445

Ile Pro Val Pro Asp Gly Gly Val Gly Phe Asp Tyr Arg Leu His Met
450                 455                 460

Ala Val Ala Asp Lys Trp Ile Glu Leu Leu Lys Gln Ser Asp Glu Ser
465                 470                 475                 480

Trp Lys Met Gly Asp Ile Val His Thr Leu Thr Asn Arg Arg Trp Leu
            485                 490                 495

Glu Lys Cys Val Thr Tyr Ala Glu Ser His Asp Gln Ala Leu Val Gly
        500                 505                 510

Asp Lys Thr Ile Ala Phe Trp Leu Met Asp Lys Asp Met Tyr Asp Phe
    515                 520                 525

Met Ala Leu Asp Arg Pro Ser Thr Pro Arg Ile Asp Arg Gly Ile Ala
530                 535                 540

Leu His Lys Met Ile Arg Leu Val Thr Met Gly Leu Gly Gly Glu Gly
545                 550                 555                 560

Tyr Leu Asn Phe Met Gly Asn Glu Phe Gly His Pro Glu Trp Ile Asp
            565                 570                 575

Phe Pro Arg Gly Pro Gln Thr Leu Pro Thr Gly Lys Val Leu Pro Gly
        580                 585                 590

Asn Asn Asn Ser Tyr Asp Lys Cys Arg Arg Phe Asp Leu Gly Asp
    595                 600                 605

Ala Asp Phe Leu Arg Tyr Arg Gly Met Gln Glu Phe Asp Gln Ala Met
610                 615                 620

Gln His Leu Glu Glu Lys Tyr Gly Phe Met Thr Ser Glu His Gln Tyr
625                 630                 635                 640

Val Ser Arg Lys His Glu Glu Asp Lys Val Ile Ile Phe Glu Arg Gly
```

-continued

```
                 645                 650                 655
Asp Leu Val Phe Val Phe Asn Phe His Trp Ser Asn Ser Lys Lys Asp
                660                 665                 670

Tyr Arg Val Gly Cys Ser Lys Pro Gly Lys Tyr Lys Val Ala Leu Asp
            675                 680                 685

Ser Asp Asp Ala Leu Phe Gly Gly Phe Ser Arg Leu Asp His Asp Val
        690                 695                 700

Asp Tyr Phe Thr Thr Glu His Pro His Asp Asn Arg Pro Arg Ser Phe
705                 710                 715                 720

Ser Val Tyr Thr Pro Ser Arg Thr Ala Val Tyr Ala Leu Thr Glu
                725                 730                 735

<210> SEQ ID NO 26
<211> LENGTH: 814
<212> TYPE: PRT
<213> ORGANISM: Zea mays

<400> SEQUENCE: 26

Asp Leu Pro Ser Val Leu Phe Arg Arg Lys Asp Ala Phe Ser Arg Thr
1               5                   10                  15

Val Leu Ser Cys Ala Gly Ala Pro Gly Lys Val Leu Val Pro Gly Gly
            20                  25                  30

Gly Ser Asp Asp Leu Leu Ser Ser Ala Glu Pro Val Val Asp Thr Gln
        35                  40                  45

Pro Glu Glu Leu Gln Ile Pro Glu Ala Glu Leu Thr Val Glu Lys Thr
    50                  55                  60

Ser Ser Ser Pro Thr Gln Thr Thr Ser Ala Val Ala Glu Ala Ser Ser
65                  70                  75                  80

Gly Val Glu Ala Glu Arg Pro Glu Leu Ser Glu Val Ile Gly Val
                85                  90                  95

Gly Gly Thr Gly Gly Thr Lys Ile Asp Gly Ala Gly Ile Lys Ala Lys
            100                 105                 110

Ala Pro Leu Val Glu Glu Lys Pro Arg Val Ile Pro Pro Gly Asp
        115                 120                 125

Gly Gln Arg Ile Tyr Glu Ile Asp Pro Met Leu Glu Gly Phe Arg Gly
    130                 135                 140

His Leu Asp Tyr Arg Tyr Ser Glu Tyr Lys Arg Leu Arg Ala Ala Ile
145                 150                 155                 160

Asp Gln His Glu Gly Gly Leu Asp Ala Phe Ser Arg Gly Tyr Glu Lys
                165                 170                 175

Leu Gly Phe Thr Arg Ser Ala Glu Gly Ile Thr Tyr Arg Glu Trp Ala
            180                 185                 190

Pro Gly Ala Tyr Ser Ala Ala Leu Val Gly Asp Phe Asn Asn Trp Asn
        195                 200                 205

Pro Asn Ala Asp Ala Met Ala Arg Asn Glu Tyr Gly Val Trp Glu Ile
    210                 215                 220

Phe Leu Pro Asn Asn Ala Asp Gly Ser Pro Ala Ile Pro His Gly Ser
225                 230                 235                 240

Arg Val Lys Ile Arg Met Asp Thr Pro Ser Gly Val Lys Asp Ser Ile
                245                 250                 255

Pro Ala Trp Ile Lys Phe Ser Val Gln Ala Pro Gly Glu Ile Pro Tyr
            260                 265                 270

Asn Gly Ile Tyr Tyr Asp Pro Pro Glu Glu Glu Lys Tyr Val Phe Lys
        275                 280                 285
```

```
His Pro Gln Pro Lys Arg Pro Lys Ser Leu Arg Ile Tyr Glu Ser His
    290                 295                 300

Val Gly Met Ser Ser Pro Glu Pro Lys Ile Asn Thr Tyr Ala Asn Phe
305                 310                 315                 320

Arg Asp Glu Val Leu Pro Arg Ile Lys Lys Leu Gly Tyr Asn Ala Val
                325                 330                 335

Gln Ile Met Ala Ile Gln Glu His Ser Tyr Tyr Ala Ser Phe Gly Tyr
                340                 345                 350

His Val Thr Asn Phe Phe Ala Pro Ser Ser Arg Phe Gly Thr Pro Glu
            355                 360                 365

Asp Leu Lys Ser Leu Ile Asp Lys Ala His Glu Leu Gly Leu Leu Val
    370                 375                 380

Leu Met Asp Ile Val His Ser His Ser Ser Asn Asn Thr Leu Asp Gly
385                 390                 395                 400

Leu Asn Gly Phe Asp Gly Thr Asp Thr His Tyr Phe His Gly Gly Pro
                405                 410                 415

Arg Gly His His Trp Met Trp Asp Ser Arg Leu Phe Asn Tyr Gly Ser
                420                 425                 430

Trp Glu Val Leu Arg Phe Leu Leu Ser Asn Ala Arg Trp Trp Leu Glu
                435                 440                 445

Glu Tyr Lys Phe Asp Gly Phe Arg Phe Asp Gly Val Thr Ser Met Met
    450                 455                 460

Tyr Thr His His Gly Leu Gln Val Thr Phe Thr Gly Asn Tyr Gly Glu
465                 470                 475                 480

Tyr Phe Gly Phe Ala Thr Asp Val Asp Ala Val Val Tyr Leu Met Leu
                485                 490                 495

Val Asn Asp Leu Ile Arg Gly Leu Tyr Pro Glu Ala Val Ser Ile Gly
            500                 505                 510

Glu Asp Val Ser Gly Met Pro Thr Phe Cys Ile Pro Val Gln Asp Gly
    515                 520                 525

Gly Val Gly Phe Asp Tyr Arg Leu His Met Ala Val Pro Asp Lys Trp
    530                 535                 540

Ile Glu Leu Leu Lys Gln Ser Asp Glu Tyr Trp Glu Met Gly Asp Ile
545                 550                 555                 560

Val His Thr Leu Thr Asn Arg Arg Trp Leu Glu Lys Cys Val Thr Tyr
                565                 570                 575

Cys Glu Ser His Asp Gln Ala Leu Val Gly Asp Lys Thr Ile Ala Phe
                580                 585                 590

Trp Leu Met Asp Lys Asp Met Tyr Asp Phe Met Ala Leu Asp Arg Pro
    595                 600                 605

Ser Thr Pro Arg Ile Asp Arg Gly Ile Ala Leu His Lys Met Ile Arg
    610                 615                 620

Leu Val Thr Met Gly Leu Gly Gly Glu Gly Tyr Leu Asn Phe Met Gly
625                 630                 635                 640

Asn Glu Phe Gly His Pro Glu Trp Ile Asp Phe Pro Arg Gly Pro Gln
                645                 650                 655

Ser Leu Pro Asn Gly Ser Val Ile Pro Gly Asn Asn Asn Ser Phe Asp
            660                 665                 670

Lys Cys Arg Arg Arg Phe Asp Leu Gly Asp Ala Asp Tyr Leu Arg Tyr
            675                 680                 685

Arg Gly Met Gln Glu Phe Asp Gln Ala Met Gln His Leu Glu Gly Lys
    690                 695                 700

Tyr Glu Phe Met Thr Ser Asp His Ser Tyr Val Ser Arg Lys His Glu
```

```
705                 710                 715                 720
Glu Asp Lys Val Ile Ile Phe Glu Arg Gly Asp Leu Val Phe Val Phe
                725                 730                 735
Asn Phe His Trp Ser Asn Ser Tyr Phe Asp Tyr Arg Val Gly Cys Phe
            740                 745                 750
Lys Pro Gly Lys Tyr Lys Ile Val Leu Asp Ser Asp Gly Leu Phe
        755                 760                 765
Gly Gly Phe Ser Arg Leu Asp His Asp Ala Glu Tyr Phe Thr Ala Asp
        770                 775                 780
Trp Pro His Asp Asn Arg Pro Cys Ser Phe Ser Val Tyr Ala Pro Ser
785                 790                 795                 800
Arg Thr Ala Val Val Tyr Ala Pro Ala Gly Ala Glu Asp Glu
                805                 810
```

<210> SEQ ID NO 27
<211> LENGTH: 841
<212> TYPE: PRT
<213> ORGANISM: Oryza sativa

<400> SEQUENCE: 27

```
Met Ala Ser Phe Ala Val Ser Gly Ala Arg Leu Gly Val Val Arg Ala
1               5                   10                  15
Gly Gly Gly Gly Gly Gly Gly Pro Ala Arg Ser Gly Gly
            20                  25                  30
Val Asp Leu Pro Ser Val Leu Phe Arg Arg Lys Asp Ser Phe Ser Arg
        35                  40                  45
Gly Val Val Ser Cys Ala Gly Ala Pro Gly Lys Val Leu Val Pro Gly
    50                  55                  60
Gly Gly Ser Asp Asp Leu Leu Ser Ser Ala Glu Pro Asp Val Glu Thr
65                  70                  75                  80
Gln Glu Gln Pro Glu Glu Ser Gln Ile Pro Asp Asp Asn Lys Val Lys
                85                  90                  95
Pro Phe Glu Glu Glu Glu Glu Ile Pro Ala Val Ala Glu Ala Ser Ile
            100                 105                 110
Lys Val Val Ala Glu Asp Lys Leu Glu Ser Ser Glu Val Ile Gln Asp
        115                 120                 125
Ile Glu Glu Asn Val Thr Glu Gly Val Ile Lys Asp Ala Asp Glu Pro
    130                 135                 140
Thr Val Glu Asp Lys Pro Arg Val Ile Pro Pro Gly Asp Gly Gln
145                 150                 155                 160
Lys Ile Tyr Gln Ile Asp Pro Met Leu Glu Gly Phe Arg Asn His Leu
                165                 170                 175
Asp Tyr Arg Tyr Ser Glu Tyr Lys Arg Met Arg Ala Ala Ile Asp Gln
            180                 185                 190
His Glu Gly Gly Leu Asp Ala Phe Ser Arg Gly Tyr Glu Lys Leu Gly
        195                 200                 205
Phe Thr Arg Ser Ala Glu Gly Ile Thr Tyr Arg Glu Trp Ala Pro Gly
    210                 215                 220
Ala Gln Ser Ala Ala Leu Val Gly Asp Phe Asn Asn Trp Asn Pro Asn
225                 230                 235                 240
Ala Asp Thr Met Thr Arg Asn Glu Tyr Gly Val Trp Glu Ile Ser Leu
                245                 250                 255
Pro Asn Asn Ala Asp Gly Ser Pro Ala Ile Pro His Gly Ser Arg Val
            260                 265                 270
```

-continued

```
Lys Ile Arg Met Asp Thr Pro Ser Gly Val Lys Asp Ser Ile Pro Ala
            275                 280                 285

Trp Ile Lys Phe Ala Val Gln Ala Pro Gly Glu Ile Pro Tyr Asn Gly
        290                 295                 300

Ile Tyr Tyr Asp Pro Pro Glu Glu Lys Tyr Val Phe Gln His Pro
305                 310                 315                 320

Gln Pro Lys Arg Pro Asn Ser Leu Arg Ile Tyr Glu Ser His Ile Gly
                325                 330                 335

Met Ser Ser Pro Glu Pro Lys Ile Asn Thr Tyr Ala Asn Phe Arg Asp
            340                 345                 350

Glu Val Leu Pro Arg Ile Lys Lys Leu Gly Tyr Asn Ala Val Gln Ile
        355                 360                 365

Met Ala Ile Gln Glu His Ser Tyr Tyr Ala Ser Phe Gly Tyr His Val
    370                 375                 380

Thr Asn Phe Phe Ala Pro Ser Ser Arg Phe Gly Thr Pro Glu Asp Leu
385                 390                 395                 400

Lys Ser Leu Ile Asp Lys Ala His Glu Leu Gly Leu Leu Val Leu Met
                405                 410                 415

Asp Ile Val His Ser His Ala Ser Asn Asn Thr Leu Asp Gly Leu Asn
            420                 425                 430

Gly Phe Asp Gly Thr Asp Thr His Tyr Phe His Gly Gly Pro Arg Gly
        435                 440                 445

His His Trp Met Trp Asp Ser Arg Leu Phe Asn Tyr Gly Ser Trp Glu
    450                 455                 460

Val Leu Arg Tyr Leu Leu Ser Asn Ala Arg Trp Trp Leu Glu Glu Tyr
465                 470                 475                 480

Lys Phe Asp Gly Phe Arg Phe Asp Gly Val Thr Ser Met Met Tyr Thr
                485                 490                 495

His His Gly Leu Gln Val Ala Phe Thr Gly Asn Tyr Gly Glu Tyr Phe
            500                 505                 510

Gly Phe Ala Thr Asp Val Asp Ala Val Val Tyr Leu Met Leu Val Asn
        515                 520                 525

Asp Leu Ile His Gly Leu Tyr Pro Glu Ala Val Ala Ile Gly Glu Asp
    530                 535                 540

Val Ser Gly Met Pro Thr Phe Cys Ile Pro Val Gln Asp Gly Gly Val
545                 550                 555                 560

Gly Phe Asp Tyr Arg Leu His Met Ala Val Pro Asp Lys Trp Ile Glu
                565                 570                 575

Leu Leu Lys Gln Ser Asp Glu Tyr Trp Lys Met Gly Asp Ile Val His
            580                 585                 590

Thr Leu Thr Asn Arg Arg Trp Ser Glu Lys Cys Val Thr Tyr Ala Glu
        595                 600                 605

Ser His Asp Gln Ala Leu Val Gly Asp Lys Thr Ile Ala Phe Trp Leu
    610                 615                 620

Met Asp Lys Asp Met Tyr Asp Phe Met Ala Leu Asp Arg Pro Ser Thr
625                 630                 635                 640

Pro Arg Ile Asp Arg Gly Ile Ala Leu His Lys Met Ile Arg Leu Val
                645                 650                 655

Thr Met Gly Leu Gly Gly Glu Gly Tyr Leu Asn Phe Met Gly Asn Glu
            660                 665                 670

Phe Gly His Pro Glu Trp Ile Asp Phe Pro Arg Gly Pro Gln Ser Leu
        675                 680                 685

Pro Asn Gly Ser Val Leu Pro Gly Asn Asn Tyr Ser Phe Asp Lys Cys
```

```
                690                 695                 700
Arg Arg Arg Phe Asp Leu Gly Asp Ala Asp Tyr Leu Arg Tyr His Gly
705                 710                 715                 720

Met Gln Glu Phe Asp Gln Ala Met Gln His Leu Glu Glu Lys Tyr Gly
                725                 730                 735

Phe Met Thr Ser Glu His Gln Tyr Ile Ser Arg Lys His Glu Glu Asp
                740                 745                 750

Lys Val Ile Ile Phe Glu Arg Gly Asp Leu Val Phe Val Phe Asn Phe
                755                 760                 765

His Trp Ser Asn Ser Tyr Phe Asp Tyr Arg Val Gly Cys Leu Lys Pro
770                 775                 780

Gly Lys Tyr Lys Ile Val Leu Asp Ser Asp Gly Leu Phe Gly Gly
785                 790                 795                 800

Phe Ser Arg Leu Asp His Asp Ala Glu Tyr Phe Thr Ala Asp Trp Pro
                805                 810                 815

His Asp Asn Arg Pro Cys Ser Phe Ser Val Tyr Thr Pro Ser Arg Thr
                820                 825                 830

Ala Val Val Tyr Ala Leu Thr Glu Asp
                835                 840

<210> SEQ ID NO 28
<211> LENGTH: 829
<212> TYPE: PRT
<213> ORGANISM: Hordeum vulgare

<400> SEQUENCE: 28

Met Ala Ala Pro Ala Phe Ala Val Ser Ala Gly Ile Ala Arg Pro
1               5                   10                  15

Ser Ala Arg Arg Ser Ser Gly Ala Glu Pro Arg Ser Leu Leu Phe Gly
                20                  25                  30

Arg Asn Lys Gly Thr Arg Phe Pro Arg Ala Val Gly Val Gly Gly Ser
                35                  40                  45

Gly Trp Arg Val Val Met Arg Ala Gly Gly Pro Ser Gly Glu Val Met
            50                  55                  60

Ile Pro Asp Gly Gly Ser Gly Gly Ser Gly Thr Pro Pro Ser Ile Glu
65                  70                  75                  80

Gly Ser Val Gln Phe Glu Ser Asp Asp Leu Glu Val Pro Phe Ile Asp
                85                  90                  95

Asp Glu Pro Ser Leu His Asp Gly Gly Glu Asp Thr Ile Arg Ser Ser
                100                 105                 110

Glu Thr Tyr Gln Val Thr Glu Glu Ile Asp Ala Glu Gly Val Ser Arg
                115                 120                 125

Met Asp Lys Glu Ser Ser Thr Val Lys Lys Ile Arg Ile Val Pro Gln
            130                 135                 140

Pro Gly Asn Gly Gln Gln Ile Tyr Asp Ile Asp Pro Met Leu Arg Asp
145                 150                 155                 160

Phe Lys Tyr His Leu Glu Tyr Arg Tyr Ser Leu Tyr Arg Arg Ile Arg
                165                 170                 175

Ser Asp Ile Asp Glu Tyr Asp Gly Gly Met Asp Val Phe Ser Arg Gly
                180                 185                 190

Tyr Glu Lys Phe Gly Phe Val Arg Ser Ala Gly Ile Thr Tyr Arg
                195                 200                 205

Glu Trp Ala Pro Gly Ala Asp Ser Ala Ala Leu Val Gly Asp Phe Asn
            210                 215                 220
```

```
Asn Trp Asp Pro Thr Ala Asp His Met Ser Lys Asn Asp Leu Gly Ile
225                 230                 235                 240

Trp Glu Ile Phe Leu Pro Asn Asn Ala Asp Gly Ser Pro Pro Ile Pro
            245                 250                 255

His Gly Ser Arg Val Lys Val Arg Met Asp Thr Pro Ser Gly Thr Lys
        260                 265                 270

Asp Ser Ile Pro Ala Trp Ile Lys Tyr Ser Val Gln Thr Pro Gly Asp
    275                 280                 285

Ile Pro Tyr Asn Gly Ile Tyr Tyr Asp Pro Pro Glu Glu Lys Tyr
290                 295                 300

Val Phe Lys His Pro Gln Pro Lys Arg Pro Lys Ser Leu Arg Ile Tyr
305                 310                 315                 320

Glu Thr His Val Gly Met Ser Ser Pro Glu Pro Lys Ile Asn Thr Tyr
                325                 330                 335

Ala Asn Phe Arg Asp Glu Val Leu Pro Arg Ile Lys Arg Leu Gly Tyr
            340                 345                 350

Asn Ala Val Gln Ile Met Ala Ile Gln Glu His Ser Tyr Tyr Gly Ser
        355                 360                 365

Phe Gly Tyr His Val Thr Asn Phe Phe Ala Pro Ser Ser Arg Phe Gly
370                 375                 380

Ser Pro Glu Asp Leu Lys Ser Leu Ile Asp Arg Ala His Glu Leu Gly
385                 390                 395                 400

Leu Leu Val Leu Met Asp Val Val His Ser His Ala Ser Ser Asn Thr
                405                 410                 415

Leu Asp Gly Leu Asn Gly Phe Asp Gly Thr Asp Thr His Tyr Phe His
            420                 425                 430

Gly Gly Ser Arg Gly His His Trp Met Trp Asp Ser Arg Val Phe Asn
        435                 440                 445

Tyr Gly Asn Lys Glu Val Ile Arg Phe Leu Leu Ser Asn Ala Arg Trp
450                 455                 460

Trp Leu Glu Glu Tyr Lys Phe Asp Gly Phe Arg Phe Asp Gly Ala Thr
465                 470                 475                 480

Ser Met Met Tyr Thr His His Gly Leu Gln Val Thr Phe Thr Gly Ser
                485                 490                 495

Tyr His Glu Tyr Phe Gly Phe Ala Thr Asp Val Asp Ala Val Val Tyr
            500                 505                 510

Leu Met Leu Val Asn Asp Leu Ile His Ala Leu Tyr Pro Glu Ala Val
        515                 520                 525

Thr Ile Gly Glu Asp Val Ser Gly Met Pro Thr Phe Ala Leu Pro Val
530                 535                 540

Gln Val Gly Gly Val Gly Phe Asp Tyr Arg Leu His Met Ala Val Ala
545                 550                 555                 560

Asp Lys Trp Ile Glu Leu Leu Lys Gly Ser Asp Glu Gly Trp Glu Met
                565                 570                 575

Gly Asn Ile Val His Thr Leu Thr Asn Arg Arg Trp Leu Glu Lys Cys
            580                 585                 590

Val Thr Tyr Ala Glu Ser His Asp Gln Ala Leu Val Gly Asp Lys Thr
        595                 600                 605

Ile Ala Phe Trp Leu Met Asp Lys Asp Met Tyr Asp Phe Met Ala Leu
610                 615                 620

Asn Gly Pro Ser Thr Pro Asn Ile Asp Arg Gly Ile Ala Leu His Lys
625                 630                 635                 640

Met Ile Arg Leu Ile Thr Met Ala Leu Gly Gly Glu Gly Tyr Leu Asn
```

-continued

```
                645                 650                 655
Phe Met Gly Asn Glu Phe Gly His Pro Glu Trp Ile Asp Phe Pro Arg
            660                 665                 670
Gly Pro Gln Val Leu Pro Thr Gly Lys Phe Ile Pro Gly Asn Asn Asn
        675                 680                 685
Ser Tyr Asp Lys Cys Arg Arg Phe Asp Leu Gly Asp Ala Glu Phe
    690                 695                 700
Leu Arg Tyr His Gly Met Gln Gln Phe Asp Gln Ala Met Gln His Leu
705                 710                 715                 720
Glu Glu Lys Tyr Gly Phe Met Thr Ser Asp His Gln Tyr Val Ser Arg
                725                 730                 735
Lys His Glu Glu Asp Lys Val Ile Val Phe Glu Lys Gly Asp Leu Val
            740                 745                 750
Phe Val Phe Asn Phe His Trp Ser Asn Ser Tyr Phe Asp Tyr Arg Val
        755                 760                 765
Gly Cys Leu Lys Pro Gly Lys Tyr Lys Val Val Leu Asp Ser Asp Ala
    770                 775                 780
Gly Leu Phe Gly Gly Phe Gly Arg Ile His His Thr Gly Glu His Phe
785                 790                 795                 800
Thr Asn Gly Cys Gln His Asp Asn Arg Pro His Ser Phe Ser Val Tyr
                805                 810                 815
Thr Pro Ser Arg Thr Cys Val Val Tyr Ala Pro Met Asn
                820                 825
```

<210> SEQ ID NO 29
<211> LENGTH: 836
<212> TYPE: PRT
<213> ORGANISM: Triticum sp.

<400> SEQUENCE: 29

```
Met Ala Ala Pro Ala Phe Ala Val Ser Ala Ala Gly Leu Ala Arg Pro
1               5                   10                  15
Ser Ala Pro Arg Ser Gly Gly Ala Glu Arg Arg Gly Arg Gly Val Glu
            20                  25                  30
Leu Gln Ser Pro Ser Leu Leu Phe Gly Arg Asn Lys Gly Thr Arg Ser
        35                  40                  45
Pro Arg Ala Val Gly Val Gly Gly Ser Gly Trp Arg Val Val Met Arg
    50                  55                  60
Ala Gly Gly Pro Ser Gly Glu Val Met Ile Pro Asp Gly Gly Ser Gly
65                  70                  75                  80
Gly Thr Pro Pro Ser Ile Asp Gly Pro Val Gln Phe Asp Ser Asp
                85                  90                  95
Leu Lys Val Pro Phe Ile Asp Asp Glu Pro Ser Leu His Asp Gly Gly
            100                 105                 110
Glu Asp Thr Ile Trp Ser Ser Glu Thr Asn Gln Val Ser Glu Glu Ile
        115                 120                 125
Asp Ala Glu Asp Thr Ser Arg Met Asp Lys Glu Ser Ser Thr Arg Glu
    130                 135                 140
Lys Leu Arg Ile Leu Pro Pro Gly Asn Gly Gln Gln Ile Tyr Glu
145                 150                 155                 160
Ile Asp Pro Thr Leu Arg Asp Phe Lys Tyr His Leu Glu Tyr Arg Tyr
                165                 170                 175
Ser Leu Tyr Arg Arg Ile Arg Ser Asp Ile Asp Glu His Glu Gly Gly
            180                 185                 190
```

```
Met Asp Val Phe Ser Arg Gly Tyr Glu Lys Phe Gly Phe Met Arg Ser
        195                 200                 205

Ala Glu Gly Ile Thr Tyr Arg Glu Trp Ala Pro Gly Ala Asp Ser Ala
        210                 215                 220

Ala Leu Val Gly Asp Phe Asn Asn Trp Asp Pro Asn Ala Asp His Met
225                 230                 235                 240

Ser Lys Asn Asp Leu Gly Val Trp Glu Ile Phe Leu Pro Asn Asn Ala
        245                 250                 255

Asp Gly Ser Pro Pro Ile Pro His Gly Ser Arg Val Lys Val Arg Met
        260                 265                 270

Gly Thr Pro Ser Gly Thr Lys Asp Ser Ile Pro Ala Trp Ile Lys Tyr
        275                 280                 285

Ser Val Gln Thr Pro Gly Asp Ile Pro Tyr Asn Gly Ile Tyr Tyr Asp
        290                 295                 300

Pro Pro Glu Glu Glu Lys Tyr Val Phe Lys His Pro Gln Pro Lys Arg
305                 310                 315                 320

Pro Lys Ser Leu Arg Ile Tyr Glu Thr His Val Gly Met Ser Ser Pro
                325                 330                 335

Glu Pro Lys Ile Asn Thr Tyr Ala Asn Phe Arg Asp Glu Val Leu Pro
        340                 345                 350

Arg Ile Lys Arg Leu Gly Tyr Asn Ala Val Gln Ile Met Ala Ile Gln
        355                 360                 365

Glu His Ser Tyr Tyr Gly Ser Phe Gly Tyr His Val Thr Asn Phe Phe
        370                 375                 380

Ala Pro Ser Ser Arg Phe Gly Ser Pro Glu Asp Leu Lys Ser Leu Ile
385                 390                 395                 400

Asp Arg Ala His Glu Leu Gly Leu Val Val Leu Met Asp Val Val His
                405                 410                 415

Ser His Ala Ser Asn Asn Thr Leu Asp Gly Leu Asn Gly Phe Asp Gly
                420                 425                 430

Thr Asp Thr His Tyr Phe His Gly Gly Ser Arg Gly His His Trp Met
        435                 440                 445

Trp Asp Ser Arg Val Phe Asn Tyr Gly Asn Lys Glu Val Ile Arg Phe
        450                 455                 460

Leu Leu Ser Asn Ala Arg Trp Trp Leu Glu Glu Tyr Lys Phe Asp Gly
465                 470                 475                 480

Phe Arg Phe Asp Gly Ala Thr Ser Met Met Tyr Thr His His Gly Leu
                485                 490                 495

Gln Val Thr Phe Thr Gly Ser Tyr His Glu Tyr Phe Gly Phe Ala Thr
        500                 505                 510

Asp Val Asp Ala Val Val Tyr Leu Met Leu Met Asn Asp Leu Ile His
        515                 520                 525

Gly Phe Tyr Pro Glu Ala Val Thr Ile Gly Glu Asp Val Ser Gly Met
530                 535                 540

Pro Thr Phe Ala Leu Pro Val Gln Val Gly Gly Val Gly Phe Asp Tyr
545                 550                 555                 560

Arg Leu His Met Ala Val Ala Arg Lys Trp Ile Glu Leu Leu Lys Gly
                565                 570                 575

Asn Asp Glu Ala Trp Glu Met Gly Asn Ile Val His Thr Leu Thr Asn
        580                 585                 590

Arg Arg Trp Leu Glu Lys Cys Val Thr Tyr Ala Glu Ser His Asp Gln
        595                 600                 605

Ala Leu Val Gly Asp Lys Thr Ile Ala Phe Trp Leu Met Asp Lys Asp
```

-continued

```
                610                 615                 620
Met Tyr Asp Phe Met Ala Leu Asn Gly Pro Ser Thr Pro Asn Ile Asp
625                 630                 635                 640

Arg Gly Ile Ala Leu His Lys Met Ile Arg Leu Ile Thr Met Gly Leu
            645                 650                 655

Gly Gly Glu Gly Tyr Leu Asn Phe Met Gly Asn Glu Phe Gly His Pro
        660                 665                 670

Glu Trp Ile Asp Phe Pro Arg Gly Pro Gln Val Leu Pro Ser Gly Lys
    675                 680                 685

Phe Ile Pro Gly Asn Asn Asn Ser Tyr Asp Lys Cys Arg Arg Arg Phe
690                 695                 700

Asp Leu Gly Asp Ala Glu Phe Leu Arg Tyr His Gly Met Gln Gln Phe
705                 710                 715                 720

Asp Gln Ala Met Gln His Leu Glu Glu Lys Tyr Gly Phe Met Thr Ser
            725                 730                 735

Asp His Gln Tyr Val Ser Arg Lys His Glu Asp Lys Val Ile Val
        740                 745                 750

Phe Glu Lys Gly Asp Leu Val Phe Val Phe Asn Phe His Trp Ser Ser
    755                 760                 765

Ser Tyr Phe Asp Tyr Arg Val Gly Cys Leu Lys Pro Gly Lys Tyr Lys
770                 775                 780

Val Val Leu Asp Ser Asp Ala Gly Leu Phe Gly Gly Phe Gly Arg Ile
785                 790                 795                 800

His His Thr Ala Glu His Phe Thr Ser Asp Cys Gln His Asp Asn Arg
            805                 810                 815

Pro His Ser Phe Ser Val Tyr Thr Pro Ser Arg Thr Cys Val Val Tyr
        820                 825                 830

Ala Pro Met Asn
        835

<210> SEQ ID NO 30
<211> LENGTH: 741
<212> TYPE: PRT
<213> ORGANISM: Zea mays

<400> SEQUENCE: 30

Lys Ala Val Met Val Pro Glu Gly Glu Asn Asp Gly Leu Ala Ser Arg
1               5                   10                  15

Ala Asp Ser Ala Gln Phe Gln Ser Asp Glu Leu Glu Val Pro Asp Ile
            20                  25                  30

Ser Glu Glu Thr Thr Cys Gly Ala Gly Val Ala Asp Ala Gln Ala Leu
        35                  40                  45

Asn Arg Val Arg Val Val Pro Pro Ser Asp Gly Gln Lys Ile Phe
50                  55                  60

Gln Ile Asp Pro Met Leu Gln Gly Tyr Lys Tyr His Leu Glu Tyr Arg
65                  70                  75                  80

Tyr Ser Leu Tyr Arg Arg Ile Arg Ser Asp Ile Asp Glu His Glu Gly
            85                  90                  95

Gly Leu Glu Ala Phe Ser Arg Ser Tyr Glu Lys Phe Gly Phe Asn Ala
        100                 105                 110

Ser Ala Glu Gly Ile Thr Tyr Arg Glu Trp Ala Pro Gly Ala Phe Ser
    115                 120                 125

Ala Ala Leu Val Gly Asp Val Asn Asn Trp Asp Pro Asn Ala Asp Arg
130                 135                 140
```

-continued

```
Met Ser Lys Asn Glu Phe Gly Val Trp Glu Ile Phe Leu Pro Asn Asn
145                 150                 155                 160

Ala Asp Gly Thr Ser Pro Ile Pro His Gly Ser Arg Val Lys Val Arg
            165                 170                 175

Met Asp Thr Pro Ser Gly Ile Lys Asp Ser Ile Pro Ala Trp Ile Lys
        180                 185                 190

Tyr Ser Val Gln Ala Pro Gly Glu Ile Pro Tyr Asp Gly Ile Tyr Tyr
    195                 200                 205

Asp Pro Pro Glu Glu Val Lys Tyr Val Phe Arg His Ala Gln Pro Lys
210                 215                 220

Arg Pro Lys Ser Leu Arg Ile Tyr Glu Thr His Val Gly Met Ser Ser
225                 230                 235                 240

Pro Glu Pro Lys Ile Asn Thr Tyr Val Asn Phe Arg Asp Glu Val Leu
                245                 250                 255

Pro Arg Ile Lys Lys Leu Gly Tyr Asn Ala Val Gln Ile Met Ala Ile
            260                 265                 270

Gln Glu His Ser Tyr Tyr Gly Ser Phe Gly Tyr His Val Thr Asn Phe
        275                 280                 285

Phe Ala Pro Ser Ser Arg Phe Gly Thr Pro Glu Asp Leu Lys Ser Leu
    290                 295                 300

Ile Asp Arg Ala His Glu Leu Gly Leu Leu Val Leu Met Asp Val Val
305                 310                 315                 320

His Ser His Ala Ser Ser Asn Thr Leu Asp Gly Leu Asn Gly Phe Asp
                325                 330                 335

Gly Thr Asp Thr His Tyr Phe His Ser Gly Pro Arg Gly His His Trp
            340                 345                 350

Met Trp Asp Ser Arg Leu Phe Asn Tyr Gly Asn Trp Glu Val Leu Arg
        355                 360                 365

Phe Leu Leu Ser Asn Ala Arg Trp Trp Leu Glu Glu Tyr Lys Phe Asp
    370                 375                 380

Gly Phe Arg Phe Asp Gly Val Thr Ser Met Met Tyr Thr His His Gly
385                 390                 395                 400

Leu Gln Val Thr Phe Thr Gly Asn Phe Asn Glu Tyr Phe Gly Phe Ala
                405                 410                 415

Thr Asp Val Asp Ala Val Val Tyr Leu Met Leu Val Asn Asp Leu Ile
            420                 425                 430

His Gly Leu Tyr Pro Glu Ala Val Thr Ile Gly Glu Asp Val Ser Gly
        435                 440                 445

Met Pro Thr Phe Ala Leu Pro Val His Asp Gly Gly Val Gly Phe Asp
    450                 455                 460

Tyr Arg Met His Met Ala Val Ala Asp Lys Trp Ile Asp Leu Leu Lys
465                 470                 475                 480

Gln Ser Asp Glu Thr Trp Lys Met Gly Asp Ile Val His Thr Leu Thr
                485                 490                 495

Asn Arg Arg Trp Leu Glu Lys Cys Val Thr Tyr Ala Glu Ser His Asp
            500                 505                 510

Gln Ala Leu Val Gly Asp Lys Thr Ile Ala Phe Trp Leu Met Asp Lys
        515                 520                 525

Asp Met Tyr Asp Phe Met Ala Leu Asp Arg Pro Ser Thr Pro Thr Ile
    530                 535                 540

Asp Arg Gly Ile Ala Leu His Lys Met Ile Arg Leu Ile Thr Met Gly
545                 550                 555                 560

Leu Gly Gly Glu Gly Tyr Leu Asn Phe Met Gly Asn Glu Phe Gly His
```

```
                       565                 570                 575
Pro Glu Trp Ile Asp Phe Pro Arg Gly Pro Gln Arg Leu Pro Ser Gly
                580                 585                 590

Lys Phe Ile Pro Gly Asn Asn Asn Ser Tyr Asp Lys Cys Arg Arg Arg
            595                 600                 605

Phe Asp Leu Gly Asp Ala Asp Tyr Leu Arg Tyr His Gly Met Gln Glu
        610                 615                 620

Phe Asp Gln Ala Met Gln His Leu Glu Gln Lys Tyr Glu Phe Met Thr
625                 630                 635                 640

Ser Asp His Gln Tyr Ile Ser Arg Lys His Glu Glu Asp Lys Val Ile
                645                 650                 655

Val Phe Glu Lys Gly Asp Leu Val Phe Val Phe Asn Phe His Cys Asn
            660                 665                 670

Asn Ser Tyr Phe Asp Tyr Arg Ile Gly Cys Arg Lys Pro Gly Val Tyr
        675                 680                 685

Lys Val Val Leu Asp Ser Asp Ala Gly Leu Phe Gly Gly Phe Ser Arg
    690                 695                 700

Ile His His Ala Ala Glu His Phe Thr Ala Asp Cys Ser His Asp Asn
705                 710                 715                 720

Arg Pro Tyr Ser Phe Ser Val Tyr Thr Pro Ser Arg Thr Cys Val Val
                725                 730                 735

Tyr Ala Pro Val Glu
            740

<210> SEQ ID NO 31
<211> LENGTH: 825
<212> TYPE: PRT
<213> ORGANISM: Oryza sativa

<400> SEQUENCE: 31

Met Ala Ala Pro Ala Ser Ala Val Pro Gly Ser Ala Ala Gly Leu Arg
1               5                   10                  15

Ala Gly Ala Val Arg Phe Pro Val Pro Ala Gly Ala Arg Ser Trp Arg
            20                  25                  30

Ala Ala Ala Glu Leu Pro Thr Ser Arg Ser Leu Leu Ser Gly Arg Arg
        35                  40                  45

Phe Pro Gly Ala Val Arg Val Gly Gly Ser Gly Gly Arg Val Ala Val
    50                  55                  60

Arg Ala Ala Gly Ala Ser Gly Glu Val Met Ile Pro Glu Gly Glu Ser
65                  70                  75                  80

Asp Gly Met Pro Val Ser Ala Gly Ser Asp Asp Leu Gln Leu Pro Ala
                85                  90                  95

Leu Asp Asp Glu Leu Ser Thr Glu Val Gly Ala Glu Val Glu Ile Glu
            100                 105                 110

Ser Ser Gly Ala Ser Asp Val Glu Gly Val Lys Arg Val Val Glu Glu
        115                 120                 125

Leu Ala Ala Glu Gln Lys Pro Arg Val Val Pro Pro Thr Gly Asp Gly
    130                 135                 140

Gln Lys Ile Phe Gln Met Asp Ser Met Leu Asn Gly Tyr Lys Tyr His
145                 150                 155                 160

Leu Glu Tyr Arg Tyr Ser Leu Tyr Arg Arg Leu Arg Ser Asp Ile Asp
                165                 170                 175

Gln Tyr Glu Gly Gly Leu Glu Thr Phe Ser Arg Gly Tyr Glu Lys Phe
            180                 185                 190
```

```
Gly Phe Asn His Ser Ala Glu Gly Val Thr Tyr Arg Glu Trp Ala Pro
            195                 200                 205

Gly Ala His Ser Ala Ala Leu Val Gly Asp Phe Asn Asn Trp Asn Pro
        210                 215                 220

Asn Ala Asp Arg Met Ser Lys Asn Glu Phe Gly Val Trp Glu Ile Phe
225                 230                 235                 240

Leu Pro Asn Asn Ala Asp Gly Ser Ser Pro Ile Pro His Gly Ser Arg
                245                 250                 255

Val Lys Val Arg Met Glu Thr Pro Ser Gly Ile Lys Asp Ser Ile Pro
                260                 265                 270

Ala Trp Ile Lys Tyr Ser Val Gln Ala Ala Gly Glu Ile Pro Tyr Asn
            275                 280                 285

Gly Ile Tyr Tyr Asp Pro Pro Glu Glu Glu Lys Tyr Ile Phe Lys His
        290                 295                 300

Pro Gln Pro Lys Arg Pro Lys Ser Leu Arg Ile Tyr Glu Thr His Val
305                 310                 315                 320

Gly Met Ser Ser Thr Glu Pro Lys Ile Asn Thr Tyr Ala Asn Phe Arg
                325                 330                 335

Asp Glu Val Leu Pro Arg Ile Lys Lys Leu Gly Tyr Asn Ala Val Gln
                340                 345                 350

Ile Met Ala Ile Gln Glu His Ala Tyr Tyr Gly Ser Phe Gly Tyr His
            355                 360                 365

Val Thr Asn Phe Phe Ala Pro Ser Ser Arg Phe Gly Thr Pro Glu Asp
        370                 375                 380

Leu Lys Ser Leu Ile Asp Lys Ala His Glu Leu Gly Leu Val Val Leu
385                 390                 395                 400

Met Asp Val Val His Ser His Ala Ser Asn Asn Thr Leu Asp Gly Leu
                405                 410                 415

Asn Gly Phe Asp Gly Thr Asp Thr His Tyr Phe His Ser Gly Ser Arg
                420                 425                 430

Gly His His Trp Met Trp Asp Ser Arg Leu Phe Asn Tyr Gly Asn Trp
            435                 440                 445

Glu Val Leu Arg Phe Leu Leu Ser Asn Ala Arg Trp Trp Leu Glu Glu
        450                 455                 460

Tyr Lys Phe Asp Gly Phe Arg Phe Asp Gly Val Thr Ser Met Met Tyr
465                 470                 475                 480

Thr His His Gly Leu Gln Val Ala Phe Thr Gly Asn Tyr Ser Glu Tyr
                485                 490                 495

Phe Gly Phe Ala Thr Asp Ala Asp Ala Val Val Tyr Leu Met Leu Val
                500                 505                 510

Asn Asp Leu Ile His Gly Leu Tyr Pro Glu Ala Ile Thr Ile Gly Glu
            515                 520                 525

Asp Val Ser Gly Met Pro Thr Phe Ala Leu Pro Val Gln Asp Gly Gly
        530                 535                 540

Val Gly Phe Asp Tyr Arg Leu His Met Ala Val Pro Asp Lys Trp Ile
545                 550                 555                 560

Glu Leu Leu Lys Gln Ser Asp Glu Ser Trp Lys Met Gly Asp Ile Val
                565                 570                 575

His Thr Leu Thr Asn Arg Arg Trp Ser Glu Lys Cys Val Thr Tyr Ala
                580                 585                 590

Glu Ser His Asp Gln Ala Leu Val Gly Asp Lys Thr Ile Ala Phe Trp
            595                 600                 605

Leu Met Asp Lys Asp Met Tyr Asp Phe Met Ala Leu Asp Arg Pro Ala
```

```
                610                 615                 620
Thr Pro Ser Ile Asp Arg Gly Ile Ala Leu His Lys Met Ile Arg Leu
625                 630                 635                 640

Ile Thr Met Gly Leu Gly Gly Glu Gly Tyr Leu Asn Phe Met Gly Asn
                645                 650                 655

Glu Phe Gly His Pro Glu Trp Ile Asp Phe Pro Arg Ala Pro Gln Val
                660                 665                 670

Leu Pro Asn Gly Lys Phe Ile Pro Gly Asn Asn Ser Tyr Asp Lys
            675                 680                 685

Cys Arg Arg Arg Phe Asp Leu Gly Asp Ala Asp Tyr Leu Arg Tyr Arg
690                 695                 700

Gly Met Leu Glu Phe Asp Arg Ala Met Gln Ser Leu Glu Glu Lys Tyr
705                 710                 715                 720

Gly Phe Met Thr Ser Asp His Gln Tyr Ile Ser Arg Lys His Glu Glu
                725                 730                 735

Asp Lys Met Ile Ile Phe Glu Lys Gly Asp Leu Val Phe Val Phe Asn
                740                 745                 750

Phe His Trp Ser Asn Ser Tyr Phe Asp Tyr Arg Val Gly Cys Leu Lys
            755                 760                 765

Pro Gly Lys Tyr Lys Val Val Leu Asp Ser Asp Ala Gly Leu Phe Gly
            770                 775                 780

Gly Phe Gly Arg Ile His His Thr Ala Glu His Phe Thr Ala Asp Cys
785                 790                 795                 800

Ser His Asp Asn Arg Pro Tyr Ser Phe Ser Val Tyr Ser Pro Ser Arg
                805                 810                 815

Thr Cys Val Val Tyr Ala Pro Ala Glu
                820                 825

<210> SEQ ID NO 32
<211> LENGTH: 248
<212> TYPE: DNA
<213> ORGANISM: Triticum sp.

<400> SEQUENCE: 32
tggcggcggc gacgggatgg ctgcgccggc attcgcagtt tccgcggcgg ggctggcccg      60
gccgtcggct cctcgatccg gcggggcaga gcggaggggg gcggggtgg agctgcagtc     120 gccatcgctg ctcttcggcc gcaacaaggg caccgttca ccccgtgccg tcggcgtcgg     180
aggttctgga tggcgcgtgg tcatgcgcgc ggggggccg tccggggagg tgatgatccc     240
tgacggcg                                                              248

<210> SEQ ID NO 33
<211> LENGTH: 244
<212> TYPE: DNA
<213> ORGANISM: Triticum sp.

<400> SEQUENCE: 33
tgcggcgacg ggatggctgc gccggcattc gcagtttccg cggcggggct ggccggccg      60 tcggctcctc gatccggcgg ggcagagcgg agggggcgcg gggtggagct gcagtcgcca    120
tcgctgctct tcggccgcaa caagggcacc cgttcacccc gtgccgtcgg cgtcggaggt    180
tctggatggc gcgtggtcat gcgcgcgggg gggccgtccg ggaggtgat gatccctgac    240 ggcg                                                                 244

<210> SEQ ID NO 34
```

<211> LENGTH: 396
<212> TYPE: DNA
<213> ORGANISM: Triticum sp.

<400> SEQUENCE: 34

| | | | | | |
|---|---|---|---|---|---|
| cggcggcggc | gacgggatgg | ctgcgccggc | attcgcagtt | tccgcggcgg | ggctggcccg | 60 |
| gccgtcggct | cctcgatccg | gcggggcaga | gcggaggggg | cgcggggtgg | agctgcagtc | 120 |
| gccatcgctg | ctcttcggcc | gcaacaaggg | cacccgttca | ccccgtaatt | atttgcgcca | 180 |
| cctttctcac | tcacattctc | tcgtgtattc | tgtcgtgctc | gcccttcgcc | gacgacgcgt | 240 |
| gccgattccg | tatcgggctg | cggtgttcag | cgatcttacg | tcgttccct | cctggtgtgg | 300 |
| tgatgtctgt | aggtgccgtc | ggcgtcggag | gttctggatg | gcgcgtggtc | atgcgcgcgg | 360 |
| gggggccgtc | cggggaggtg | atgatccctg | acggcg | | | 396 |

<210> SEQ ID NO 35
<211> LENGTH: 510
<212> TYPE: DNA
<213> ORGANISM: Hordeum vulgare

<400> SEQUENCE: 35

| | | | | | |
|---|---|---|---|---|---|
| ttctgccacc | accgggaaat | ggacagcaaa | tatacgagat | tgacccaacg | ctccgagact | 60 |
| ttaagtacca | tcttgagtat | cggtatgctt | cgcttctatt | gtgtgcactt | taaactttaa | 120 |
| atacaattta | cagtctttga | taagatgtga | atggctgctt | gctgtgacac | aaaactcttg | 180 |
| aagttcgtag | tcactcttgt | gtgttcatgg | ctctgaggtg | acatggtaac | cgaacaaaaa | 240 |
| taggaaagtg | gcaagaactg | caatgtgagc | taccgataag | cacccattgt | aattgggtac | 300 |
| actgattaat | atatgtcttg | atgggttcta | tgttttttca | gtatctatgc | caattgaaca | 360 |
| acaatgccac | ttcatttccc | ctgtgttgct | tttgtaagga | tgaaacccat | atgtccagat | 420 |
| caaactgtac | tagcagtctc | actgtgcctt | aatggatcaa | aaacagatac | agcctatata | 480 |
| ggagaatacg | ttcagacatt | gatgaacacg | | | | 510 |

<210> SEQ ID NO 36
<211> LENGTH: 345
<212> TYPE: DNA
<213> ORGANISM: Hordeum vulgare

<400> SEQUENCE: 36

| | | | | | |
|---|---|---|---|---|---|
| gcttcgcttc | tattgtgtgc | actttaaaaa | caatttacag | tctttgataa | gatgtgaatg | 60 |
| gctgcttgct | gtgacacaaa | actcttgaag | ttcgtagtca | ctcttgtgtg | ttcatggctc | 120 |
| tgaggtgaca | tggtaaccga | acaaaaatag | gaaagtggca | agaactgcaa | tgtgagctac | 180 |
| cgataagcac | ccattgtaat | tgggtacact | gattaatata | tgtcttgatg | ggttctatgt | 240 |
| tttttcagta | tctatgccaa | ttgaacaaca | atgccacttc | atttcccctg | tgttgctttt | 300 |
| gtaaggatga | aacacatatg | tccagatcaa | actatactag | cagtc | | 345 |

<210> SEQ ID NO 37
<211> LENGTH: 591
<212> TYPE: DNA
<213> ORGANISM: Hordeum vulgare

<400> SEQUENCE: 37

| | | | | | |
|---|---|---|---|---|---|
| ttctgccacc | accgggaaat | ggacagcaaa | tatacgagat | tgacccaacg | ctccgagact | 60 |
| ttaagtacca | tcttgagtat | cggtatgctt | cgcttctatt | gtgtgcactt | taaaaacaat | 120 |
| ttacagtctt | tgataagatg | tgaatggctg | cttgctgtga | cacgaaactc | ttgaagttcg | 180 |

-continued

```
tagtcactct tgtgtgttca tggttctgag gtaacatggt aaccgaacaa aaataggaaa      240
gtggcaagca ctgcaatgtg agctactgat aaccacccat tgtaattggg tacactgatt      300
aatatatatg tcttcatggg ctctattttt tttcaatatc tatgccaatt gaacaacaat      360
gctttgtgga cgggtgttct tttaccctct tcttctatca atagatgata tgcatactca      420
tgcgtatcct acaaaaaatt gaacaacaat gccactttcc cccgtgttgc ttttgtaagg      480
atgaaacaca tatgtccaga tcaaactata ctagcagtct aactgtgcct taatggatca      540
aaaacagata tagcctatac aggagaatac gttcagacat tgatgaacac g               591
```

```
<210> SEQ ID NO 38
<211> LENGTH: 8
<212> TYPE: PRT
<213> ORGANISM: Triticum sp.

<400> SEQUENCE: 38

Lys Arg Pro Lys Ser Leu Arg Ile
1               5

<210> SEQ ID NO 39
<211> LENGTH: 13
<212> TYPE: PRT
<213> ORGANISM: Triticum sp.

<400> SEQUENCE: 39

Arg Val Phe Asn Tyr Gly Asn Lys Glu Val Ile Arg Phe
1               5                   10

<210> SEQ ID NO 40
<211> LENGTH: 13
<212> TYPE: PRT
<213> ORGANISM: Triticum sp.

<400> SEQUENCE: 40

Arg Arg Phe Asp Leu Gly Asp Ala Glu Phe Leu Arg Tyr
1               5                   10

<210> SEQ ID NO 41
<211> LENGTH: 17
<212> TYPE: PRT
<213> ORGANISM: Triticum sp.

<400> SEQUENCE: 41

Lys Val Val Leu Asp Ser Asp Ala Gly Leu Phe Gly Gly Phe Gly Arg
1               5                   10                  15

Ile

<210> SEQ ID NO 42
<211> LENGTH: 15
<212> TYPE: PRT
<213> ORGANISM: Triticum sp.

<400> SEQUENCE: 42

Lys Tyr Gly Phe Met Thr Ser Asp His Gln Tyr Val Ser Arg Lys
1               5                   10                  15

<210> SEQ ID NO 43
<211> LENGTH: 17
<212> TYPE: PRT
<213> ORGANISM: Triticum sp.

<400> SEQUENCE: 43
```

```
Arg Ser Asp Ile Asp Glu His Glu Gly Gly Met Asp Val Phe Ser Arg
1               5                   10                  15

Gly

<210> SEQ ID NO 44
<211> LENGTH: 16
<212> TYPE: PRT
<213> ORGANISM: Triticum sp.

<400> SEQUENCE: 44

Lys Ile Asn Thr Tyr Ala Asn Phe Arg Asp Glu Val Leu Pro Arg Ile
1               5                   10                  15

<210> SEQ ID NO 45
<211> LENGTH: 9
<212> TYPE: PRT
<213> ORGANISM: Triticum sp.

<400> SEQUENCE: 45

Arg Phe Leu Leu Ser Asn Ala Arg Trp
1               5

<210> SEQ ID NO 46
<211> LENGTH: 11
<212> TYPE: PRT
<213> ORGANISM: Triticum sp.

<400> SEQUENCE: 46

Arg Gly His His Trp Met Trp Asp Ser Arg Val
1               5                   10

<210> SEQ ID NO 47
<211> LENGTH: 16
<212> TYPE: PRT
<213> ORGANISM: Triticum sp.

<400> SEQUENCE: 47

Arg Ile Tyr Glu Thr His Val Gly Met Ser Ser Pro Glu Pro Lys Ile
1               5                   10                  15

<210> SEQ ID NO 48
<211> LENGTH: 14
<212> TYPE: PRT
<213> ORGANISM: Triticum sp.

<400> SEQUENCE: 48

Lys Ile Tyr Glu Ile Asp Pro Thr Leu Lys Asp Phe Arg Ser
1               5                   10

<210> SEQ ID NO 49
<211> LENGTH: 16
<212> TYPE: PRT
<213> ORGANISM: Triticum sp.

<400> SEQUENCE: 49

Arg Ile Tyr Glu Ser His Ile Gly Met Ser Ser Pro Glu Pro Lys Ile
1               5                   10                  15

<210> SEQ ID NO 50
<211> LENGTH: 17
<212> TYPE: PRT
<213> ORGANISM: Triticum sp.

<400> SEQUENCE: 50
```

-continued

```
Arg Ala Ala Ile Asp Gln His Glu Gly Gly Leu Glu Ala Phe Ser Arg
1               5                   10                  15
Gly

<210> SEQ ID NO 51
<211> LENGTH: 16
<212> TYPE: PRT
<213> ORGANISM: Triticum sp.

<400> SEQUENCE: 51

Lys Ile Asn Ser Tyr Ala Asn Phe Arg Asp Glu Val Leu Pro Arg Ile
1               5                   10                  15
```